(12) United States Patent
Virgili-Bernado et al.

(10) Patent No.: US 10,421,750 B2
(45) Date of Patent: Sep. 24, 2019

(54) SUBSTITUTED MORPHOLINE DERIVATIVES HAVING ACTIVITY AGAINST PAIN

(71) Applicant: ESTEVE PHARMACEUTICALS, S.A., Barcelone (ES)

(72) Inventors: Marina Virgili-Bernado, Barcelona (ES); Carlos Alegret-Molina, Barcelona (ES)

(73) Assignee: ESTEVE PHARMACEUTICALS, S.A., Barcelona (ES)

( * ) Notice: Subject to any disclaimer, the term of this patent is extended or adjusted under 35 U.S.C. 154(b) by 0 days.

(21) Appl. No.: 15/769,520

(22) PCT Filed: Oct. 21, 2016

(86) PCT No.: PCT/EP2016/001743
§ 371 (c)(1),
(2) Date: Apr. 19, 2018

(87) PCT Pub. No.: WO2017/067665
PCT Pub. Date: Apr. 27, 2017

(65) Prior Publication Data
US 2018/0305343 A1    Oct. 25, 2018

(30) Foreign Application Priority Data
Oct. 23, 2015  (EP) .................................... 15382524

(51) Int. Cl.
*C07D 413/04* (2006.01)
*A61P 29/00* (2006.01)

(52) U.S. Cl.
CPC ............ *C07D 413/04* (2013.01); *A61P 29/00* (2018.01)

(58) Field of Classification Search
CPC .............................. A61P 29/00; C07D 413/04
See application file for complete search history.

(56) References Cited

U.S. PATENT DOCUMENTS

| 6,114,541 A | 9/2000 | Abrecht |
| 2001/0002713 A1 | 10/2001 | Achard et al. |
| 2001/0027193 A1 | 10/2001 | Achard et al. |

FOREIGN PATENT DOCUMENTS

| EP | 1634873 | 3/2006 | |
| EP | 1847542 | 10/2007 | |
| WO | WO2006081289 | 8/2006 | |
| WO | WO2006113837 | 10/2006 | |
| WO | WO2007098961 | 9/2007 | |
| WO | WO 2008/087512 | * 7/2008 | ......... A61K 31/5375 |
| WO | WO2008/087512 | 7/2008 | |
| WO | WO2009071657 | 6/2009 | |
| WO | WO2012/125613 | 9/2012 | |
| WO | WO2013050448 | 4/2013 | |
| WO | WO2015091988 | 6/2015 | |

OTHER PUBLICATIONS

Bowen W.D. (2000) Pharmaceutica Acta Helvetiae 74: 211-218.
G. Ronsisvalle et al. Pure Appl. Chem. 73, 1499-1509 (2001).
Hanner, M. et al. Proc. Natl. Acad. Sci., 1996, 93:8072-8077.
Kaiser et al (1991) Neurotransmissions 7 (1): 1-5.
Quirion, R. et al. Trends Pharmacol. Sci., 1992, 13:85-86.
Snyder, S.H., Largent, B.L. J. Neuropsychiatry 1989, 1, 7.
Walker, J.M. et al, Pharmacological Reviews, 1990, vol. 42, No. 4, 355-402.
International Search Report from PCT/EP2016/001743 dated Jan. 12, 2017.

* cited by examiner

*Primary Examiner* — Erich A Leeser
(74) *Attorney, Agent, or Firm* — Hueschen and Sage

(57) ABSTRACT

The present invention relates to substituted morpholine derivatives having pharmacological activity towards the sigma (σ) receptor, to processes of preparation of such compounds, to pharmaceutical compositions comprising them, and to their use in therapy, in particular for the treatment of pain.

20 Claims, No Drawings

SUBSTITUTED MORPHOLINE DERIVATIVES HAVING ACTIVITY AGAINST PAIN

FIELD OF THE INVENTION

The present invention relates to new substituted morpholine derivatives having affinity for sigma receptors, especially sigma-1 ($\sigma_1$) receptors, as well as to the process for the preparation thereof, to compositions comprising them, and to their use as medicaments.

BACKGROUND OF THE INVENTION

The search for new therapeutic agents has been greatly aided in recent years by better understanding of the structure of proteins and other biomolecules associated with target diseases. One important class of these proteins are the sigma ($\sigma$) receptors, cell surface receptors of the central nervous system (CNS) which may be related to the dysphoric, hallucinogenic and cardiac stimulant effects of opioids. From studies, of the biology and function of sigma receptors, evidence has been presented that sigma receptor ligands may be useful in the treatment of psychosis and movement disorders such as dystonia and tardive dyskinesia, and motor disturbances associated with Huntington's chorea or Tourette's syndrome and in Parkinson's disease (Walker, J. M. et al, Pharmacological Reviews, 1990, 42, 355). It has been reported that the known sigma receptor ligand rimcazole clinically shows effects in the treatment of psychosis (Snyder, S. H., Largent, B. L. J. Neuropsychiatry 1989, 1, 7). The sigma binding sites have preferential affinity for the dextrorotatory isomers of certain opiate benzomorphans, such as (+)SKF-10047, (+)cyclazocine, and (+)-pentazocine and also for some narcoleptics such as haloperidol.

"The sigma receptor/s" as used in this application is/are well known and defined using the following citation: This binding site represents a typical protein different from opioid, NMDA, dopaminergic, and other known neurotransmitter or hormone receptor families (G. Ronsisvalle et al. Pure Appl. Chem. 73, 1499-1509 (2001)).

The sigma receptor has at least two subtypes, which may be discriminated by stereoselective isomers of these pharmacoactive drugs. (+)SKF-10047 has nanomolar affinity for the sigma-1 ($\sigma_1$) site, and has micromolar affinity for the sigma-2 ($\sigma_2$) site. Haloperidol has similar affinities for both subtypes.

The $\sigma_1$ receptor is a non-opiaceous type receptor expressed in numerous adult mammal tissues (e.g. central nervous system, ovary, testicle, placenta, adrenal gland, spleen, liver, kidney, gastrointestinal tract) as well as in embryo development from its earliest stages, and is apparently involved in a large number of physiological functions. Its high affinity for various pharmaceuticals has been described, such as for (+)SKF-10047, (+)-pentazocine, haloperidol and rimcazole, among others, known ligands with analgesic, anxiolytic, antidepressive, antiamnesic, antipsychotic and neuroprotective activity. $\sigma_1$ receptor is of great interest in pharmacology in view of its possible physiological role in processes related to analgesia, anxiety, addiction, amnesia, depression, schizophrenia, stress, neuroprotection and psychosis [Kaiser et al (1991) Neurotransmissions 7 (1): 1-5], [Walker, J. M. et al, Pharmacological Reviews, 1990, 42, 355] and [Bowen W. D. (2000) Pharmaceutica Acta Helvetiae 74: 211-218].

The $\sigma_2$ receptor is also expressed in numerous adult mammal tissues (e.g. nervous system, immune system, endocrine system, liver, kidney). $\sigma_2$ receptors can be components in a new apoptosis route that may play an important role in regulating cell proliferation or in cell development. This route seems to consist of $\sigma_2$ receptors joined to intracellular membranes, located in organelles storing calcium, such as the endoplasmic reticulum and mitochondria, which also have the ability to release calcium from these organelles. The calcium signals can be used in the signaling route for normal cells and/or in induction of apoptosis.

Agonists of $\sigma_2$ receptors induce, changes in cell morphology, apoptosis in several types of cell lines and regulate the expression of p-glycoprotein mRNA, so that they are potentially useful as antineoplasic agents for treatment of cancer. In fact, $\sigma_2$ receptor agonists have been observed to induce apoptosis in mammary tumour cell lines resistant to common antineoplasic agents that damage DNA. In addition, agonists of $\sigma_2$ receptors enhance the cytotoxic effects of these antineoplasic agents at concentrations in which the agonist is not cytotoxic. Thus, agonists of $\sigma_2$ receptors can be used as antineoplasic agents at doses inducing apoptosis or at sub-toxic doses in combination with other antineoplasic agents to revert the resistance to the drug, thereby allowing using lower doses of the antineoplasic agent and considerably reducing its adverse effects.

Antagonists of $\sigma_2$ receptors can prevent the irreversible motor side effects caused by typical neuroleptic agents. In fact, it has been found that antagonists of $\sigma_2$ receptors can be useful as agents for improving the weakening effects of delayed dyskinesia appearing in patients due to chronic treatment of psychosis with typical antipsychotic drugs, such as haloperidol. $\sigma_2$ receptors also seem to play a role in certain degenerative disorders in which blocking these receptors could be useful.

Endogenous sigma ligands are not known, although progesterone has been suggested to be one of them. Possible sigma-site-mediated drug effects include modulation of glutamate receptor function, neurotransmitter response, neuroprotection, behavior, and cognition (Quirion, R. et al. Trends Pharmacol. Sci., 1992, 13:85-86). Most studies have implied that sigma binding sites (receptors) are plasmalemmal elements of the signal transduction cascade. Drugs reported to be selective sigma ligands have been evaluated as antipsychotics (Hanner, M. et al. Proc. Natl. Acad. Sci., 1996, 93:8072-8077). The existence of sigma receptors in the CNS, immune and endocrine systems have suggested a likelihood that it may serve as link between the three systems.

In view of the potential therapeutic applications of agonists or antagonists of the sigma receptor, a great effort has been directed to find selective ligands. Thus, the prior art discloses different sigma receptor ligands.

For instance, the international patent application WO2007/098961 describes 4,5,6,7 tetrahydrobenzo[b]thiophene derivatives having pharmacological activity towards the sigma receptor.

Spiro[benzopyran] or spiro[benzofuran] derivatives were also disclosed in EP1847542 as well as pyrazole derivatives (EP1634873) with pharmacological activity on sigma receptors.

WO2009/071657 discloses some tricyclic triazolic compounds although structurally different to the ones of the current invention with activity towards sigma receptors.

Nevertheless, there is still a need to find compounds having pharmacological activity towards the sigma receptor, being both effective, selective, and/or having good "drugability" properties, i.e. good pharmaceutical properties related to administration, distribution, metabolism and excretion.

Surprisingly, it has been observed that the new substituted morpholine derivatives with general Formula (I) show a selective affinity for $\sigma_1$ receptor ranging from good to excellent. These compounds are therefore particularly suitable as pharmacologically active agents in medicaments for the prophylaxis and/or treatment of disorders or diseases related to Sigma receptors.

SUMMARY OF THE INVENTION

The present invention discloses novel compounds with great affinity to sigma receptors and having high solubility in a physiological media which might be used for the treatment of sigma related disorders or diseases.

As this invention is aimed at providing a compound or a chemically related series of compounds which act as ligands of the $\sigma_1$ receptor it is a very preferred embodiment if the compound has a binding expressed as $K_i$ which is preferably <1000 nM, more preferably <500 nM, even more preferably <100 nM.

The invention is directed in a main aspect to a compound of general Formula (I),

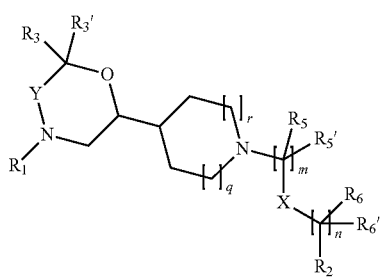

(I)

wherein $R_1$, $R_2$, $R_3$, $R_{3'}$, $R_5$, $R_{5'}$, $R_6$, $R_{6'}$, X, Y, m, n, q and r are as defined below in the detailed description.

A further object of the invention refers to the processes for preparation of compounds of general formula (I).

A still further object of the invention refers to the use of intermediate compounds for the preparation of a compound of general formula (I).

It is also an object of the invention a pharmaceutical composition comprising a compound of formula (I).

Finally, it is an object of the invention the use of compound as a medicament and more particularly for the treatment of pain and pain related conditions.

DETAILED DESCRIPTION OF THE INVENTION

The present invention discloses novel compounds with great affinity to sigma receptors and having high solubility in a physiological media which might be used for the treatment of sigma related disorders or diseases.

As this invention is aimed at providing a compound or a chemically related series of compounds which act as ligands of the $\sigma_1$ receptor it is a very preferred embodiment if the compound has a binding expressed as $K_i$ which is preferably <1000 nM, more preferably <500 nM, even more preferably <100 nM.

Advantageously, the compounds according to the present invention would in addition show one or more the following functionalities: $\sigma_1$ receptor antagonism. It has to be noted, though, that the functionalities "antagonism" and "agonism" are also sub-divided in their effect into subfunctionalities like partial agonism or inverse agonism. Accordingly, the functionalities of the compound should be considered within a relatively broad bandwidth.

An antagonist blocks or dampens agonist-mediated responses. Known subfunctionalities are neutral antagonists or inverse agonists.

An agonist increases the activity of the receptor above its basal level. Known subfunctionalities are full agonists, or partial agonists.

The invention is directed in a main aspect to a compound of general Formula (I), In a particular aspect, the present invention is directed to compounds of general Formula (I):

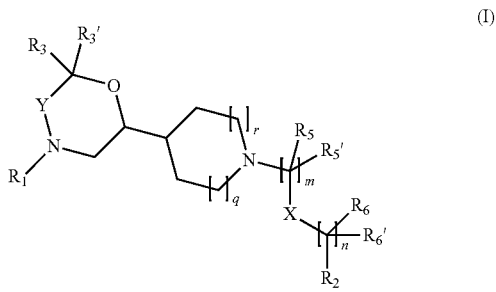

(I)

wherein
$R_1$ is

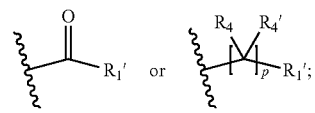

m is 1, 2, 3, 4 or 5;
n is 0, 1, 2, 3, 4 or 5;
p is 0 or 1;
q is 0, 1 or 2;
r is 0, 1 or 2;
Y is —$CH_2$— or —C(O)—;
X is a bond, —C($R_xR_{x'}$)—, —C(O)—, —O—, —C(O)NR—, —$NR_7$C(O)— or —C(O)O—;
  wherein $R_x$ is selected from halogen or substituted or unsubstituted $C_{1-6}$ alkyl, substituted or unsubstituted $C_{2-6}$ alkenyl substituted or unsubstituted $C_{2-6}$ alkynyl, and —$OR_7$;
  $R_{x'}$ is selected from hydrogen, halogen or substituted or unsubstituted $C_{1-6}$ alkyl, substituted or unsubstituted $C_{2-6}$ alkenyl and substituted or unsubstituted $C_{2-6}$ alkynyl;
  $R_7$ is selected from hydrogen, substituted or unsubstituted $C_{1-6}$ alkyl, substituted or unsubstituted $C_{2-6}$ alkenyl and substituted or unsubstituted $C_{2-6}$ alkynyl;
  $R_{1'}$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;

$R_2$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl, $R_3$ and $R_{3'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

alternatively, $R_3$ and $R_{3'}$ taken together with the connecting C-atom may form a substituted or unsubstituted cycloalkyl;

$R_4$ and $R_{4'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, —CHOR$_9$ and —C(O)OR$_9$;

wherein $R_9$ is selected from hydrogen, substituted or unsubstituted $C_{1-9}$ alkyl, substituted or unsubstituted $C_{2-9}$ alkenyl and substituted or unsubstituted $C_{2-9}$ alkynyl;

$R_5$ and $R_{5'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, —CHOR$_8$ and —C(O)OR$_8$;

wherein $R_8$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

alternatively $R_5$ and $R_{5'}$ taken together with the connecting C-atom may form a substituted or unsubstituted cycloalkyl or a substituted or unsubstituted heterocyclyl;

$R_6$ and $R_{6'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, —CHOR$_{10}$ and —C(O)OR$_{10}$;

wherein $R_{10}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

These compounds according to the invention are optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment, these compounds according to the invention are optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In a further embodiment the following proviso applies:
when Y is —C(O)—, then $R_1$ is not

[structure]

In a further embodiment the compound according to the invention of general Formula (I) is a compound of general Formula (I')

(I')
[structure]

wherein, $R_1$, $R_2$, $R_3$, $R_{3'}$, $R_5$, $R_{5'}$, X, Y, m, q and r are as defined in the description.

In a further embodiment the compound according to the invention of general Formula (I) is a compound of general Formula (I$^{2'}$)

(I$^{2'}$)
[structure]

wherein $R_1$, $R_2$, $R_3$, $R_{3'}$, $R_5$, $R_{5'}$, X, m, q and r are as defined in the description.

In a further embodiment, for compounds of general Formula (I) are compounds of general Formula (I$^{3'}$)

(I$^{3'}$)
[structure]

wherein $R_1$, $R_2$, $R_3$, $R_{3'}$, $R_5$, $R_{5'}$, X, m, q and r are as defined in the description. In a further-embodiment, for compounds of general Formula (I) are compounds of general Formula (I$^{4'}$)

(I$^{4'}$)
[structure]

wherein $R_1$, $R_2$, $R_5$, $R_{5''}$, m, q and r are as defined in the description.

In a further embodiment, for compounds of general Formula (I) are compounds of general Formula (I$^{4a'}$),

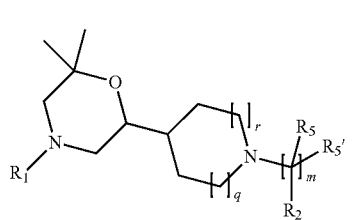
(I^{4a'})

wherein $R_1$, $R_2$, $R_5$, $R_{5'}$, m, q and r are as defined in the description.

In a further embodiment, for compounds of general Formula (I) are compounds of general Formula (I^{4b'})

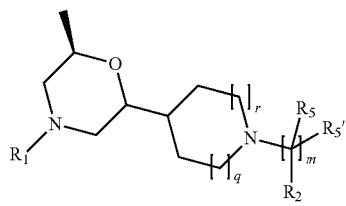
(I^{4b'})

wherein $R_1$, $R_2$, $R_5$, $R_{5'}$, m, q and r are as defined in the description.

In a further embodiment, for compounds of general Formula (I) are compounds of general Formula (I^{4c'})

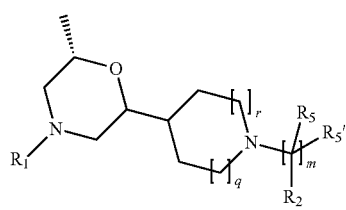
(I^{4c'})

wherein $R_1$, $R_2$, $R_5$, $R_{5'}$, m, q and r are as defined in the description.

In a further embodiment, for compounds of general Formula (I) are compounds of general Formula (I^{5'})

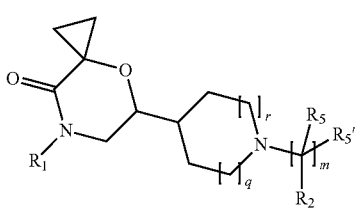
(I^{5'})

wherein $R_1$, $R_2$, $R_5$, $R_{5'}$, m, q and r are as defined in the description.

In a further embodiment, for compounds of general Formula (I) are compounds of general Formula (I^{5a'})

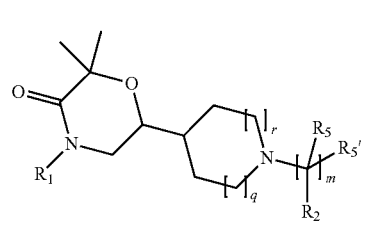
(I^{5a'})

wherein $R_1$, $R_2$, $R_5$, $R_{5'}$, m, q and r are as defined in the description.

In a further embodiment, for compounds of general Formula (I) are compounds of general Formula (I^{5b'})

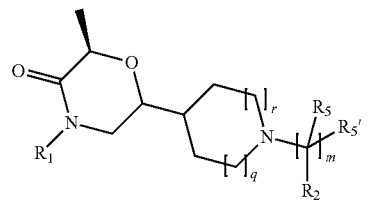
(I^{5b'})

wherein $R_1$, $R_2$, $R_5$, $R_{5'}$, m, q and r are as defined in the description.

In a further embodiment, for compounds of general Formula (I) are compounds of general Formula (I^{5c'})

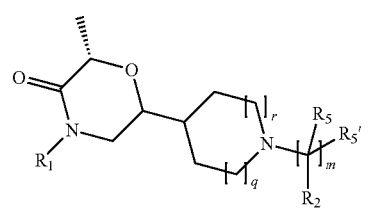
(I^{5c'})

wherein $R_1$, $R_2$, $R_5$, $R_{5'}$, m, q and rare as defined in the description.

In a further embodiment, for compounds of general Formula (I) are compounds of general Formula (I^{6'})

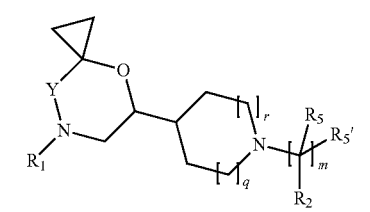
(I^{6'})

wherein $R_1$, $R_2$, $R_5$, $R_{5'}$, Y, m, q and r are as defined in the description.

In a further embodiment, for compounds of general Formula (I) are compounds of general Formula (I^{6a'})

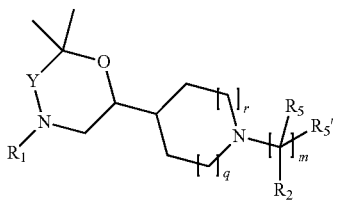

(I^{6a'})

wherein $R_1$, $R_2$, $R_5$, $R_{5'}$, Y, m, q and r are as defined in the description.

In a further embodiment, for compounds of general Formula (I) are compounds of general Formula (I^{6b'})

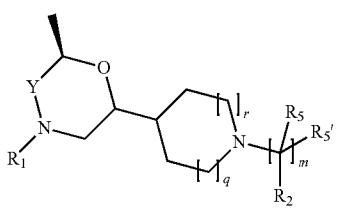

(I^{6b'})

wherein $R_1$, $R_2$, $R_5$, $R_{5'}$, Y, m, q and r are as defined in the description.

In a further embodiment, for compounds of general Formula (I) are compounds of general Formula (I^{6c'})

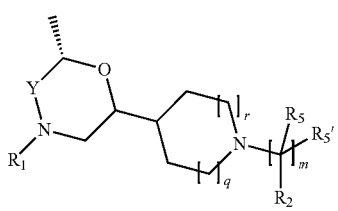

(I^{6c'})

wherein $R_1$, $R_2$, $R_5$, $R_{5'}$, Y, m, q and r are as defined in the description.

For clarity purposes, reference is also made to the following statements below in the definitions of substitutions on alkyl etc. or aryl etc. that "wherein when different radicals $R_1$ to $R_{14''''}$ and $R_x$, $R_{x'}$ are present simultaneously in Formula I they may be identical or different". This statement is reflected in the below general Formula (I^{7'}) being derived from and falling into general Formula (I') as well as Formula (I).

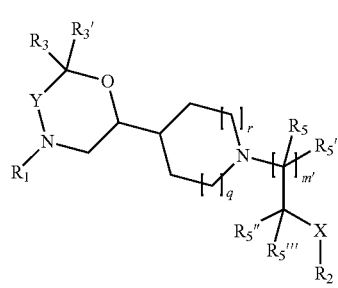

(I^{7'})

wherein $R_1$, $R_2$, $R_3$, $R_{3'}$, $R_5$, $R_{5'}$, X, Y, q and r are as defined in the description. In addition, m' (being 0 or 1), $R_{5''}$ and $R_{5'''}$ are added. As said above, this statement is thus reflected in that $R_{5''}$ and $R_{5'''}$ are or could be different from $R_5$ and $R_{5'}$ or not and—accordingly—m' being 0 or 1 is naturally resulting from m (in general Formula (I) or (I') being 1 or 2).

The same would be applicable mutatis mutandis for general Formulas like general Formula (I) as well as the other general Formulas (I') to (I^{6c'}) above as well as to all the intermediates of synthesis.

For clarity purposes, all groups and definitions described in the description and referring to compounds of general Formula (I), also apply to compounds of general Formula (I'), (I^{2'}), (I^{3'}), (I^{4'}), (I^{5'}), (I^{6'}), (I^{4a'}), (I^{5a'}), (I^{6a'}), (I^{4b'}), (I^{5b'}), (I^{6b'}) (I^{4c'}), (I^{5c'}) (I^{6c'}) and also (I^{7'}), as well as to all the intermediates of synthesis, when those groups are present in the mentioned general Markush formulae, since compounds of general Formula (I'), (I^{2'}), (I^{3'}), (I^{4'}), (I^{5'}), (I^{6'}), (I^{4a'}), (I^{5a'}), (I^{6a'}), (I^{4b'}), (I^{5b'}), (I^{6b'}) (I^{4c'}), (I^{5c'}) (I^{6c'}) or (I^{7'}) are included in the general Formula (I).

For clarity purposes, the general Markush Formula (I)

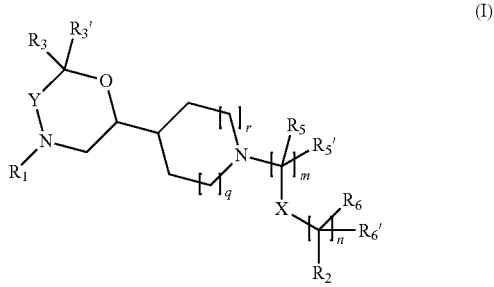

(I)

is equivalent to

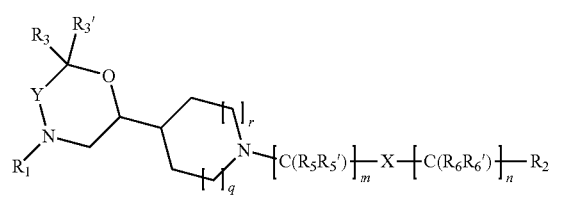

(IZ)

wherein only —C($R_5R_{5'}$)— and —C($R_6R_{6'}$)— are included into the brackets and m and n mean the number of times that —C($R_5R_{5'}$)— and —C($R_6R_{6'}$)— are repeated, respectively. The same would apply to general Markush Formulae (I'), (I^{2'}), (I^{3'}), (I^{4'}), (I^{5'}), (I^{6'}), (I^{4a'}), (I^{5a'}), (I^{6a'}), (I^{4b'}), (I^{5b'}), (I^{6b'}) (I^{4c'}), (I^{5c'}) (I^{6c'}) or (I^{7'}) and also to all the intermediates of synthesis.

In addition, and for clarity purposes, it should further be understood that naturally if m or n are 0, then X or $R_2$ are still present in general Markush Formulae (I'), (I^{2'}), (I^{3'}), (I^{4'}), (I^{5'}), (I^{6'}), (I^{4a'}), (I^{5a'}), (I^{6a'}), (I^{4b'}), (I^{5b'}), (I^{6b'}) (I^{4c'}), (I^{5c'}) (I^{6c'}) or (I^{7'}) and to all the intermediates of synthesis.

In the context of this invention, alkyl is understood as meaning saturated, linear or branched hydrocarbons, which may be unsubstituted or substituted once or several times. It encompasses e.g. —CH$_3$ and —CH$_2$—CH$_3$. In these radicals, $C_{1-2}$-alkyl represents C1- or C2-alkyl, $C_{1-3}$-alkyl represents C1-, C2- or C3-alkyl, $C_{1-4}$-alkyl represents C1-, C2-, C3- or C4-alkyl, $C_{1-5}$-alkyl represents C1-, C2-, C3-, C4-, or C5-alkyl, $C_{1-6}$-alkyl represents C1-, C2-, C3-, C4-, C5- or C6-alkyl, $C_{1-7}$-alkyl represents C1-, C2-, C3-, C4-, C5-, C6- or C7-alkyl, $C_{1-8}$-alkyl represents C1-, C2-, C3-, C4-, C5-, C6-, C7- or C8-alkyl, $C_{1-10}$-alkyl represents C1-, C2-, C3-, C4-, C5-, C6-, C7-, C8-, C9- or C10-alkyl and $C_{1-18}$-alkyl represents C1-, C2-, C3-, C4-, C5-, C6-, C7-, C8-, C9-, C10-, C11-, C12-, C13-, C14-, C15-, C16-, C17- or C18-alkyl. The alkyl radicals are preferably methyl, ethyl, propyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, if substituted also $CHF_2$, $CF_3$ or $CH_2OH$ etc. Preferably alkyl is understood in the context of this invention as $C_{1-6}$alkyl like methyl, ethyl, propyl, butyl, pentyl, hexyl, heptyl, or octyl; preferably is $C_{1-6}$alkyl like methyl, ethyl, propyl, butyl, pentyl, or hexyl; more preferably is $C_{1-4}$alkyl like methyl, ethyl, propyl or butyl.

Alkenyl is understood as meaning unsaturated, linear or branched hydrocarbons, which may be unsubstituted or substituted once or several times. It encompasses groups like e.g. —CH=CH—$CH_3$. The alkenyl radicals are preferably vinyl (ethenyl), allyl (2-propenyl). Preferably in the context of this invention alkenyl is $C_{2-10}$-alkenyl or $C_{2-8}$-alkenyl like ethylene, propylene, butylene, pentylene, hexylene, heptylene or octylene; or is $C_{2-6}$-alkenyl like ethylene, propylene, butylene, pentylene, or hexylene; or is $C_{2-4}$-alkenyl, like ethylene, propylene, or butylenes.

Alkynyl is understood as meaning unsaturated, linear or branched hydrocarbons, which may be unsubstituted or substituted once or several times. It encompasses groups like e.g. —C≡C—$CH_3$ (1-propinyl). Preferably alkynyl in the context of this invention is $C_{2-10}$-alkynyl or $C_{2-8}$-alkynyl like ethyne, propyne, butyene, pentyne, hexyne, heptyne, or octyne; or is $C_{2-6}$-alkynyl like ethyne, propyne, butyene, pentyne, or hexyne; or is $C_{2-4}$-alkynyl like ethyne, propyne, butyene, pentyne, or hexyne.

In connection with alkyl (also in alkylaryl, alkylheterocyclyl or alkylcycloalkyl), alkenyl, alkynyl and O-alkyl—unless defined otherwise—the term substituted in the context of this invention is understood as meaning replacement of at least one hydrogen radical on a carbon atom by halogen (F, Cl, Br, I), —$NR_cR_{c'''}$, —$SR_c$, —$S(O)R_c$, —$S(O)_2R_c$, —$OR_c$, —$C(O)OR_c$, —CN, —$C(O)NR_cR_{c'}$, haloalkyl, haloalkoxy or —$OC_{1-6}$alkyl, being $R_c$ represented by $R_{11}$, $R_{12}$, $R_{13}$, (being $R_{c'}$ represented by $R_{11'}$, $R_{12'}$, $R_{13'}$; being $R_{c''}$ represented by $R_{11''}$, $R_{12''}$, $R_{13''}$; being $R_{c'''}$ represented by $R_{11'''}$, $R_{12'''}$, $R_{13'''}$, being $R_{c''''}$ represented by $R_{11''''}$, $R_{12''''}$, $R_{13''''}$) wherein $R_1$ to $R_{14''''}$ and $R_x$ and $R_{x'}$ are as defined in the description, and wherein when different radicals $R_1$ to $R_{14''''}$ and $R_x$ and $R_{x'}$ are present simultaneously in Formula I they may be identical or different.

Most preferably in connection with alkyl (also in alkylaryl, alkylheterocyclyl or alkylcycloalkyl), alkenyl, alkynyl or O-alkyl, substituted is understood in the context of this invention that any alkyl (also in, alkylaryl, alkylheterocyclyl or alkylcycloalkyl), alkenyl, alkynyl or O-alkyl which is substituted is substituted with one or more of halogen (F, Cl, Br, I), —$OR_c$, —CN, —$NR_cR_{c'''}$, haloalkyl, haloalkoxy or —$OC_{1-6}$alkyl, being $R_c$ represented by $R_{11}$, $R_{12}$, $R_{13}$, (being $R_{c'}$ represented by $R_{11'}$, $R_{12'}$, $R_{13'}$; being $R_{c''}$ represented by $R_{11''}$, $R_{12''}$, $R_{13''}$; being $R_{c'''}$ represented by $R_{11'''}$, $R_{12'''}$, $R_{13'''}$, being $R_{c''''}$ represented by $R_{11''''}$, $R_{12''''}$, $R_{13''''}$), wherein $R_1$ to $R_{14''''}$ and $R_x$ and $R_{x'}$ are as defined in the description, and wherein when different radicals $R_1$ to $R_{14''''}$ and $R_x$ and $R_{x'}$ are present simultaneously in Formula I, they may be identical or different.

More than one replacement on the same molecule and also on the same carbon atom is possible with the same or different substituents. This includes for example 3 hydrogens being replaced on the same C atom, as in the case of $CF_3$, or at different places of the same molecule, as in the case of e.g. —CH(OH)—CH=CH—$CHCl_2$.

In the context of this invention haloalkyl is understood as meaning an alkyl being substituted once or several times by a halogen (selected from F, Cl, Br, I). It encompasses e.g. —$CH_2Cl$, —$CH_2F$, —$CHCl_2$, —$CHF_2$, —$CCl_3$, —$CF_3$ and —$CH_2$—$CHCl_2$. Preferably haloalkyl is understood in the context of this invention as halogen-substituted $C_{1-4}$-alkyl representing halogen substituted C1-, C2-, C3- or C4-alkyl. The halogen-substituted alkyl radicals are thus preferably methyl, ethyl, propyl, and butyl. Preferred examples include —$CH_2Cl$, —$CH_2F$, —$CHCl_2$, —$CHF_2$, and —$CF_3$.

In the context of this invention haloalkoxy is understood as meaning an —O— alkyl being substituted once or several times by a halogen (selected from F, Cl, Br, I). It encompasses e.g. —$OCH_2Cl$, —$OCH_2F$, —$OCHCl_2$, —$OCHF_2$, —$OCCl_3$, —$OCF_3$ and —$OCH_2$—$CHCl_2$. Preferably haloalkyl is understood in the context of this invention as halogen-substituted —$OC_{1-4}$-alkyl representing halogen substituted C1-, C2-; C3- or C4-alkoxy. The halogen-substituted alkyl radicals are thus preferably O-methyl, O-ethyl, O-propyl, and O-butyl. Preferred examples include —$OCH_2Cl$, —$OCH_2F$, —$OCHCl_2$, —$OCHF_2$, and —$OCF_3$.

In the context of this invention cycloalkyl is understood as meaning saturated and unsaturated (but not aromatic) cyclic hydrocarbons (without a heteroatom in the ring), which can be unsubstituted or once or several times substituted. Furthermore, $C_{3-4}$-cycloalkyl represents C3- or C4-cycloalkyl, $C_{3-5}$-cycloalkyl represents C3-, C4- or C5-cycloalkyl, $C_{3-6}$-cycloalkyl represents C3-, C4-, C5- or C6-cycloalkyl, $C_{3-7}$-cycloalkyl represents C3-, C4-, C5-, C6- or C7-cycloalkyl, $C_{3-8}$-cycloalkyl represents C3-, C4-, C5-, C6-, C7- or C8-cycloalkyl, $C_{4-5}$-cycloalkyl represents C4- or C5-cycloalkyl, $C_{4-6}$-cycloalkyl represents C4-, C5- or C6-cycloalkyl, $C_{4-7}$-cycloalkyl represents C4-, C5-, C6- or C7-cycloalkyl, $C_{5-6}$-cycloalkyl represents C5- or C6-cycloalkyl and $C_{5-7}$-cycloalkyl represents C5-, C6- or C7-cycloalkyl. Examples are cyclopropyl, 2-methylcyclopropyl, cyclopropylmethyl, cyclobutyl, cyclopentyl, cyclopentylmethyl, cyclohexyl, cycloheptyl, cyclooctyl, and also adamantly. Preferably in the context of this invention cycloalkyl is $C_{3-8}$cycloalkyl like cyclopropyl, cyclobutyl, cyclopentyl, cyclohexyl, cycloheptyl, or cyclooctyl; or is $C_{3-7}$cycloalkyl like cyclopropyl, cyclobutyl, cyclopentyl, cyclohexyl, or cycloheptyl; or is $C_{3-6}$cycloalkyl like cyclopropyl, cyclobutyl, cyclopentyl or cyclohexyl, especially cyclopentyl or cyclohexyl.

Aryl is understood as meaning 5 to 18 membered mono or polycyclic ring systems with at least one aromatic ring but without heteroatoms even in only one of the rings. Examples are phenyl, naphthyl, fluoranthenyl, fluorenyl, tetralinyl or indanyl, 9H-fluorenyl or anthracenyl radicals, which can be unsubstituted or once or several times substituted. Most preferably aryl is understood in the context of this invention as phenyl, naphtyl or anthracenyl, preferably is phenyl.

A heterocyclyl radical or group (also called heterocyclyl hereinafter) is understood as meaning 5 to 18 membered mono or polycyclic heterocyclic ring systems, with at least one saturated or unsaturated ring which contains one or more heteroatoms from the group consisting of nitrogen; oxygen and/or sulfur in the ring. A heterocyclic group can also be substituted once or several times.

Examples include non-aromatic heterocyclyls such as tetrahydropyrane, oxazepane, morpholine, piperidine, pyrrolidine as well as heteroaryls such as furan, benzofuran, thiophene, benzothiophene, pyrrole, pyridine, pyrimidine, pyrazine, quinoline, isoquinoline, phthalazine, thiazole, benzothiazole, indole, benzotriazole, carbazole and quinazoline.

Subgroups inside the heterocyclyls as understood herein include heteroaryls and non-aromatic heterocyclyls.

- the heteroaryl (being equivalent to heteroaromatic radicals or aromatic heterocyclyls) is an aromatic 5 to 18 membered mono or polycyclic heterocyclic ring system of one or more rings of which at least one aromatic ring contains one or more heteroatoms from the group consisting of nitrogen, oxygen and/or sulfur in the ring; preferably is an aromatic 5 to 18 membered mono or polycyclic heterocyclic ring system of one or two rings of which at least one aromatic ring contains one or more heteroatoms from the group consisting of nitrogen, oxygen and/or sulfur in the ring, more preferably is selected from furan, benzofuran, thiophene, benzothiophene, pyrrole, pyridine, pyrimidine, pyrazine, quinoline, isoquinoline, phthalazine, benzothiazole, indole, benzotriazole, carbazole, quinazoline, thiazole, imidazole, pyrazole, oxazole, thiophene and benzimidazole;
- the non-aromatic heterocyclyl is a 5 to 18 membered mono or polycyclic heterocyclic ring system of one or more rings of which at least one ring—with this (or these) ring(s) then not being aromatic—contains one or more heteroatoms from the group consisting of nitrogen, oxygen and/or sulfur in the ring; preferably is a 5 to 18 membered mono or polycyclic heterocyclic ring system of one or two rings of which one or both rings—with this one or two rings then not being aromatic—contain/s one or more heteroatoms from the group consisting of nitrogen, oxygen and/or sulfur in the ring, more preferably is selected from oxazepam, pyrrolidine, piperidine, piperazine, tetrahydropyran, morpholine, indoline, oxopyrrolidine, benzodioxane, oxetane, especially is benzodioxane, morpholine, tetrahydropyran, piperidine, oxopyrrolidine, oxetane and pyrrolidine.

Preferably in the context of this invention heterocyclyl is defined as a 5 to 18 membered mono or polycyclic heterocyclic ring system of one or more saturated or unsaturated rings of which at least one ring contains one or more heteroatoms from the group consisting of nitrogen, oxygen and/or sulfur in the ring. Preferably it is a 5 to 18 membered mono or polycyclic heterocyclic ring system of one or two saturated or unsaturated rings of which at least one ring contains one or more heteroatoms from the group consisting of nitrogen, oxygen and/or sulfur in the ring.

Preferred examples of heterocyclyls include oxetane, oxazepan, pyrrolidine, imidazole, oxadiazole, tetrazole, pyridine, pyrimidine, piperidine, piperazine, benzofuran, benzimidazole, indazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole, oxopyrrolidine, pyrimidine, benzodioxolane, benzodioxane, carbazole and quinazoline, especially is pyridine, pyrazine, indazole, benzodioxane, thiazole, benzothiazole, morpholine, tetrahydropyrane, pyrazole, imidazole, piperidine, thiophene, indole, benzimidazole, pyrrolo[2,3b]pyridine, benzoxazole, oxopyrrolidine, pyrimidine, oxazepane, oxetane and pyrrolidine; In the context of this invention oxopyrrolidine is understood as meaning pyrrolidin-2-one.

In connection with aromatic heterocyclyls (heteroaryls), non-aromatic heterocyclyls, aryls and cycloalkyls, when a ring system falls within two or more of the above cycle definitions simultaneously, then the ring system is defined first as an aromatic heterocyclyl (heteroaryl) if at least one aromatic ring contains a heteroatom. If no aromatic ring contains a heteroatom, then the ring system is defined as a non-aromatic heterocyclyl if at least one non-aromatic ring contains a heteroatom. If no non-aromatic ring contains a heteroatom, then the ring system is defined as an aryl if it contains at least one aryl cycle. If no aryl is present, then the ring system is defined as a cycloalkyl if at least one non-aromatic cyclic hydrocarbon is present.

In the context of this invention alkylaryl is understood as meaning an aryl group (see above) being connected to another atom through a $C_{1-6}$-alkyl (see above) which may be branched or linear and is unsubstituted or substituted once or several times. Preferably alkylaryl is understood as meaning an aryl group (see above) being connected to another atom through 1 to 4 (—$CH_2$—) groups. Most preferably alkylaryl is benzyl (i.e. —$CH_2$-phenyl).

In the context of this invention alkylheterocyclyl is understood as meaning an heterocyclyl group being connected to another atom through a $C_{1-6}$-alkyl (see above) which may be branched or linear and is unsubstituted or substituted once or several times. Preferably alkylheterocyclyl is understood as meaning an heterocyclyl group (see above) being connected to another atom through 1 to 4 (—$CH_2$—) groups. Most preferably alkylheterocyclyl is —$CH_2$-pyridine.

In the context of this invention alkylcycloalkyl is understood as meaning an cycloalkyl group being connected to another atom through a $C_{1-6}$-alkyl (see above) which may be branched or linear and is unsubstituted or substituted once or several times. Preferably alkylcycloalkyl is understood as meaning an cycloalkyl group (see above) being connected to another atom through 1 to 4 (—$CH_2$—) groups. Most preferably alkylcycloalkyl is —$CH_2$-cyclopropyl.

Preferably, the aryl is a monocyclic aryl. More preferably the aryl is a 5, 6 or 7 membered monocyclic aryl. Even more preferably the aryl is a 5 or 6 membered monocyclic aryl.

Preferably, the heteroaryl is a monocyclic heteroaryl. More preferably the heteroaryl is a 5, 6 or 7 membered monocyclic heteroaryl. Even more preferably the heteroaryl is a 5 or 6 membered monocyclic heteroaryl.

Preferably, the non-aromatic heterocyclyl is a monocyclic non-aromatic heterocyclyl. More preferably the non-aromatic heterocyclyl is a 4, 5, 6 or 7 membered monocyclic non-aromatic heterocyclyl. Even more preferably the non-aromatic heterocyclyl is a 5 or 6 membered monocyclic non-aromatic heterocyclyl.

Preferably, the cycloalkyl is a monocyclic cycloalkyl. More preferably the cycloalkyl is a 3, 4, 5, 6, 7 or 8 membered monocyclic cycloalkyl. Even more preferably the cycloalkyl is a 3, 4, 5 or 6 membered monocyclic cycloalkyl.

In connection with aryl (including alkyl-aryl), cycloalkyl (including alkyl-cycloalkyl), or heterocyclyl (including alkyl-heterocyclyl), substituted is understood—unless defined otherwise—as meaning substitution of the ring-system of the aryl or alkyl-aryl, cycloalkyl or alkyl-cycloalkyl; heterocyclyl or alkyl-heterocyclyl with one or more of halogen (F, Cl, Br, I), —$R_c$, —$OR_c$, —CN, —$NO_2$, —$NR_cR_{c'''}$, —$C(O)OR_c$, $NR_cC(O)R_{c'}$, —$C(O)NR_cR_{c'}$, —$NR_cS(O)_2R_{c'}$, =O, —$OCH_2CH_2OH$, —$NR_cC(O)NR_cR_{c'''}$, —$S(O)_2NR_cR_{c'}$, —$NR_cS(O)_2NR_cR_{c'''}$, haloalkyl, haloalkoxy, —$SR_c$, —$S(O)R_c$, —$S(O)_2R_c$ or $C(CH_3)OR_c$; $NR_cR_{c'''}$, with $R_c$, $R_{c'}$, $R_{c''}$ and $R_{c'''}$ independently being either H or a saturated or unsaturated, linear or branched, substituted or unsubstituted $C_{1-6}$-alkyl; a saturated or unsaturated, linear or branched, substituted or unsubstituted $C_{1-6}$-alkyl; a saturated or unsaturated, linear or branched, substituted or unsubstituted —O—$C_{1-6}$-alkyl (alkoxy); a saturated or unsaturated, linear or branched, substituted or unsubstituted —S—$C_{1-6}$-alkyl; a saturated or unsaturated, linear or branched, substituted or unsubstituted —C(O)—$C_{1-6}$-alkyl-group; a saturated or unsaturated, linear or branched, substituted or unsubstituted —C(O)—O—$C_{1-6}$-alkyl-group; a substituted or unsubstituted aryl or alkyl-aryl; a substituted or unsubstituted cycloalkyl or alkyl-cycloalkyl; a substituted or unsubstituted heterocyclyl or alkyl-heterocyclyl, being $R_c$ one of $R_{11}$, $R_{12}$ or $R_{14}$, (being $R_{c'}$ one of $R_{11'}$, $R_{12'}$ or $R_{14'}$; being $R_{c''}$ one of $R_{11''}$, $R_{12''}$ or $R_{14''}$; being $R_{c'''}$ one of $R_{11'''}$, $R_{12'''}$ or $R_{14'''}$; being $R_{c''''}$ one of $R_{11''''}$, $R_{12''''}$ or $R_{14''''}$), wherein $R_1$ to $R_{14''''}$ and $R_x$ and $R_{x'}$ are as defined in the description, and wherein when different radicals $R_1$ to $R_{14''''}$ and $R_x$ and $R_{x'}$ are present simultaneously in Formula I they may be identical or different.

Most preferably in connection with aryl (including alkyl-aryl), cycloalkyl (including alkyl-cycloalkyl), or heterocyclyl (including alkyl-heterocyclyl), substituted is understood in the context of this invention that any aryl, cycloalkyl and heterocyclyl which is substituted is substituted (also in an alkylaryl, alkylcycloalkyl or alkylheterocyclyl) with one or more of halogen (F, Cl, Br, I), —$R_c$, —$OR_c$, —CN, —$NO_2$, —$NR_cR_{c'''}$, $NR_cC(O)R_{c'}$, —$NR_cS(O)_2R_{c'}$, =O, haloalkyl, haloalkoxy, or $C(CH_3)OR_c$; —$OC_{1-4}$alkyl being unsubstituted or substituted with one or more of $OR_c$ or halogen (F, Cl, I, Br), —CN, or —$C_{1-4}$ alkyl being unsubstituted or substituted with one or more of $OR_c$ or halogen (F, Cl, I, Br), being $R_c$ one of $R_{11}$, $R_{12}$ or $R_{14}$, (being $R_{c'}$ one of $R_{11'}$, $R_{12'}$ or $R_{14'}$; being $R_{c''}$ one of $R_{11''}$, $R_{12''}$ or $R_{14''}$; being $R_{c'''}$ one of $R_{11'''}$, $R_{12'''}$ or $R_{14'''}$; being $R_{c''''}$ one of $R_{11''''}$, $R_{12''''}$ or $R_{14''''}$), wherein $R_1$ to $R_{14''''}$ and $R_x$ and $R_{x'}$ are as defined in the description, and wherein when different radicals $R_1$ to $R_{14''''}$ and $R_x$ and $R_{x'}$ are present simultaneously in Formula I they may be identical or different.

Additionally to the above-mentioned substitutions, in connection with cycloalkyl (including alkyl-cycloalkyl), or heterocycly (including alkylheterocyclyl) namely non-aromatic heterocyclyl (including non-aromatic alkyl-heterocyclyl), substituted is also understood—unless defined otherwise—as meaning substitution of the ring-system of the cycloalkyl or alkyl-cycloalkyl; non-aromatic heterocyclyl or non aromatic alkyl-heterocyclyl with

or =O.

In connection with cycloalkyl (including alkyl-cycloalkyl), or heterocycly (including alkylheterocyclyl) namely non-aromatic heterocyclyl (including non-aromatic alkyl-heterocyclyl), substituted is also understood—unless defined otherwise—as meaning substitution of the ring-system of the cycloalkyl or alkyl-cycloalkyl; non-aromatic heterocyclyl or non aromatic alkyl-heterocyclyl with

(leading to a spiro structure) or with =O.

A ring system is a system consisting of at least one ring of connected atoms but including also systems in which two or more rings of connected atoms are joined with "joined" meaning that the respective rings are sharing one (like a spiro structure), two or more atoms being a member or members of both joined rings.

The term "leaving group" means a molecular fragment that departs with a pair of electrons in heterolytic bond cleavage. Leaving groups can be anions or neutral molecules. Common anionic leaving groups are halides such as Cl—, Br—, and I—, and sulfonate esters, such as tosylate (TsO—) or mesylate.

The term "salt" is to be understood as meaning any form of the active compound used according to the invention in which it assumes an ionic form or is charged and is coupled with a counter-ion (a cation or anion) or is in solution. By this are also to be understood complexes of the active compound with other molecules and ions, in particular complexes via ionic interactions.

The term "physiologically acceptable salt" means in the context of this invention any salt that is physiologically tolerated (most of the time meaning not being toxic—especially not caused by the counter-ion) if used appropriately for a treatment especially if used on or applied to humans and/or mammals.

These physiologically acceptable salts can be formed with cations or bases and in the context of this invention is understood as meaning salts of at least one of the compounds used according to the invention—usually a (deprotonated) acid—as an anion with at least one, preferably inorganic, cation which is physiologically tolerated—especially if used on humans and/or mammals. The salts of the alkali metals and alkaline earth metals are particularly preferred, and also those with $NH_4$, but in particular (mono)- or (di)sodium, (mono)- or (di)potassium, magnesium or calcium salts.

Physiologically acceptable, salts can also be formed with anions or acids and in the context of this invention is understood as meaning salts of at least one of the compounds used according to the invention as the cation with at least one anion which are physiologically tolerated—especially if used on humans and/or mammals. By this is understood in particular, in the context of this invention, the salt formed with a physiologically tolerated acid, that is to say salts of the particular active compound with inorganic or organic acids which are physiologically tolerated—especially if used on humans and/or mammals. Examples of physiologically tolerated salts of particular acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid or citric acid.

The compounds of the invention may be present in crystalline form or in the form of free compounds like a free base or acid.

Any compound that is a solvate of a compound according to the invention like a compound according to general formula I defined above is understood to be also covered by the scope of the invention. Methods of solvation are generally known within the art. Suitable solvates are pharmaceutically acceptable solvates. The term "solvate" according to this invention is to be understood as meaning any form of the active compound according to the invention in which this compound has attached to it via non-covalent binding another molecule (most likely a polar solvent). Especially preferred examples include hydrates and alcoholates, like methanolates or ethanolates.

Any compound that is a prodrug of a compound according to the invention like a compound according to general formula I defined above is understood to be also covered by the scope of the invention. The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the present compounds: esters, amino acid esters, phosphate esters, metal salts sulfonate esters, carbamates, and amides. Examples of well known methods of producing a prodrug of a given acting compound are known to those skilled in the art and can be found e.g. in Krogsgaard-Larsen et al. "Textbook of Drug design and Discovery" Taylor & Francis (April 2002). Any compound that is a N-oxide of a compound according to the invention like a compound according to general formula I defined above is understood to be also covered by the scope of the invention.

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon or of a nitrogen by $^{15}N$-enriched nitrogen are within the scope of this invention.

The compounds of formula (I) as well as their salts or solvates of the compounds are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts. This applies also to its solvates or prodrugs.

In a further embodiment the compound according to the invention of general Formula (I)

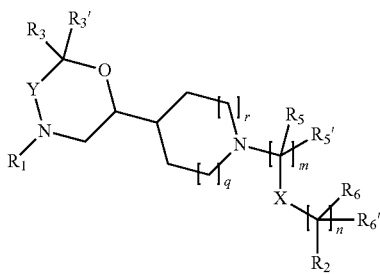

is a compound wherein
wherein
$R_1$ is

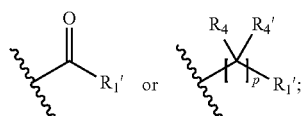

m is 1, 2, 3, 4 or 5;
n is 0, 1, 2, 3, 4 or 5;
p is 0 or 1;
q is 0, 1 or 2;
r is 0, 1 or 2;
Y is —$CH_2$— or —C(O)—;
X is a bond, —C($R_xR_{x'}$)—, —C(O)—, —O—, —C(O)N$R_7$—, —N$R_7$C(O)— or —C(O)O—;
  wherein $R_x$ is selected from halogen or substituted or unsubstituted $C_{1-6}$ alkyl, substituted or unsubstituted $C_{2-6}$ alkenyl substituted or unsubstituted $C_{2-6}$alkynyl, and —O$R_7$;
  $R_{x'}$ is selected from hydrogen, halogen or substituted or unsubstituted $C_{1-6}$ alkyl, substituted or unsubstituted $C_{2-6}$ alkenyl and substituted or unsubstituted $C_{2-6}$ alkynyl;
  $R_7$ is selected from hydrogen, substituted or unsubstituted $C_{1-6}$ alkyl, substituted or unsubstituted $C_{2-6}$ alkenyl and substituted or unsubstituted $C_{2-6}$ alkynyl;
$R_{1'}$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;
  wherein said cycloalkyl, aryl or heterocyclyl in $R_{1'}$ if substituted, is substituted with one or more substituent/s selected from halogen, —$R_{11}$, —O$R_{11}$, —$NR_2$, —$NR_{11}R_{11'''}$, $NR_{11}C(O)R_{11'}$, —$NR_{11}S(O)_2R_{11'}$, —$S(O)_2NR_{11}R_{11'}$, —$NR_{11}C(O)NR_{11'}R_{11''}$, —$SR_{11}$, —$S(O)R_{11}$, $S(O)_2R_{11}$, —CN, haloalkyl, haloalkoxy, —$C(O)OR_{11}$, —$C(O)NR_{11}R_{11'}$, —$OCH_2CH_2OH$, —$NR_{11}S(O)_2NR_{11'}R_{11''}$ and $C(CH_3)_2OR_{11}$;
additionally, the cycloalkyl or non-aromatic heterocyclyl in $R_{1'}$, if substituted, may also be substituted with

or =O;
  wherein the alkyl, alkenyl or alkynyl in $R_{1'}$, if substituted, is substituted with one or more substituent/s selected from —$OR_{11}$, halogen, —CN, haloalkyl, haloalkoxy and —$NR_{11}R_{11'''}$;
  wherein $R_{11}$, $R_{11'}$ and $R_{11''}$ are independently selected from hydrogen, unsubstituted $C_{1-6}$ alkyl, unsubstituted $C_{2-6}$ alkenyl and unsubstituted $C_{2-6}$ alkynyl;
  and wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc;
$R_2$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl,
  wherein said cycloalkyl, aryl or heterocyclyl in $R_2$, if substituted, is substituted with one or more substituent/s selected from halogen, —$R_{12}$, —$OR_{12}$, —$NR_2$, —$NR_{12}R_{12'''}$, $NR_{12}C(O)R_{12'}$, —$NR_{12}S(O)_2R_{12'}$, —$S(O)_2NR_{12}R_{12'}$, —$NR_{12}C(O)NR_{12'}R_{12''}$, —$SR_{12}$, —$S(O)R_{12}$, $S(O)_2R_{12}$, —CN, haloalkyl, haloalkoxy, —$C(O)OR_{12}$, —$C(O)NR_{12}R_{12'}$, —$OCH_2CH_2OH$, —$NR_{12}S(O)_2NR_{12'}R_{12''}$ and $C(CH_3)_2OR_{12}$;
additionally, the cycloalkyl or non-aromatic heterocyclyl in $R_2$, if substituted, may also be substituted with

 or =O;

wherein the alkyl, alkenyl or alkynyl in $R_2$, if substituted, is substituted with one or more substituent/s selected from $-OR_{12}$, halogen, $-CN$, haloalkyl, haloalkoxy and $-NR_{12}R_{12'''}$;

wherein $R_{12}$, $R_{12'}$ and $R_{12''}$ are independently selected from hydrogen, unsubstituted $C_{1-6}$ alkyl, unsubstituted $C_{2-6}$ alkenyl and unsubstituted $C_{2-6}$ alkynyl;

and wherein $R_{12'''}$ is selected from hydrogen, unsubstituted $C_{1-6}$ alkyl, unsubstituted $C_{2-6}$ alkenyl, unsubstituted $C_{2-6}$ alkynyl and -Boc;

$R_3$ and $R_{3'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

alternatively, $R_3$ and $R_{3'}$ taken together with the connecting C-atom may form a substituted or unsubstituted cycloalkyl;

$R_4$ and $R_{4'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, $-CHOR_9$ and $-C(O)OR_9$;

wherein $R_9$ is selected from hydrogen, substituted or unsubstituted $C_{1-9}$ alkyl, substituted or unsubstituted $C_{2-9}$ alkenyl and substituted or unsubstituted $C_{2-9}$ alkynyl;

$R_5$ and $R_{5'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, $-CHOR_8$ and $-C(O)OR_8$;

wherein $R_8$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

alternatively $R_5$ and $R_{5'}$ taken together with the connecting C-atom may form a substituted or unsubstituted cycloalkyl or a substituted or unsubstituted heterocyclyl;

$R_6$ and $R_{6'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, $-CHOR_{10}$ and $-C(O)OR_{10}$;

wherein $R_{10}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

the alkyl, alkenyl or alkynyl, other than those defined in $R_{1'}$ or $R_2$, if substituted, is substituted with one or more substituent/s selected from $-OR_{13}$, halogen, $-CN$, haloalkyl, haloalkoxy and $-NR_{13}R_{13'''}$;

wherein $R_{13}$, are independently selected from hydrogen, unsubstituted $C_{1-6}$ alkyl, unsubstituted $C_{2-6}$ alkenyl, and unsubstituted $C_{2-6}$ alkynyl;

$R_{13'''}$ is selected from hydrogen, unsubstituted $C_{1-6}$ alkyl, unsubstituted $C_{2-6}$ alkenyl, unsubstituted $C_{2-6}$ alkynyl and -Boc;

the aryl, heterocyclyl or cycloalkyl other than those defined in $R_{1'}$ or $R_2$, if substituted, is substituted with one or more substituent/s selected from halogen, $-R_{14}$, $-OR_{14}$, $-NR_2$, $-NR_{14}R_{14'''}$, $NR_{14}C(O)R_{14'}$, $-NR_{14}S(O)_2R_{14'}$, $-S(O)_2NR_{14}R_{14'}$, $-NR_{14}C(O)N_{14'}R_{14'''}$, $-SR_{14}$, $-S(O)R_{14}$, $S(O)_2R_{14}$, $-CN$, haloalkyl, haloalkoxy, $-C(O)OR_{14}$, $-C(O)NR_{14}R_{14'}$, $-OCH_2CH_2OH$, $-NR_{14}S(O)_2NR_{14'}R_{14''}$ and $C(CH_3)_2OR_{14}$;

additionally, wherein the cycloalkyl or non-aromatic heterocyclyl, other than those defined in $R_{1'}$ or $R_2$, if substituted, may also be substituted with

or =O;

wherein $R_{14}$, $R_{14'}$ and $R_{14''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted cycloalkyl and unsubstituted heterocyclyl;

and wherein $R_{14'''}$ is selected from hydrogen, unsubstituted $C_{1-6}$ alkyl, unsubstituted $C_{2-6}$ alkenyl, unsubstituted $C_{2-6}$ alkynyl and -Boc;

These preferred compounds according to the invention are optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein m is 1, 2, 3, 4 or 5;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein n is 0, 1, 2, 3, 4 or 5;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general f Formula (I) is a compound wherein p is 0 or 1;

optionally in form of one of the stereoisomers, preferably enantiomers or diastereomers, a racemate or in form of a, mixture of at least two of the stereoisomers, preferably enantiomers and/or diastereomers, in any mixing ratio, or a corresponding salt thereof, or a corresponding solvate thereof.

In a further embodiment the compound according to the invention of general f Formula (I) is a compound wherein q is 0, 1 or 2;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein r is 0, 1 or 2;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein X is a bond, —C($R_x R_{x'}$)—, —C(O)—, —O—, —C(O)$NR_7$—, —$NR_7$C(O)— or —C(O)O—;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein X is a bond;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein X is —C($R_x R_{x'}$)—;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein X is —O—;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein X is —C(O)—;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein X is —C(O)$NR_7$—;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein X is —$NR_7$C(O)—;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein X is —C(O)O—;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein Y is —$CH_2$— or —C(O)—;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein Y is —$CH_2$—;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein Y is —C(O)—;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_1$ is optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
R$_1$ is $$\text{\textasciitilde}\!\!\!\overset{\displaystyle O}{\underset{\displaystyle }{C}}\!\!-R_1';$$

optionally in form of one of the stereoisomers, preferably enantiomers or diastereomers, a racemate or in form of a mixture of at least two of the stereoisomers, preferably enantiomers and/or diastereomers, in any mixing, ratio, or a corresponding salt thereof, or a corresponding solvate thereof.

In another preferred embodiment of the compound according to the invention of general Formula (I) is a compound wherein
R$_1$ is $$\text{\textasciitilde}\!\!\!\overset{\displaystyle R_4\ R_4'}{\underset{\displaystyle }{C}}\!\!-R_1';$$

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
R$_{1'}$ is selected from substituted or unsubstituted C$_{1-6}$ alkyl, substituted or unsubstituted C$_{2-6}$ alkenyl, substituted or unsubstituted C$_{2-6}$ alkynyl, substituted or unsubstituted cycloalkyl, substituted or unsubstituted aryl and substituted or unsubstituted heterocyclyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
R$_{1'}$ is selected from substituted or unsubstituted C$_{1-6}$ alkyl, substituted or unsubstituted C$_{2-6}$ alkenyl, substituted or unsubstituted C$_{2-6}$ alkynyl and substituted or unsubstituted aryl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
R$_{1'}$ is selected from substituted or unsubstituted C$_{1-6}$ alkyl and substituted or unsubstituted, aryl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
R$_2$ is selected from hydrogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted cycloalkyl, substituted or unsubstituted aryl and substituted or unsubstituted heterocyclyl,
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
R$_2$ is selected from substituted or unsubstituted C$_{1-6}$ alkyl, substituted or unsubstituted C$_{2-6}$ alkenyl, substituted or unsubstituted C$_{2-6}$ alkynyl and substituted or unsubstituted aryl,
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
R$_2$ is selected from substituted or unsubstituted C$_{1-6}$ alkyl and substituted or unsubstituted aryl,
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
R$_3$ and R$_{3'}$ are independently selected from hydrogen, substituted or unsubstituted C$_{1-6}$ alkyl, substituted or unsubstituted C$_{2-6}$ alkenyl and substituted or unsubstituted C$_{2-6}$ alkynyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
R$_3$ and R$_{3'}$ taken together with the connecting C-atom form a substituted or unsubstituted cycloalkyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
R$_4$ and R$_{4'}$ are independently selected from hydrogen, substituted or unsubstituted C$_{1-6}$ alkyl, substituted or unsubstituted $C_{2-6}$ alkenyl, substituted or unsubstituted $C_{2-6}$ alkynyl, —CHOR$_9$ and —C(O)OR$_9$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_5$ and $R_{5'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, —CHOR$_8$ and —C(O)OR$_8$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_5$ and $R_{5'}$ taken together with the connecting C-atom form a substituted or unsubstituted cycloalkyl or a substituted or unsubstituted heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_5$ and $R_{5'}$ taken together with the connecting C-atom form a substituted or unsubstituted cycloalkyl or a substituted or unsubstituted non-aromatic heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_5$ and $R_{5'}$ taken together with the connecting C-atom form a substituted or unsubstituted cycloalkyl or a substituted or unsubstituted heterocyclyl, while m is 1, X is a bond, n is 0 and $R_2$ is hydrogen, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_5$ and $R_{5'}$ taken together with the connecting C-atom form a substituted or unsubstituted cycloalkyl or a substituted or unsubstituted non-aromatic heterocyclyl, while m is 1, X is a bond, n is 0 and $R_2$ is hydrogen, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_6$ and $R_{6'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, —CHOR$_{10}$ and —C(O)OR$_{10}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_7$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_8$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_9$ is selected from hydrogen, substituted or unsubstituted $C_{1-9}$ alkyl, substituted or unsubstituted $C_{2-9}$ alkenyl and substituted or unsubstituted $C_{2-9}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{10}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{11}$, $R_{11'}$ and $R_{11''}$ are independently selected from hydrogen, unsubstituted $C_{1-6}$ alkyl, unsubstituted $C_{2-6}$ alkenyl and unsubstituted $C_{2-6}$ alkynyl;

and wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{11}$, $R_{11'}$ and $R_{11''}$ are independently selected from hydrogen, unsubstituted $C_{1-6}$ alkyl, unsubstituted $C_{2-6}$ alkenyl and unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{12}$, $R_{12'}$ and $R_{12''}$ are independently selected from hydrogen, unsubstituted $C_{1-6}$ alkyl, unsubstituted $C_{2-6}$ alkenyl and unsubstituted $C_{2-6}$ alkynyl;

and wherein $R_{12'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{12}$, $R_{12'}$ and $R_{12''}$ are independently selected from hydrogen, unsubstituted $C_{1-6}$ alkyl, unsubstituted $C_{2-6}$ alkenyl and unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{12'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{13}$, are independently selected from hydrogen, unsubstituted $C_{1-6}$ alkyl, unsubstituted $C_{2-6}$ alkenyl, and unsubstituted $C_{2-6}$ alkynyl;

$R_{13'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{13}$, are independently selected from hydrogen, unsubstituted $C_{1-6}$ alkyl, unsubstituted $C_{2-6}$ alkenyl, and unsubstituted $C_{2-5}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{13'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{14}$, $R_{14'}$ and $R_{14''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted cycloalkyl and unsubstituted heterocyclyl;

and wherein $R_{14'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{14}$, $R_{14'}$ and $R_{14'''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted cycloalkyl and unsubstituted heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{14'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_x$ is selected from halogen or substituted or unsubstituted $C_{1-6}$ alkyl, substituted or unsubstituted $C_{2-6}$ alkenyl substituted or unsubstituted $C_{2-6}$ alkynyl, and —$OR_7$;

$R_{x'}$ is selected from hydrogen, halogen or substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_x$ is selected from halogen or substituted or unsubstituted $C_{1-6}$ alkyl, substituted or unsubstituted $C_{2-6}$ alkenyl substituted or unsubstituted $C_{2-6}$ alkynyl, and —$OR_7$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{x'}$ is selected from hydrogen, halogen or substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I), is a compound wherein $R_1$ is

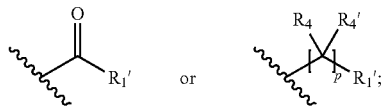

m is 1, 2, 3, 4 or 5;
n is 0, 1, 2, 3, 4 or 5;
p is 0 or 1;
q is 0, 1 or 2;
r is 0, 1 or 2;
Y is —$CH_2$— or —C(O)—;
X is a bond, —$C(R_xR_{x'})$—, —C(O)—, —O—, —C(O)$NR_7$—, —$NR_7$C(O)— or —C(O)O—;

$R_{1'}$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;

wherein the $C_{1-6}$ alkyl is preferably selected, from methyl, ethyl, propyl, butyl, pentyl, hexyl, isopropyl and 2-methylpropyl; more preferably the $C_{1-6}$ alkyl is methyl, ethyl or isopropyl;

and/or the $C_{2-6}$-alkenyl is preferably selected from, ethylene, propylene, butylene, pentylene and hexylene;

and/or the $C_{2-6}$-alkynyl is preferably selected from ethyne, propyne, butyne, pentyne and hexyne;

and/or the aryl is selected from phenyl, naphtyl, or anthracene; preferably is napthyl or phenyl; more preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

and/or $R_2$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl, wherein the $C_{1-6}$ alkyl is preferably selected from methyl, ethyl, propyl, butyl, pentyl, hexyl, isopropyl and 2-methylpropyl; more preferably the $C_{1-6}$ alkyl is methyl, isopropyl or isobutyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

and/or the aryl is selected from phenyl, naphtyl, or anthracene; preferably is napthyl or phenyl; more preferably is phenyl;

and/or the heterocyclyl is a heterocyclic ring system of one or more saturated or unsaturated rings of which at least one ring contains one or more heteroatoms, from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

and/or $R_3$ and $R_{3'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

wherein the $C_{1-6}$ alkyl is preferably selected from methyl, ethyl, propyl, butyl, pentyl, hexyl, isopropyl and 2-methylpropyl; preferably the $C_{1-6}$ alkyl is methyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

and/or $R_3$ and $R_{3'}$ taken together with the connecting C-atom may form a substituted or unsubstituted cycloalkyl;

wherein the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl; cyclobutyl, cyclopentyl, cyclohexyl, or cycloheptyl; more preferably from $C_{3-6}$ cycloalkyl like cyclopropyl, cyclobutyl, cyclopentyl or cyclohexyl; more preferably the cycloalkyl is cyclopropyl;

and/or $R_4$ and $R_{4'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, —CHOR$_9$ and —C(O)OR$_9$;

wherein the $C_{1-6}$ alkyl is preferably selected from methyl, ethyl, propyl, butyl, pentyl, hexyl, isopropyl and 2-methylpropyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

and/or $R_5$ and $R_{5'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, —CHOR$_8$ and —C(O)OR$_8$;

wherein the $C_{1-6}$ alkyl is preferably selected from methyl, ethyl, propyl, butyl, pentyl, hexyl, isopropyl and 2-methylpropyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

and/or the aryl is selected from phenyl, naphtyl, or anthracene; preferably is napthyl or phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

and/or $R_5$ and $R_{5'}$ taken together with the connecting C-atom may form a substituted or unsubstituted cycloalkyl or a substituted or unsubstituted heterocyclyl;

wherein the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidirie, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline; preferably the heterocyclyl is a non-aromatic heterocyclyl;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

and/or $R_6$ and $R_{6'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, —$CHOR_{10}$ and —$C(O)OR_{10}$;

wherein the $C_{1-6}$ alkyl is preferably selected from methyl, ethyl, propyl, butyl, pentyl, hexyl, isopropyl and 2-methylpropyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

and/or $R_7$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

wherein the $C_{1-6}$ alkyl is preferably selected from methyl, ethyl, propyl, butyl, pentyl, hexyl, isopropyl and 2-methylpropyl;

and/or the $C_{2-6}$-alkenyl is, preferably selected from ethylene, propylene, butylene, pentylene and hexylene;

and/or the $C_{2-6}$-alkynyl is-preferably selected from ethyne, propyne, butyne, pentyne and hexyne;

and/or $R_8$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

wherein the $C_{1-6}$ alkyl is preferably selected from methyl, ethyl, propyl, butyl, pentyl, hexyl, isopropyl and 2-methylpropyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

and/or $R_9$ is selected from hydrogen, substituted or unsubstituted $C_{1-9}$ alkyl, substituted or unsubstituted $C_{2-9}$ alkenyl and substituted or unsubstituted $C_{2-9}$ alkynyl; wherein the $C_{1-6}$ alkyl is preferably selected from methyl, ethyl, propyl, butyl, pentyl, hexyl, isopropyl and 2-methylpropyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

and/or $R_{10}$ is selected from hydrogen, substituted or unsubstituted $C_{1-6}$ alkyl, substituted or unsubstituted $C_{2-6}$ alkenyl and substituted or unsubstituted $C_{2-6}$ alkynyl; wherein the $C_{1-6}$ alkyl is preferably selected from methyl, ethyl, propyl, butyl, pentyl, hexyl, isopropyl and 2-methylpropyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

and/or $R_{11}$, $R_{11'}$ and $R_{11''}$ are independently selected from hydrogen, unsubstituted $C_{1-6}$ alkyl, unsubstituted $C_{2-6}$ alkenyl and unsubstituted $C_{2-6}$ alkynyl;

and wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc;

wherein the $C_{1-6}$ alkyl is preferably selected from methyl, ethyl, propyl, butyl, pentyl, hexyl, isopropyl and 2-methylpropyl; preferably the $C_{1-6}$ alkyl is methyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

and/or $R_{12}$, $R_{12'}$ and $R_{12''}$ are independently selected from hydrogen, unsubstituted $C_{1-6}$ alkyl, unsubstituted $C_{2-6}$ alkenyl and unsubstituted $C_{2-6}$ alkynyl;

and wherein $R_{12'''}$ is selected from hydrogen, unsubstituted $C_{1-6}$ alkyl, unsubstituted $C_{2-6}$ alkenyl, unsubstituted $C_{2-6}$ alkynyl and -Boc;

wherein the $C_{1-6}$ alkyl is preferably selected, from methyl, ethyl, propyl, butyl, pentyl, hexyl, isopropyl and 2-methylpropyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

and/or $R_{13}$, are independently selected from hydrogen, unsubstituted $C_{1-6}$ alkyl, unsubstituted $C_{2-6}$ alkenyl, and unsubstituted $C_{2-6}$ alkynyl;

$R_{13'''}$ is selected from hydrogen, unsubstituted $C_{1-6}$ alkyl, unsubstituted $C_{2-6}$ alkenyl, unsubstituted $C_{2-6}$ alkynyl and -Boc;

wherein the $C_{1-6}$ alkyl is preferably selected from methyl, ethyl, propyl, butyl, pentyl, hexyl, isopropyl and 2-methylpropyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

and/or $R_{14}$, $R_{14'}$ and $R_{14''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted cycloalkyl and unsubstituted heterocyclyl;

and wherein $R_{14'''}$ is selected from hydrogen, unsubstituted $C_{1-6}$ alkyl, unsubstituted $C_{2-6}$ alkenyl, unsubstituted $C_{2-6}$ alkynyl and -Boc;
wherein
the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
and/or
the aryl is selected from phenyl, naphtyl and anthracene; preferably is napthyl or phenyl;
and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline;

the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;
and/or
$R_x$ is selected from halogen or substituted or unsubstituted $C_{1-6}$ alkyl, substituted or unsubstituted $C_{2-6}$ alkenyl substituted or unsubstituted $C_{2-6}$ alkynyl, and $-OR_7$;
wherein
the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
and/or
$R_{x'}$ is selected from hydrogen, halogen or substituted or unsubstituted $C_{1-6}$ alkyl, substituted or unsubstituted $C_{2-6}$ alkenyl and substituted or unsubstituted $C_{2-6}$ alkynyl;
wherein
the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_1$, as defined in any of the embodiments of the present invention,
the $C_{1-6}$ alkyl is preferably selected from methyl, ethyl, propyl, butyl, pentyl, hexyl, isopropyl and 2-methylpropyl; more preferably the $C_{1-6}$ alkyl is methyl, ethyl or isopropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
and/or
the aryl is selected from phenyl, naphtyl, or anthracene; preferably is napthyl or phenyl; more preferably is phenyl;
and/or
the heterocycyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine; benzo-1,2,5-thiadiazole, indole, benzotriazole, benzoxazole oxopyrrolidine, pyrimidine, benzodioxolane, benzodioxane, carbazole and quinazoline;
and/or
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_2$ as defined in any of the embodiments of the present invention,
the $C_{1-6}$ alkyl is preferably selected from methyl, ethyl, propyl, butyl, pentyl, hexyl, isopropyl and 2-methylpropyl; more preferably the $C_{1-6}$ alkyl is methyl, isopropyl or isobutyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;

and/or the aryl is selected from phenyl, naphtyl, or anthracene; preferably is napthyl or phenyl; more preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which, at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_3$ as defined in any of the embodiments of the present invention, the $C_{1-6}$ alkyl is preferably selected from methyl, ethyl, propyl, butyl, pentyl, hexyl, isopropyl and 2-methylpropyl; preferably the $C_{1-6}$ alkyl is methyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{3'}$ as defined in any of the embodiments of the present invention, the $C_{1-6}$ alkyl is preferably selected from methyl, ethyl, propyl, butyl, pentyl, hexyl, isopropyl and 2-methylpropyl; preferably the $C_{1-6}$ alkyl is methyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_3$ and $R_{3'}$ forming with the connecting C-atom a substituted or unsubstituted cycloalkyl as defined in any of the embodiments of the present invention, the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl; more preferably the cycloalkyl is cyclopropyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_4$ and $R_{4'}$ as defined in any of the embodiments of the present invention, the $C_{1-6}$ alkyl is preferably selected from methyl, ethyl, propyl, butyl, pentyl, hexyl, isopropyl and 2-methylpropyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_5$ and $R_{5'}$ as defined in any of the embodiments of the present invention, the $C_{1-6}$ alkyl is preferably selected from methyl, ethyl, propyl, butyl, pentyl, hexyl, isopropyl and 2-methylpropyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

and/or the aryl is selected from phenyl, naphtyl, or anthracene; preferably is napthyl or phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_5$ and $R_{5'}$ forming with the connecting C-atom a substituted or unsubstituted cycloalkyl or a substituted or unsubstituted heterocyclyl, as defined in any of the embodiments of the present invention, the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline; the heterocyclyl is preferably a non-aromatic heterocyclyl, and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_6$ and $R_{6'}$ as defined in any of the embodiments of the present invention, the $C_{1-6}$ alkyl is preferably selected from methyl, ethyl, propyl, butyl, pentyl, hexyl, isopropyl and 2-methylpropyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_7$ as defined in any of the embodiments of the present invention, the $C_{1-6}$ alkyl is preferably selected from methyl, ethyl, propyl, butyl, pentyl, hexyl, isopropyl and 2-methylpropyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_8$ as defined in any of the embodiments of the present invention, the $C_{1-6}$ alkyl is preferably selected from methyl, ethyl, propyl, butyl, pentyl, hexyl, isopropyl and 2-methylpropyl;

and/or the $C_{2-6}$-alkenyl is preferably selected from ethylene, propylene, butylene, pentylene and hexylene;

and/or the $C_{2-6}$-alkynyl is preferably, selected from ethyne, propyne, butyne, pentyne and hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_9$ as defined in any of the embodiments of the present invention, the $C_{1-6}$ alkyl is preferably selected from methyl, ethyl, propyl, butyl, pentyl, hexyl, isopropyl and 2-methylpropyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{10}$ as defined in any of the embodiments of the present invention, the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{11}$, $R_{11'}$ and $R_{11''}$ as defined in any of the embodiments of the present invention,
the $C_{1-6}$ alkyl is preferably selected from methyl, ethyl, propyl, butyl, pentyl, hexyl, isopropyl and 2-methylpropyl; preferably methyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{11'''}$ as defined in any of the embodiments of the present invention,
the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{12}$, $R_{12'}$ and $R_{12''}$ as defined in any of the embodiments of the present invention,
the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{12'''}$ as defined in any of the embodiments of the present invention,
the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{13}$ and $R_{13'''}$ as defined in any of the embodiments of the present invention,
the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{14}$, $R_{14'}$ and $R_{14''}$ as defined in any of the embodiments of the present invention,
the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
and/or
the aryl is selected from phenyl, naphtyl and anthracene; preferably is napthyl or phenyl;
and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{14'''}$ as defined in any of the embodiments of the present invention, the $C_{1-6}$ alkyl is preferably selected from methyl, ethyl, propyl, butyl, pentyl, hexyl, isopropyl and 2-methylpropyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_x$ as defined in any of the embodiments of the present invention, the $C_{1-6}$ alkyl is preferably selected from methyl, ethyl, propyl, butyl, pentyl, hexyl, isopropyl and 2-methylpropyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{x'}$ as defined in any of the embodiments of the present invention, the $C_{1-6}$ alkyl is preferably selected from methyl, ethyl, propyl, butyl, pentyl, hexyl, isopropyl and 2-methylpropyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein n is 0, 1, 2, 3, 4 or 5; preferably n is 0 or 1;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein m is 1, 2, 3, 4 or 5; preferably m is-1 or 2;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein p is 0 or 1;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein q is 0, 1 or 2; preferably q is 0 or 1;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein r is 0, 1 or 2; preferably r is 0 or 1;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein X is a bond, —C($R_xR_{x'}$)—, —C(O)—, —O—, —C(O)N$R_7$—, —N$R_7$C(O)— or —C(O)O—; preferably, X is a bond;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein Y is —CH$_2$— or —C(O)—;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the invention according to general Formula (I) the compound is a compound, wherein X is a bond, —C(R$_x$R$_{x'}$)—, —C(O)—, —O—, —C(O)NR$_7$—, —NR$_7$C(O)— or —C(O)O—; preferably, X is a bond; and/or m is 1, 2, 3, 4 or 5; preferably m is 1 or 2; and/or
n is 0, 1, 2, 3, 4 or 5; preferably n is 0 or 1; and/or
p is 0 or 1; and/or
q is 0, 1 or 2; preferably q is 0 or 1; and/or
r is 0, 1 or 2; preferably r is 0 or 1;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I), the compound is a compound of Formula (I')

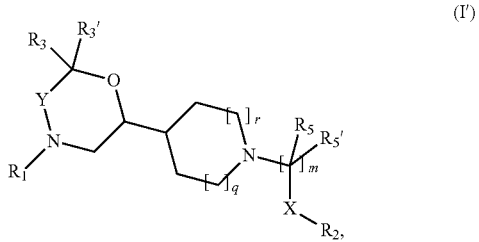

wherein
R$_1$ is

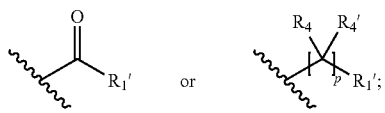

m is 1, 2, 3, 4 or 5;
p is 0 or 1;
q is 0, 1 or 2;
r is 0, 1 or 2;
Y is —CH$_2$— or —C(O)—;
X is a bond, —C(R$_x$R$_{x'}$)—, —C(O)—, —O—, —C(O)NR$_7$—, —NR$_7$C(O)— or —C(O)O—;
wherein R$_x$ is selected from halogen or substituted or unsubstituted C$_{1-6}$ alkyl, substituted or unsubstituted C$_{2-6}$ alkenyl substituted or unsubstituted C$_{2-6}$ alkynyl, and —OR$_7$;

R$_{x'}$ is selected from, hydrogen, halogen or substituted or unsubstituted C$_{1-6}$ alkyl, substituted or unsubstituted C$_{2-6}$ alkenyl and substituted or unsubstituted C$_{2-6}$ alkynyl;

R$_7$ is selected from hydrogen, substituted or unsubstituted C$_{1-6}$ alkyl, substituted or unsubstituted C$_{2-6}$ alkenyl and substituted or unsubstituted C$_{2-6}$ alkynyl;

R$_{1'}$ is selected from substituted or unsubstituted C$_{1-6}$ alkyl, substituted or unsubstituted C$_{2-4}$ alkenyl, substituted or unsubstituted C$_{2-6}$ alkynyl, substituted or unsubstituted cycloalkyl, substituted or unsubstituted aryl and substituted or unsubstituted heterocyclyl;

R$_2$ is selected from hydrogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted cycloalkyl, substituted or unsubstituted aryl and substituted or unsubstituted heterocyclyl, R$_3$ and R$_{3'}$ are independently selected from hydrogen, substituted or unsubstituted C$_{1-6}$ alkyl, substituted or unsubstituted C$_{2-6}$ alkenyl and substituted or unsubstituted C$_{2-6}$ alkynyl;

alternatively, R$_3$ and R$_{3'}$ taken together with the connecting C-atom may form a substituted or unsubstituted cycloalkyl;

R$_4$ and R$_{4'}$ are independently selected from hydrogen, substituted or unsubstituted C$_{1-6}$ alkyl, substituted or unsubstituted C$_{2-6}$ alkenyl, substituted or unsubstituted C$_{2-6}$ alkynyl, —CHOR$_9$ and —C(O)OR$_9$;
wherein R$_9$ is selected from hydrogen, substituted or unsubstituted C$_{1-9}$ alkyl, substituted or unsubstituted C$_{2-9}$ alkenyl and substituted or unsubstituted C$_{2-9}$ alkynyl;

R$_5$ and R$_{5'}$ are independently selected from hydrogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted cycloalkyl, substituted or unsubstituted aryl, substituted or unsubstituted heterocyclyl, —CHOR$_8$ and —C(O)OR$_8$;
wherein R$_8$ is selected from hydrogen, substituted or unsubstituted C$_{1-6}$ alkyl, substituted or unsubstituted C$_{2-6}$ alkenyl and substituted or unsubstituted C$_{2-6}$ alkynyl;

alternatively R$_5$ and R$_{5'}$ taken together with the connecting C-atom may form a substituted or unsubstituted cycloalkyl or a substituted or unsubstituted heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the invention according to general Formula (I) the compound is a compound of Formula (I$^{2'}$),

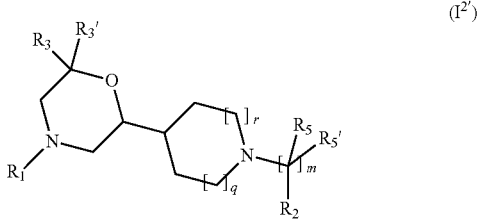

wherein
R₁ is

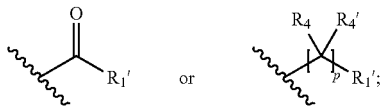

m is 1, 2, 3, 4 or 5;

p is 0 or 1;

q is 0, 1 or 2;

r is 0, 1 or 2;

$R_{1'}$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;

$R_2$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl, $R_3$ and $R_{3'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

alternatively, $R_3$ and $R_{3'}$ taken together with the connecting C-atom may form a substituted or unsubstituted cycloalkyl;

$R_4$ and $R_{4'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, —CHOR₉ and —C(O)OR₉;

wherein $R_9$ is selected from hydrogen, substituted or unsubstituted $C_{1-9}$ alkyl, substituted or unsubstituted $C_{2-9}$ alkenyl and substituted or unsubstituted $C_{2-9}$ alkynyl;

$R_5$ and $R_{5'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, —CHOR₈ and —C(O)OR₈;

wherein $R_8$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

alternatively $R_5$ and $R_{5'}$ taken together with the connecting C-atom may form a substituted or unsubstituted cycloalkyl or a substituted or unsubstituted heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the invention according to general Formula (I) the compound is a compound of Formula (I³'),

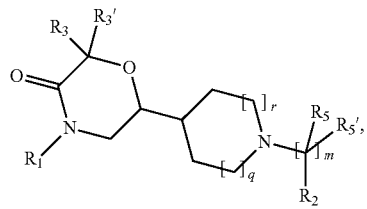

(I³')

wherein
R₁ is

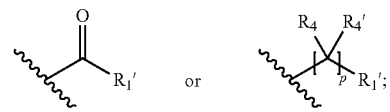

m is 1, 2, 3, 4 or 5;

p is 0 or 1;

q is 0, 1 or 2;

r is 0, 1 or 2;

$R_{1'}$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;

$R_2$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl, $R_3$ and $R_{3'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

alternatively, $R_3$ and $R_{3'}$ taken together with the connecting C-atom may form a substituted or unsubstituted cycloalkyl;

$R_4$ and $R_{4'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, —CHOR₉ and —C(O)OR₉;

wherein $R_9$ is selected from hydrogen, substituted or unsubstituted $C_{1-9}$ alkyl, substituted or unsubstituted $C_{2-9}$ alkenyl and substituted or unsubstituted $C_{2-9}$ alkynyl;

$R_5$ and $R_{5'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, —CHOR₈ and —C(O)OR₈;

wherein $R_8$ is selected from, hydrogen, substituted or unsubstituted $C_{1-6}$ alkyl, substituted or unsubstituted $C_{2-6}$ alkenyl and substituted or unsubstituted $C_{2-6}$ alkynyl;

alternatively $R_5$ and $R_{5'}$ taken together with the connecting C-atom may form a substituted or unsubstituted cycloalkyl or a substituted or unsubstituted heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the invention according to general Formula (I) the compound is a compound of Formula (I$^{4'}$),

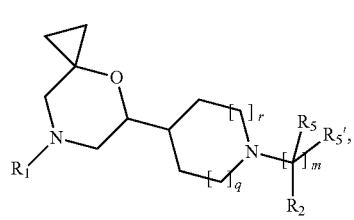

(I$^{4'}$)

wherein
R$_1$ is

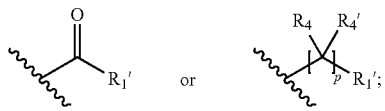

m is 1, 2, 3, 4 or 5;
p is 0 or 1;
q is 0, 1 or 2;
r is 0, 1 or 2;
R$_{1'}$ is selected from substituted or unsubstituted C$_{1-6}$ alkyl, substituted or unsubstituted C$_{2-6}$ alkenyl, substituted or unsubstituted C$_{2-6}$ alkynyl, substituted or unsubstituted cycloalkyl, substituted or unsubstituted aryl and substituted or unsubstituted heterocyclyl;
R$_2$ is selected from hydrogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted cycloalkyl, substituted or unsubstituted aryl and substituted or unsubstituted heterocyclyl,
R$_4$ and R$_{4'}$ are independently selected from hydrogen, substituted or unsubstituted C$_{1-6}$ alkyl, substituted or unsubstituted C$_{2-6}$ alkenyl, substituted or unsubstituted C$_{2-6}$ alkynyl, —CHOR$_9$ and —C(O)OR$_9$;
  wherein R$_9$ is selected from hydrogen, substituted or unsubstituted C$_{1-9}$ alkyl, substituted or unsubstituted C$_{2-9}$ alkenyl and substituted or unsubstituted C$_{2-9}$ alkynyl;
R$_5$ and R$_{5'}$ are independently selected from hydrogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted cycloalkyl, substituted or unsubstituted aryl, substituted or unsubstituted heterocyclyl, —CHOR$_8$ and —C(O)OR$_8$;
  wherein R$_8$ is selected from hydrogen, substituted or unsubstituted C$_{1-6}$ alkyl, substituted or unsubstituted C$_{2-6}$ alkenyl and substituted or unsubstituted C$_{2-6}$ alkynyl;
  alternatively R$_5$ and R$_{5'}$ taken together with the connecting C-atom may form a substituted or unsubstituted cycloalkyl or a substituted or unsubstituted heterocyclyl;
  optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the invention according to general Formula (I) the compound is a compound of Formula (I$^{5'}$),

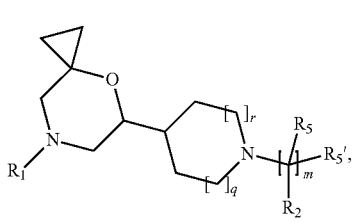

(I$^{5'}$)

wherein
R$_1$ is

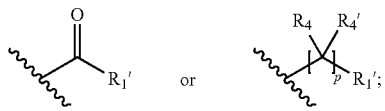

m is 1, 2, 3, 4 or 5;
p is 0 or 1;
q is 0, 1 or 2;
r is 0, 1 or 2;
R$_{1'}$ is selected from substituted or unsubstituted C$_{1-6}$ alkyl, substituted or unsubstituted C$_{2-6}$ alkenyl, substituted or unsubstituted C$_{2-6}$ alkynyl, substituted or unsubstituted cycloalkyl, substituted or unsubstituted aryl and substituted or unsubstituted heterocyclyl;
R$_2$ is selected from hydrogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted cycloalkyl, substituted or unsubstituted aryl and substituted or unsubstituted heterocyclyl,
R$_4$ and R$_{4'}$ are independently selected from hydrogen, substituted or unsubstituted C$_{1-6}$ alkyl, substituted or unsubstituted C$_{2-6}$ alkenyl, substituted or unsubstituted C$_{2-6}$ alkynyl, —CHOR$_9$ and —C(O)OR$_9$;
  wherein R$_9$ is selected from, hydrogen, substituted or unsubstituted C$_{1-9}$ alkyl, substituted or unsubstituted C$_{2-9}$ alkenyl and substituted or unsubstituted C$_{2-9}$ alkynyl;
R$_5$ and R$_{5'}$ are independently selected from hydrogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted cycloalkyl, substituted or unsubstituted aryl, substituted or unsubstituted heterocyclyl, —CHOR$_8$ and —C(O)OR$_8$;
  wherein R$_8$ is selected from hydrogen, substituted or unsubstituted C$_{1-6}$ alkyl, substituted or unsubstituted C$_{2-6}$ alkenyl and substituted or unsubstituted C$_{2-6}$ alkynyl;
  alternatively R$_5$ and R$_{5'}$ taken together with the connecting C-atom may form a substituted or unsubstituted cycloalkyl or a substituted or unsubstituted heterocyclyl;
  optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the invention according to general Formula (I) the compound is a compound of Formula (I⁶'),

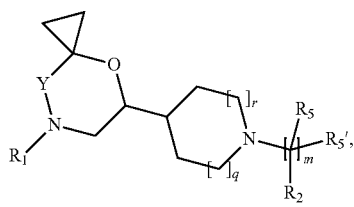

wherein
R₁ is

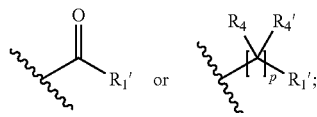

m is 1, 2, 3, 4 or 5;
p is 0 or 1;
q is 0, 1 or 2;
r is 0, 1 or 2;
Y is —CH₂— or —C(O)—;
R₁' is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;
R₂ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl,
R₄ and R₄' are independently selected from hydrogen, substituted or unsubstituted $C_{1-6}$ alkyl, substituted or unsubstituted $C_{2-6}$ alkenyl, substituted or unsubstituted $C_{2-6}$ alkynyl, —CHOR₉ and —C(O)OR₉;
  wherein R₉ is selected from hydrogen, substituted or unsubstituted $C_{1-9}$ alkyl, substituted or unsubstituted $C_{2-9}$ alkenyl and substituted or unsubstituted $C_{2-9}$ alkynyl;
R₅ and R₅' are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, —CHOR₈ and —C(O)OR₈;
  wherein R₈ is selected from hydrogen, substituted or unsubstituted $C_{1-6}$ alkyl, substituted or unsubstituted $C_{2-6}$ alkenyl and substituted or unsubstituted $C_{2-6}$ alkynyl;
  alternatively R₅ and R₅' taken together with the connecting C-atom may form a substituted or unsubstituted cycloalkyl or a substituted or unsubstituted heterocyclyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment
R₁ is a substituted or unsubstituted group selected from ethyl, isopropyl, phenyl, benzyl and —C(O)-phenyl; more preferably a substituted or unsubstituted group selected from phenyl, benzyl and —C(O)-phenyl or unsubstituted ethyl or unsubstituted isopropyl.

In a preferred embodiment
R₁' is a substituted or unsubstituted group selected from methyl, ethyl, isopropyl and phenyl; more preferably a substituted or unsubstituted phenyl or an unsubstituted methyl or unsubstituted ethyl or unsubstituted isopropyl.

In a preferred embodiment
R₂ is a substituted or unsubstituted group selected from methyl and phenyl; more preferably an unsubstituted group selected from methyl and phenyl.

In a preferred embodiment
R₂ is a substituted or unsubstituted group selected from isopropyl, isobutyl and phenyl; more preferably a substituted or unsubstituted phenyl or an unsubstituted group selected from isopropyl and isobutyl.

In a preferred embodiment
R₂ is a substituted or unsubstituted group selected from methyl, isopropyl, isobutyl and phenyl; more preferably a substituted or unsubstituted phenyl or an unsubstituted group selected from methyl, isopropyl and isobutyl.

In a preferred embodiment
R₃ is hydrogen or a substituted or unsubstituted methyl, preferably hydrogen or unsubstituted methyl.

In a preferred embodiment
R₃' is hydrogen or a substituted or unsubstituted methyl, preferably hydrogen or unsubstituted methyl.

In a preferred embodiment
R₃ is hydrogen or a substituted or unsubstituted methyl, preferably hydrogen or unsubstituted methyl, while R₃' is hydrogen or a substituted or unsubstituted methyl, preferably hydrogen or unsubstituted methyl.

In a preferred embodiment
R₃ is hydrogen, while R₃' is hydrogen or a substituted or unsubstituted methyl, preferably hydrogen or unsubstituted methyl.

In a preferred embodiment
R₃ is substituted or unsubstituted methyl, preferably unsubstituted methyl, while R₃' is hydrogen.

In a preferred embodiment
R₃ and R₃' are both hydrogen.

In a preferred embodiment
R₃ and R₃' are both substituted or unsubstituted methyl, preferably unsubstituted methyl.

In a preferred embodiment
R₃ and R₃' taken together with the connecting C-atom form a substituted or unsubstituted cyclopropyl: preferably unsubstituted cyclopropyl.

In a preferred embodiment
R₄ and R₄' are both hydrogen.

In a preferred embodiment
R₅ and R₅' are both hydrogen.

In a preferred embodiment
R₆ and R₆' are both hydrogen.

In a preferred embodiment
X is a bond.

In a preferred embodiment
Y is —CH₂— or —C(O)—.

In another preferred embodiment
n is 0 or 1.

In another preferred embodiment m is 1 or 2.
In another preferred embodiment p is 0 or 1.
In another preferred embodiment q is 0 or 1.
In another preferred embodiment r is 0 or 1.
In another preferred embodiment q and r are both 0.
In another preferred embodiment q and r are both 1.
In another preferred embodiment q and r are both independently 0 or 1.
In another preferred embodiment, especially of a compound of Formula (I$^{2'}$) and/or of Formula (I$^{3'}$), q and r are both 1.
In another preferred embodiment, especially of a compound of Formula (I$^{2'}$) and/or of Formula (I$^{3'}$), q and r are both 0.

In another preferred embodiment, especially of a compound of Formula (I$^{6'}$) as well as (I$^{6a'}$), (I$^{6b'}$) and (I$^{c6'}$), q and r are both independently 0 or 1.
In another preferred embodiment, especially of a compound of Formula (I$^{6'}$) as well as (I$^{6a'}$), (I$^{6b'}$) and (I$^{6c'}$), q and r are both 1.
In another preferred embodiment, especially of a compound of Formula (I$^{6'}$) as well as (I$^{6a'}$), (I$^{6b'}$) and (I$^{6c'}$), q and r are both 0.
In another preferred embodiment, especially of a compound of Formula (I$^{6'}$) as well as (I$^{6a'}$), (I$^{6b'}$) and (I$^{6C'}$), q and r are both independently 0 or 1.

In a particular embodiment the halogen is fluorine or chlorine.

In a particular embodiment the halogen is fluorine.

In a preferred further embodiment, the compounds of the general Formula (I) are selected from

| EXAMPLE | Structure | CHEMICAL NAME |
|---|---|---|
| 1 | 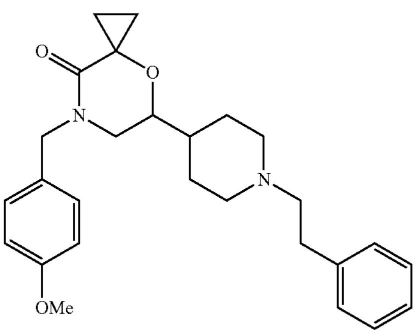 [SMILES: COc1ccc(CN2CC(C3CCN(CCc4ccccc4)CC3)OC3(CC3)C2=O)cc1] | 7-(4-methoxybenzyl)-5-(1-phenethylpiperidin-4-yl)-4-oxa-7-azaspiro[2.5]octan-8-one |
| 2 | 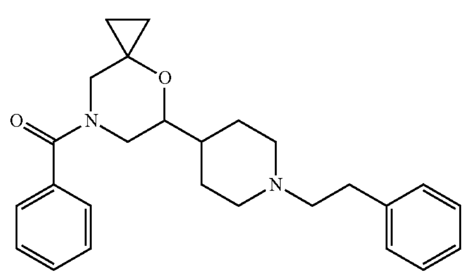 [SMILES: O=C(c1ccccc1)N1CC(C2CCN(CCc3ccccc3)CC2)OC2(CC2)C1] | (5-(1-phenethylpiperidin-4-yl)-4-oxa-7-azaspiro[2.5]octan-7-yl)(phenyl)methanone |
| 3 | 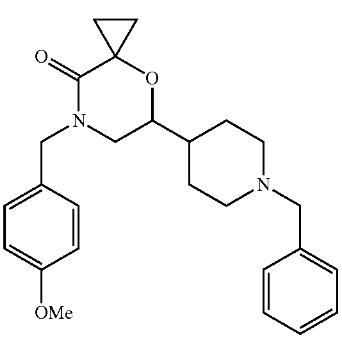 [SMILES: COc1ccc(CN2CC(C3CCN(Cc4ccccc4)CC3)OC3(CC3)C2=O)cc1] | 5-(1-benzylpiperidin-4-yl)-7-(4-methoxybenzyl)-4-oxa-7-azaspiro[2.5]octan-8-one |

-continued

| EXAMPLE | Structure | CHEMICAL NAME |
|---|---|---|
| 4 | 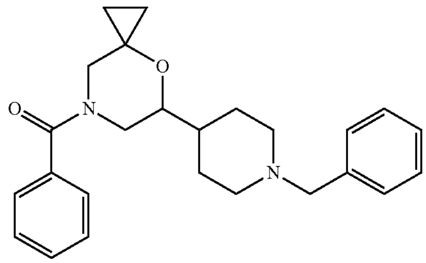 [SMILES: O=C(c1ccccc1)N1CC(C2CCN(Cc3ccccc3)CC2)OC2(CC2)C1] | (5-(1-benzylpiperidin-4-yl)-4-oxa-7-azaspiro[2.5]octan-7-yl)(phenyl)methanone |
| 5 | 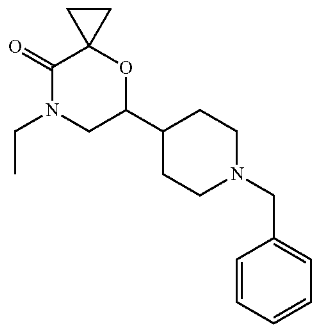 [SMILES: CCN1CC(C2CCN(Cc3ccccc3)CC2)OC2(CC2)C1=O] | 5-(1-benzylpiperidin-4-yl)-7-ethyl-4-oxa-7-azaspiro[2.5]octan-8-one |
| 6 | 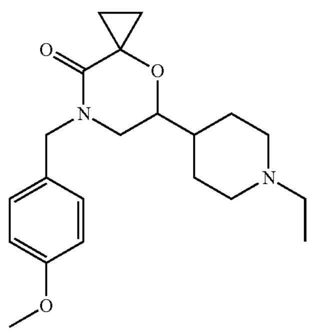 [SMILES: CCN1CCC(C2CN(Cc3ccc(OC)cc3)C(=O)C3(CC3)O2)CC1] | 5-(1-ethylpiperidin-4-yl)-7-(4-methoxybenzyl)-4-oxa-7-azaspiro[2.5]octan-8-one |
| 7 | 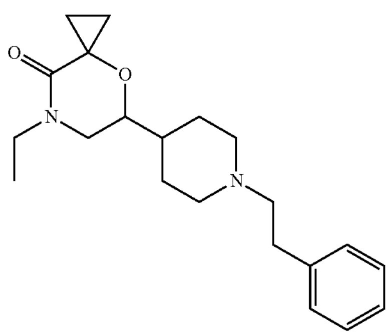 [SMILES: CCN1CC(C2CCN(CCc3ccccc3)CC2)OC2(CC2)C1=O] | 7-ethyl-5-(1-phenethylpiperidin-4-yl)-4-oxa-7-azaspiro[2.5]octan-8-one |
| 8 | 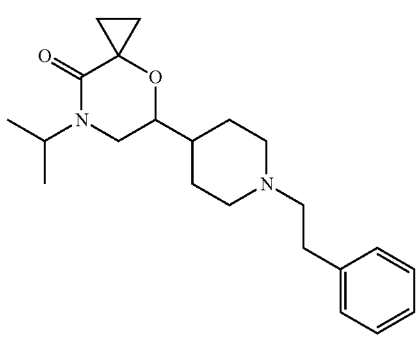 [SMILES: CC(C)N1CC(C2CCN(CCc3ccccc3)CC2)OC2(CC2)C1=O] | 7-isopropyl-5-(1-phenethylpiperidin-4-yl)-4-oxa-7-azaspiro[2.5]octan-8-one |

| EXAMPLE | Structure | CHEMICAL NAME |
|---|---|---|
| 9 | 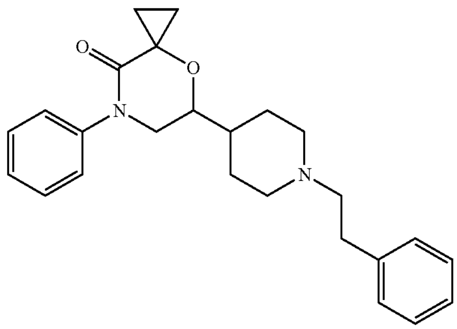 [SMILES: O=C1N(c2ccccc2)CC(C2CCN(CCc3ccccc3)CC2)OC12CC2] | 5-(1-phenethylpiperidin-4-yl)-7-phenyl-4-oxa-7-azaspiro[2.5]octan-8-one |
| 10 | 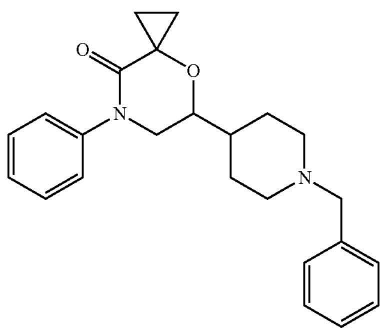 [SMILES: O=C1N(c2ccccc2)CC(C2CCN(Cc3ccccc3)CC2)OC12CC2] | 5-(1-benzylpiperidin-4-yl)-7-phenyl-4-oxa-7-azaspiro[2.5]octan-8-one |
| 11 | 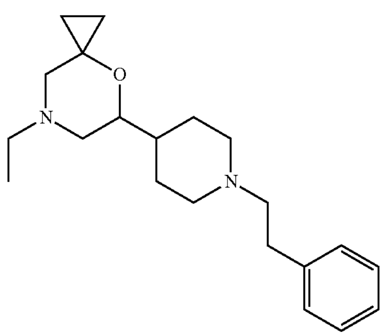 [SMILES: CCN1CC(C2CCN(CCc3ccccc3)CC2)OC2(CC2)C1] | 7-ethyl-5-(1-phenethylpiperidin-4-yl)-4-oxa-7-azaspiro[2.5]octane |
| 12 | 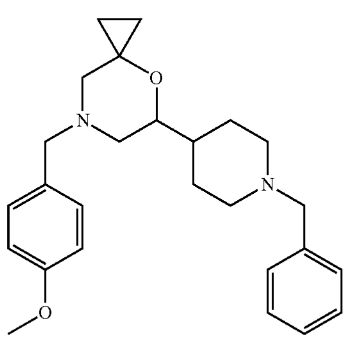 [SMILES: COc1ccc(CN2CC(C3CCN(Cc4ccccc4)CC3)OC3(CC3)C2)cc1] | 5-(1-benzylpiperidin-4-yl)-7-(4-methoxybenzyl)-4-oxa-7-azaspiro[2.5]octane |

| EXAMPLE | Structure | CHEMICAL NAME |
|---|---|---|
| 13 | 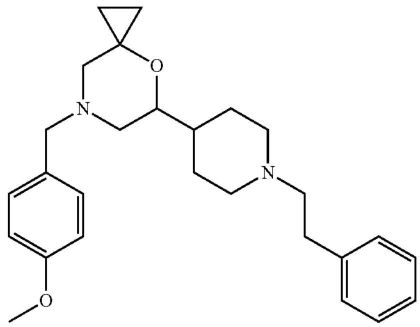 [SMILES: COc1ccc(CN2CC(C3CCN(CCc4ccccc4)CC3)OC3(CC3)C2)cc1] | 7-(4-methoxybenzyl)-5-(1-phenethylpiperidin-4-yl)-4-oxa-7-azaspiro[2.5]octane |
| 14 | | 5-(1-benzylpiperidin-4-yl)-7-ethyl-4-oxa-7-azaspiro[2.5]octane | optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred further embodiment, the compounds of the general Formula (I) are selected from

| EX | Structure | Chemical name |
|---|---|---|
| 15 | 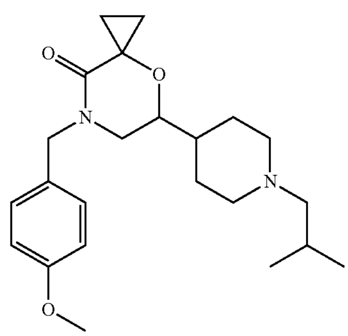 [SMILES: COc1ccc(CN2CC(C3CCN(CC(C)C)CC3)OC3(CC3)C2=O)cc1] | 5-(1-isobutylpiperidin-4-yl)-7-(4-methoxybenzyl)-4-oxa-7-azaspiro[2.5]octan-8-one |
| 16 | 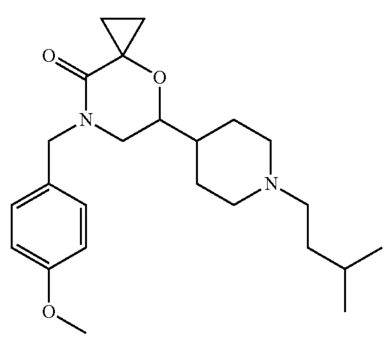 [SMILES: COc1ccc(CN2CC(C3CCN(CCC(C)C)CC3)OC3(CC3)C2=O)cc1] | 5-(1-isopentylpiperidin-4-yl)-7-(4-methoxybenzyl)-4-oxa-7-azaspiro[2.5]octan-8-one |

-continued

| EX | Structure | Chemical name |
|---|---|---|
| 17 | 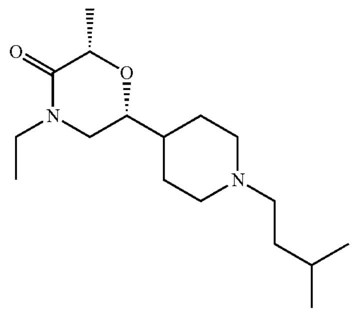 [SMILES: CCN1C[C@@H](C2CCN(CCC(C)C)CC2)O[C@@H](C)C1=O] | (2S,6R)-4-ethyl-6-(1-isopentylpiperidin-4-yl)-2-methylmorpholin-3-one |
| 18 | 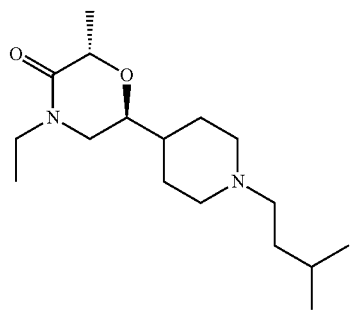 [SMILES: CCN1C[C@H](C2CCN(CCC(C)C)CC2)O[C@@H](C)C1=O] | (2S,6S)-4-ethyl-6-(1-isopentylpiperidin-4-yl)-2-methylmorpholin-3-one |
| 19 | 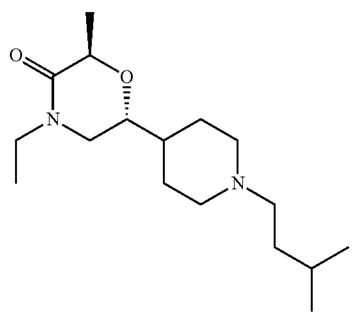 [SMILES: CCN1C[C@@H](C2CCN(CCC(C)C)CC2)O[C@H](C)C1=O] | (2R,6R)-4-ethyl-6-(1-isopentylpiperidin-4-yl)-2-methylmorpholin-3-one |
| 20 | 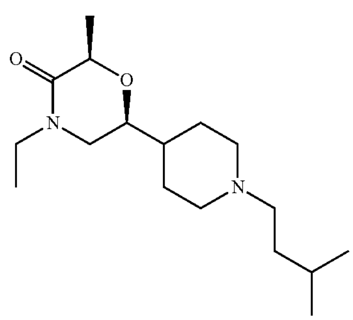 [SMILES: CCN1C[C@H](C2CCN(CCC(C)C)CC2)O[C@H](C)C1=O] | (2R,6S)-4-ethyl-6-(1-isopentylpiperidin-4-yl)-2-methylmorpholin-3-one |
| 21 | 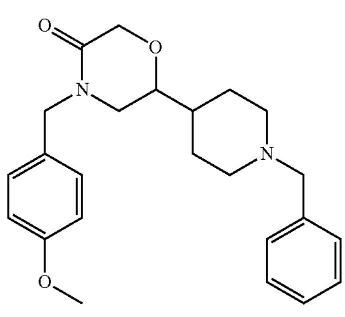 [SMILES: COc1ccc(CN2CC(C3CCN(Cc4ccccc4)CC3)OCC2=O)cc1] | 6-(1-benzylpiperidin-4-yl)-4-(4-methoxybenzyl)morpholin-3-one |

-continued

| EX | Structure | Chemical name |
|---|---|---|
| 22 | 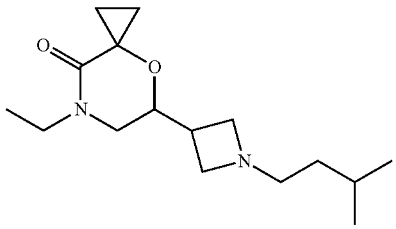 [SMILES: CCN1CC(C2CN(CCC(C)C)C2)OC2(CC2)C1=O] | 7-ethyl-5-(1-isopentylazetidin-3-yl)-4-oxa-7-azaspiro[2.5]octan-8-one |
| 23 | 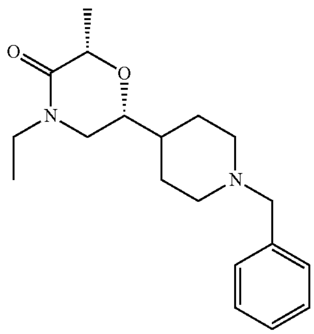 [SMILES: CCN1C[C@@H](C2CCN(Cc3ccccc3)CC2)O[C@@H](C)C1=O] | (2S,6R)-6-(1-benzylpiperidin-4-yl)-4-ethyl-2-methylmorpholin-3-one |
| 24 | 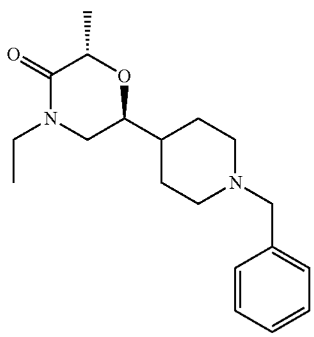 [SMILES: CCN1C[C@H](C2CCN(Cc3ccccc3)CC2)O[C@@H](C)C1=O] | (2S,6S)-6-(1-benzylpiperidin-4-yl)-4-ethyl-2-methylmorpholin-3-one |
| 25 | 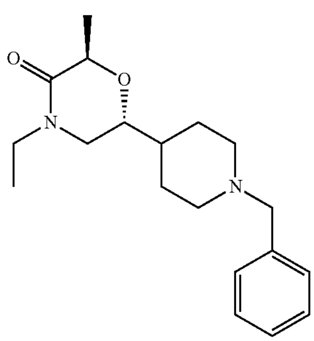 [SMILES: CCN1C[C@@H](C2CCN(Cc3ccccc3)CC2)O[C@H](C)C1=O] | (2R,6R)-6-(1-benzylpiperidin-4-yl)-4-ethyl-2-methylmorpholin-3-one |
| 26 | 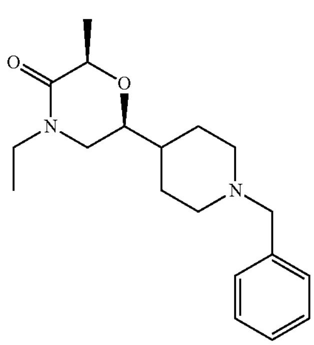 [SMILES: CCN1C[C@H](C2CCN(Cc3ccccc3)CC2)O[C@H](C)C1=O] | (2R,6S)-6-(1-benzylpiperidin-4-yl)-4-ethyl-2-methylmorpholin-3-one |

-continued

| EX | Structure | Chemical name |
|---|---|---|
| 27 | 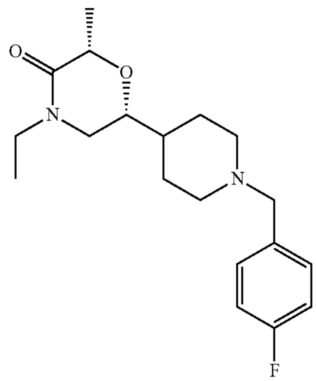 [SMILES: CCN1C[C@@H](C2CCN(Cc3ccc(F)cc3)CC2)O[C@@H](C)C1=O] | (2S,6R)-4-ethyl-6-(1-(4-fluorobenzyl)piperidin-4-yl)-2-methylmorpholin-3-one |
| 28 | 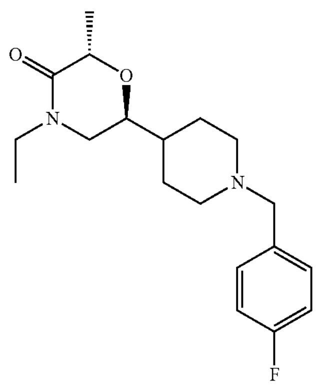 [SMILES: CCN1C[C@H](C2CCN(Cc3ccc(F)cc3)CC2)O[C@@H](C)C1=O] | (2S,6S)-4-ethyl-6-(1-(4-fluorobenzyl)piperidin-4-yl)-2-methylmorpholin-3-one |
| 29 | 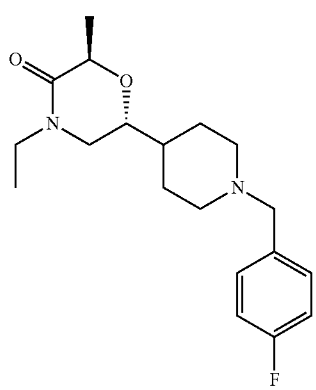 [SMILES: CCN1C[C@@H](C2CCN(Cc3ccc(F)cc3)CC2)O[C@H](C)C1=O] | (2R,6R)-4-ethyl-6-(1-(4-fluorobenzyl)piperidin-4-yl)-2-methylmorpholin-3-one |
| 30 | 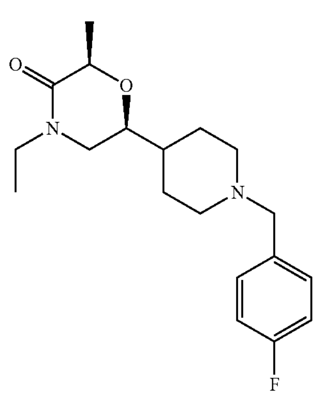 [SMILES: CCN1C[C@H](C2CCN(Cc3ccc(F)cc3)CC2)O[C@H](C)C1=O] | (2R,6S)-4-ethyl-6-(1-(4-fluorobenzyl)piperidin-4-yl)-2-methylmorpholin-3-one |

| EX | Structure | Chemical name |
|---|---|---|
| 31 | 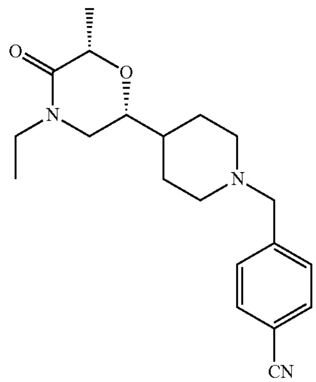 [SMILES: CCN1C[C@@H](C2CCN(Cc3ccc(C#N)cc3)CC2)O[C@@H](C)C1=O] | 4-((4-((2R,6S)-4-ethyl-6-methyl-5-oxomorpholin-2-yl)piperidin-1-yl)methyl)benzonittile- |
| 32 | 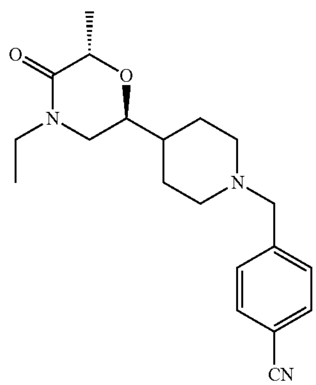 [SMILES: CCN1C[C@H](C2CCN(Cc3ccc(C#N)cc3)CC2)O[C@@H](C)C1=O] | 4-((4-((2S,6S)-4-ethyl-6-methyl-5-oxomorpholin-2-yl)piperidin-1-yl)methyl)benzonitnle |
| 33 | 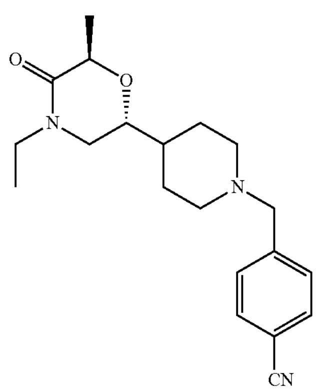 [SMILES: CCN1C[C@@H](C2CCN(Cc3ccc(C#N)cc3)CC2)O[C@H](C)C1=O] | 4-((4-((2R,6R)-4-ethyl-6-methyl-5-oxomorpholin-2-yl)piperidin-1-yl)methyl)benzonitrile |
| 34 | 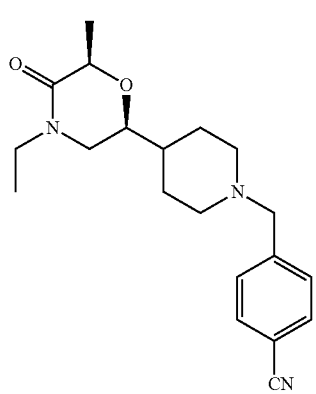 [SMILES: CCN1C[C@H](C2CCN(Cc3ccc(C#N)cc3)CC2)O[C@H](C)C1=O] | 4-((4-((2S,6R)-4-ethyl-6-methyl-5-oxomorpholin-2-yl)piperidin-1-yl)methyl)benzonitrile |

| EX | Structure | Chemical name |
|----|-----------|---------------|
| 35 | 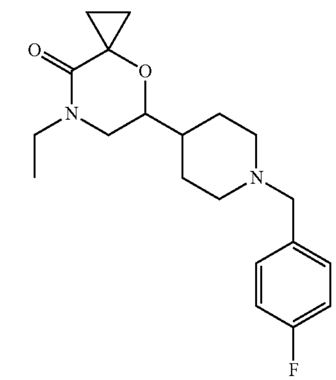 [SMILES: CCN1CC(C2CCN(Cc3ccc(F)cc3)CC2)OC2(CC2)C1=O] | 7-ethyl-5-(1-(4-fluorobenzyl)piperidin-4-yl)4-oxa-7-azaspiro[2.5]octan-8-one |
| 36 | 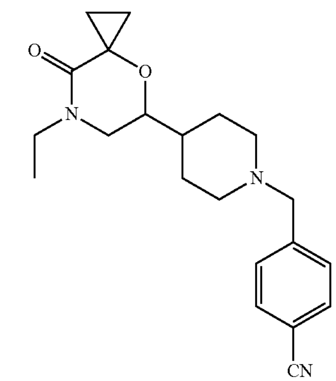 [SMILES: CCN1CC(C2CCN(Cc3ccc(C#N)cc3)CC2)OC2(CC2)C1=O] | 4-((4-(7-ethyl-8-oxo-4-oxa-7-azaspiro[2.5]octan-5-yl)piperidin-1-yl)methyl)benzonitrile |
| 37 | 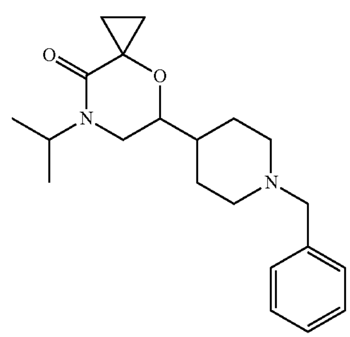 [SMILES: CC(C)N1CC(C2CCN(Cc3ccccc3)CC2)OC2(CC2)C1=O] | 5-(1-benzylpiperidin-4-yl)-7-isopropyl-4-oxa-7-azaspiro[2.5]octan-3-one |
| 38 | 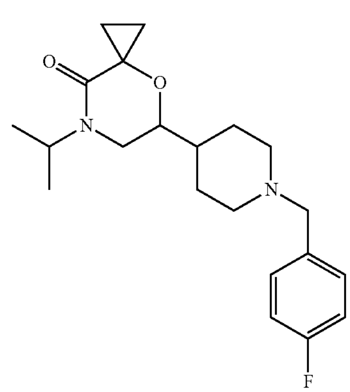 [SMILES: CC(C)N1CC(C2CCN(Cc3ccc(F)cc3)CC2)OC2(CC2)C1=O] | 5-(1-(4-fluorobenzyl)piperidin-4-yl)-7-isopropyl-4-oxa-7-azaspiro[2.5]octan-8-one |

| EX | Structure | Chemical name |
|---|---|---|
| 39 | 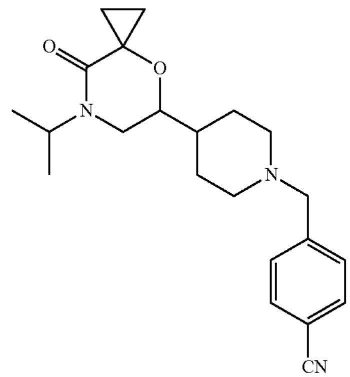 [SMILES: CC(C)N1CC(C2CCN(Cc3ccc(C#N)cc3)CC2)OC2(CC2)C1=O] | 4-((4-(7-isopropyl-8-oxo-4-oxa,7-azaspiro[2.5]octan-5-yl)piperidin-1-yl)methyl)benzonitrile |
| 40 | 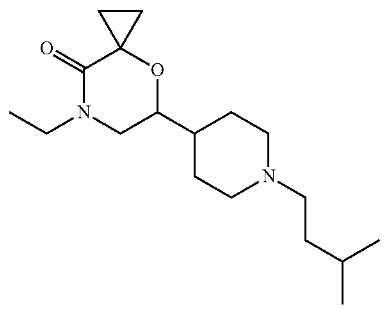 [SMILES: CCN1CC(C2CCN(CCC(C)C)CC2)OC2(CC2)C1=O] | 7-ethyl-5-(1-isopentylpiperidin-4-yl)-4-oxa-7-azaspiro[2.5]octan-8-one |
| 41 | 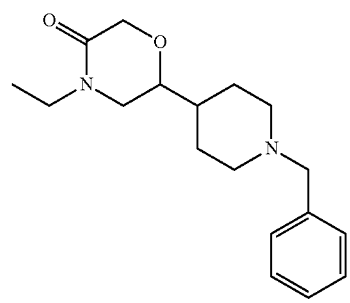 [SMILES: CCN1CC(C2CCN(Cc3ccccc3)CC2)OCC1=O] | 6-(1-benzylpiperidin-4-yl)-4-ethylmorpholin-3-one |
| 42 | 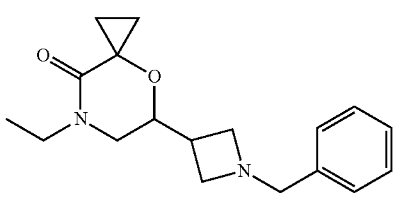 [SMILES: CCN1CC(C2CN(Cc3ccccc3)C2)OC2(CC2)C1=O] | 5-(1-benzylazetidin-3-yl)-7-ethyl-4-oxa-7-azaspiro[2.5]octan-8-one |
| 43 | 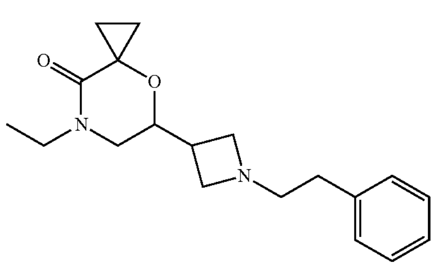 [SMILES: CCN1CC(C2CN(CCc3ccccc3)C2)OC2(CC2)C1=O] | 7-ethyl-5-(1-phenethylazetidin-3-yl)-4-oxa-7-azaspiro[2.5]octan-8-one |

-continued

| EX | Structure | Chemical name |
|---|---|---|
| 44 | 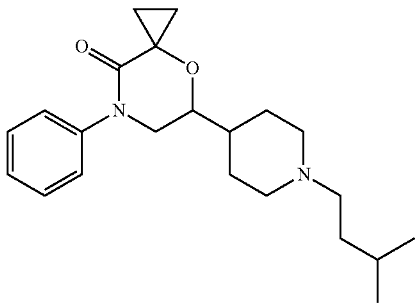 [SMILES: CC(C)CCN1CCC(C2CN(c3ccccc3)C(=O)C3(CC3)O2)CC1] | 5-(1-isopentylpiperidin-4-yl)-7-phenyl-4-oxa-7-azaspiro[2.5]octan-8-one |
| 45 | 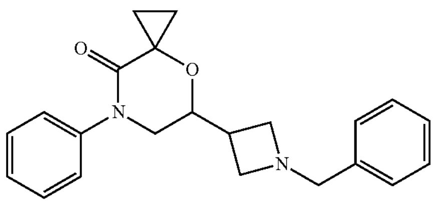 | 5-(1-benzylazetidin-3-yl)-7-phenyl-4-oxa-7-azaspiro[2.5]octan-8-one |
| 46 | 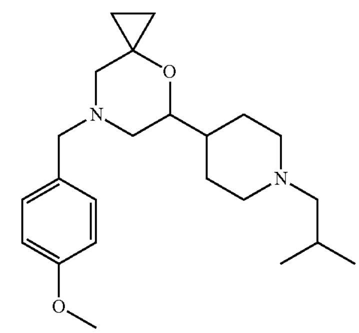 [SMILES: COc1ccc(CN2CC(C3CCN(CC(C)C)CC3)OC3(CC3)C2)cc1] | 5-(1-isobutylpiperidin-4-yl)-7-(4-methoxybenzyl)-4-oxa-7-azaspiro[2.5]octane |
| 47 | 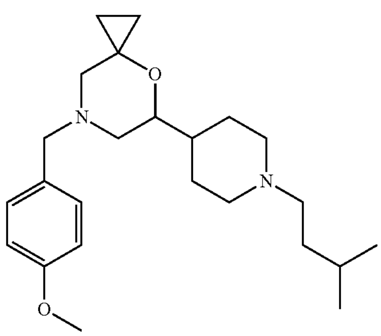 [SMILES: COc1ccc(CN2CC(C3CCN(CCC(C)C)CC3)OC3(CC3)C2)cc1] | 5-(1-isopentylpiperidin-4-yl)-7-(4-methoxybenzyl)-4-oxa-7-azaspiro[2.5]octane |
| 48 | 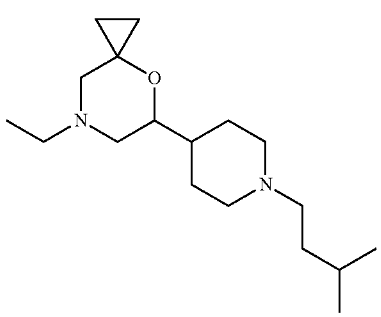 [SMILES: CCN1CC(C2CCN(CCC(C)C)CC2)OC2(CC2)C1] | 7-ethyl-5-(1-isopentylpiperidin-4-yl)-4-oxa-7-azaspiro[2.5]actane |

-continued

| EX | Structure | Chemical name |
|---|---|---|
| 49 | 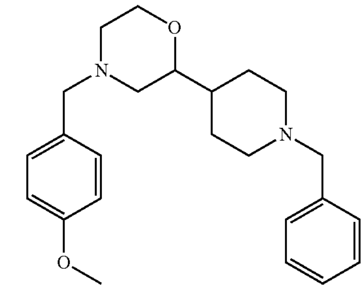 [SMILES: COc1ccc(CN2CCOC(C3CCN(Cc4ccccc4)CC3)C2)cc1] | 2-(1-benzylpiperidin-4-yl)-4-(4-methoxybenzyl)moropholine |
| 50 | 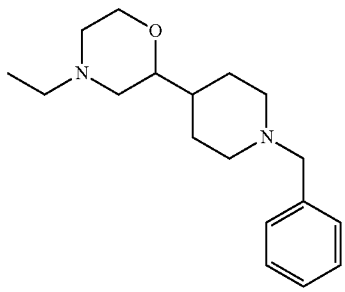 [SMILES: CCN1CCOC(C2CCN(Cc3ccccc3)CC2)C1] | 2-(1-benzylpiperidin-4-yl)-4-ethylmorpholine |
| 51 | 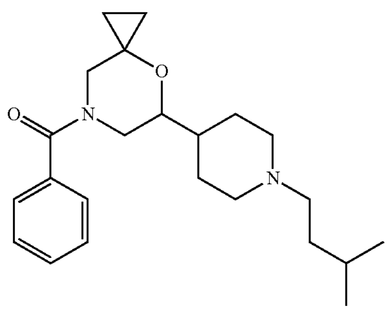 [SMILES: CC(C)CCN1CCC(C2CN(C(=O)c3ccccc3)CC3(CC3)O2)CC1] | (5-(1-Isopentylpiperidin-4-yl)-4-oxa-7-azaspiro[2.5]octan-7-yl)(phenyl)methanone |
| 52 | 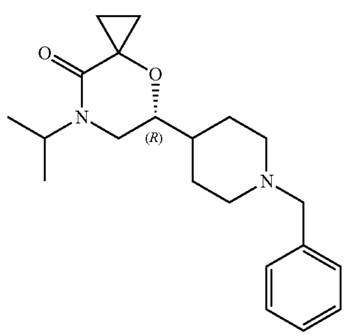 | (R)-5-(1-Benzylpiperidin-4-yl)-7-ethyl-4-oxa-7-azaspiro[2.5]octan-8-one |
| 53 | 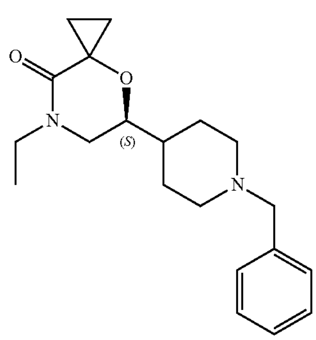 | (S)-5-(1-benzylpiperidin-4-yl)-7-ethyl-4-oxa-7-azaspiro[2.5]octan-8-one |

-continued

| EX | Structure | Chemical name |
|---|---|---|
| 54 | 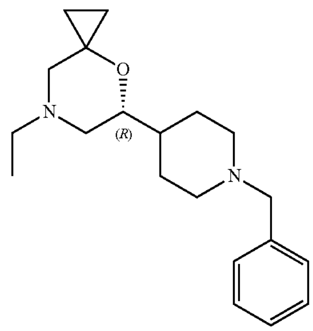 | (R)-5-(1-Benzylpiperidin-4-yl)-7-ethyl-4-oxa-7-azaspiro[2.5]octane |
| 55 | 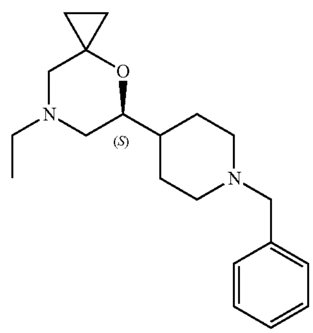 | (S)-5-(1-benzylpiperidin-4-yl)-7-ethyl-4-oxa-7-azaspiro[2.5]octane |
| 56 | 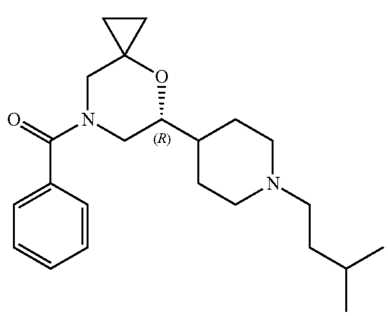 | (R)-(5-(1-Isopentylpiperidin-4-yl)-4-oxa-7-azaspiro[2.5]octan-7-yl)(phenyl)methanone |
| 57 | 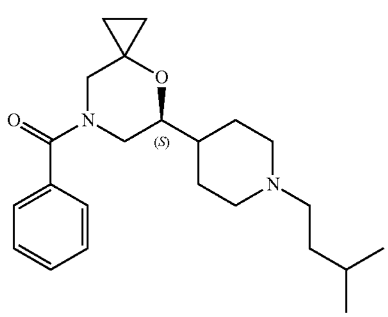 | (S)-(5-(1-isopentylpiperidin-4-yl)-4-oxa-7-azaspiro[2.5]octan-7-yl)(phenyl)methanone |
| 58 | 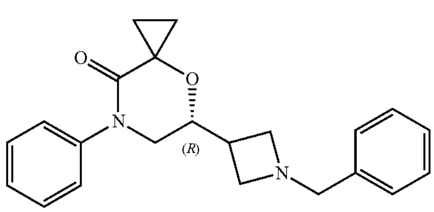 | (R)-5-(1-Benzylazetidin-3-yl)-7-phenyl-4-oxa-7-azaspiro[2.5]octan-8-one |

| EX | Structure | Chemical name |
|---|---|---|
| 59 | 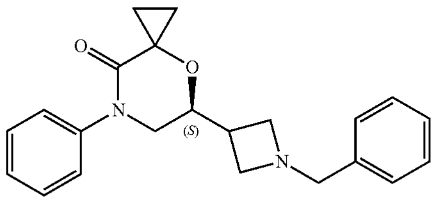 | (S)-5-(1-benzylazetidin-3-yl)-7-phenyl-4-oxa-7-azaspiro[2.5]octan-8-one |
| 60 | 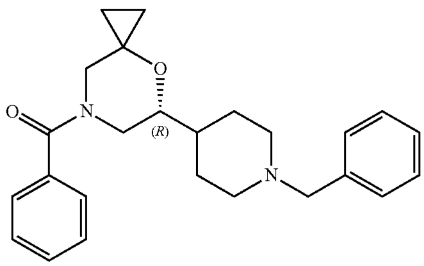 | (R)-(5-(1-Benzylpiperidin-4-yl)-4-oxa-7-azaspiro[2.5]octan-7-yl)(phenyl)methanone |
| 61 | | (S)-(5-(1-benzylpiperidin-4-yl)-4-oxa-7-azaspiro[2.5]octan-7-yl)(phenyl)methanone | optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred further embodiment; the compounds of the general Formula (I) are selected from

| EX | Structure | Chemical name |
|---|---|---|
| 15 | 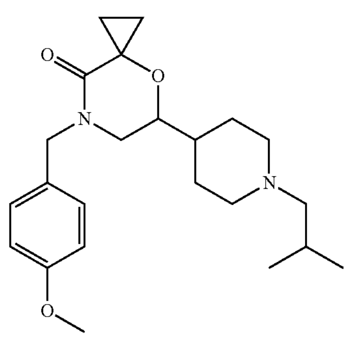 [SMILES: COc1ccc(CN2CC(C3CCN(CC(C)C)CC3)OC3(CC3)C2=O)cc1] | 5-(1-isobutylpiperidin-4-yl)-7-(4-methoxybenzyl)-4-oxa-7-azaspiro[2.5]octan-8-one |

-continued

| EX | Structure | Chemical name |
|---|---|---|
| 16 | 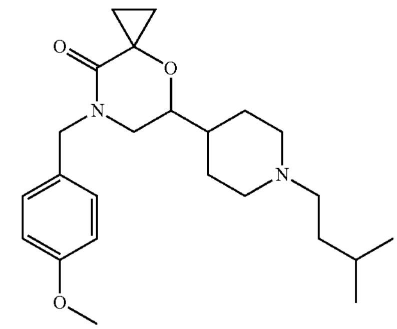 [SMILES: COc1ccc(CN2CC(C3CCN(CCC(C)C)CC3)OC3(CC3)C2=O)cc1] | 5-(1-isopentylpiperidin-4-yl)-7-(4-methoxybenzyl)4-oxa-7-azaspiro[2.5]octan-8-one |
| 21 | 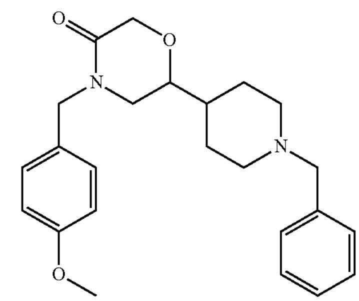 [SMILES: COc1ccc(CN2CC(C3CCN(Cc4ccccc4)CC3)OCC2=O)cc1] | 6-(1-benzylpiperidin-4-yl)-4-(4-methoxybenzyl)morpholin-3-one |
| 22 | 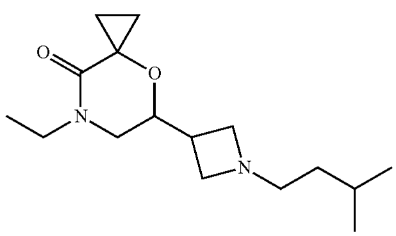 [SMILES: CCN1CC(C2CN(CCC(C)C)C2)OC2(CC2)C1=O] | 7-ethyl-5-(1-isopentylazetidin-3-yl)-4-oxa-7-azaspiro[2.5]octan-8-one |
| 23 | 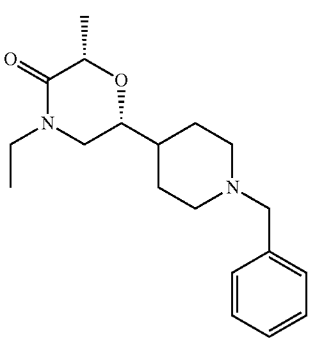 [SMILES: CCN1C[C@@H](C2CCN(Cc3ccccc3)CC2)O[C@@H](C)C1=O] | (2S,6R)-6-(1-benzylpiperidin-4-yl)-4-ethyl-2-methylmorpholin-3-one |
| 24 | 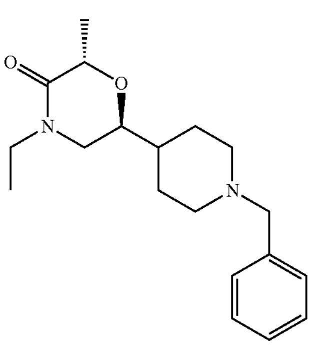 [SMILES: CCN1C[C@H](C2CCN(Cc3ccccc3)CC2)O[C@@H](C)C1=O] | (2S,6S)-6-(1-benzylpiperidin-4-yl)-4-ethyl-2-methylmorpholin-3-one |

-continued

| EX | Structure | Chemical name |
|----|-----------|---------------|
| 25 | 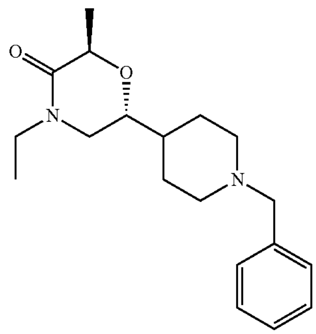 [SMILES: CCN1C[C@@H](C2CCN(Cc3ccccc3)CC2)O[C@H](C)C1=O] | (2R,6R)-6-(1-benzylpiperidin-4-yl)-4-ethyl-2-methylmorpholin-3-one |
| 26 | 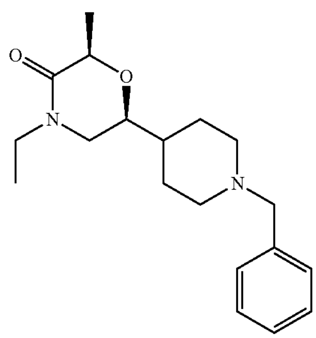 [SMILES: CCN1C[C@H](C2CCN(Cc3ccccc3)CC2)O[C@H](C)C1=O] | (2R,6S)-6-(1-benzylpiperidin-4-yl)-4-ethyl-2-methylmorpholin-3-one |
| 27 | 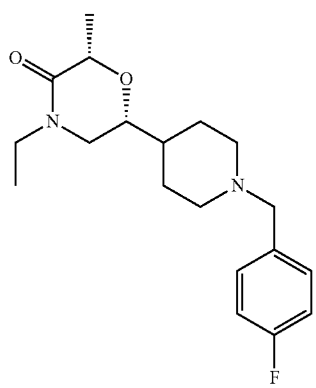 [SMILES: CCN1C[C@@H](C2CCN(Cc3ccc(F)cc3)CC2)O[C@@H](C)C1=O] | (2S,6R)-4-ethyl-6-(1-(4-fluorobenzyl)piperidin-4-yl)-2-methylmorpholin-3-one |
| 28 | 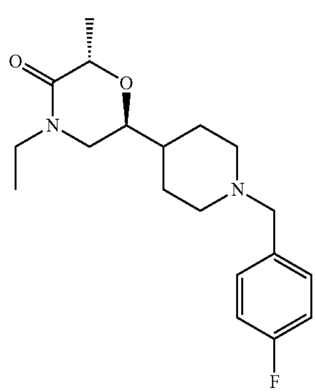 [SMILES: CCN1C[C@H](C2CCN(Cc3ccc(F)cc3)CC2)O[C@@H](C)C1=O] | (2S,6S)-4-ethyl-6-(1-(4-fluorobenzyl)piperidin-4-yl)-2-methylmorpholin-3-one |

-continued

| EX | Structure | Chemical name |
|---|---|---|
| 29 | 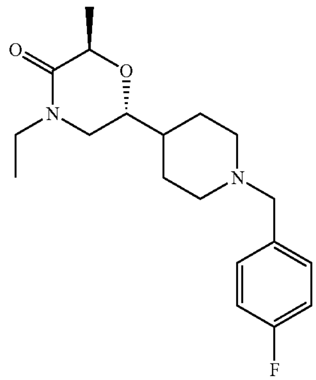 [SMILES: CCN1C[C@@H](C2CCN(Cc3ccc(F)cc3)CC2)O[C@H](C)C1=O] | (2R,3R)-4-ethyl-6-(1-(4-fluorobenzyl)piperidln-4-yl)-2-methylmorpholin-3-one |
| 30 | 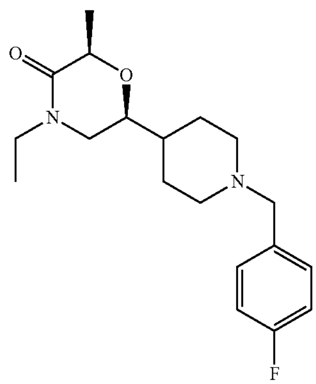 [SMILES: CCN1C[C@H](C2CCN(Cc3ccc(F)cc3)CC2)O[C@H](C)C1=O] | (2R,6S)-4-ethyl-6-(1-(4-fluorobenzyl)piperidin-4-yl)-2-methylmorpholin-3-one |
| 31 | 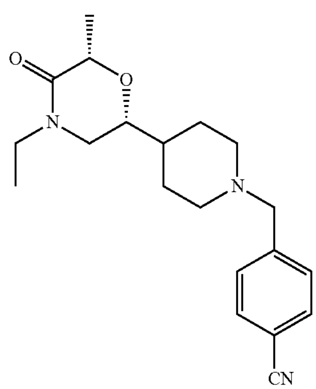 [SMILES: CCN1C[C@@H](C2CCN(Cc3ccc(C#N)cc3)CC2)O[C@@H](C)C1=O] | 4-((4-((2R,6S)-4-ethyl-6-methyl-5-oxomorpholin-2-yl)piperidin-1-yl)methyl)benzonitrile |
| 32 | 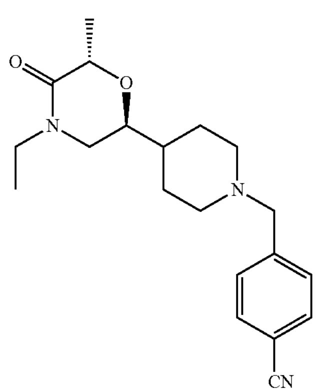 [SMILES: CCN1C[C@H](C2CCN(Cc3ccc(C#N)cc3)CC2)O[C@@H](C)C1=O] | 4-((4-((2S,6S)-4-ethyl-6-methyl-5-oxomorpholin-2-yl)piperidin-1-yl)methyl)benzonitrile |

| EX | Structure | Chemical name |
|---|---|---|
| 33 | 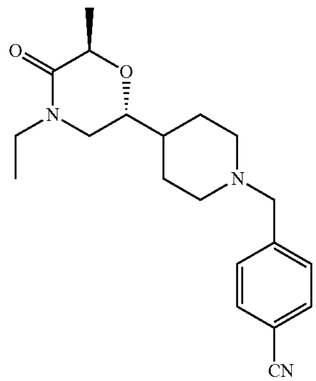 [SMILES: CCN1C[C@@H](C2CCN(Cc3ccc(C#N)cc3)CC2)O[C@H](C)C1=O] | 4-((4-((2R,6R)-4-ethyl-6-methyl-5-oxomorpholin-2-yl)piperidin-1-yl)methyl)benzonitrile |
| 34 | 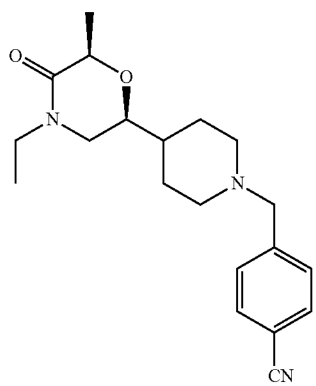 [SMILES: CCN1C[C@H](C2CCN(Cc3ccc(C#N)cc3)CC2)O[C@H](C)C1=O] | 4-((4-((2S,6R)-4-ethyl-6-methyl-5-oxomorpholin-2-yl)piperidin-1-yl)methyl)benzonitrile |
| 35 | 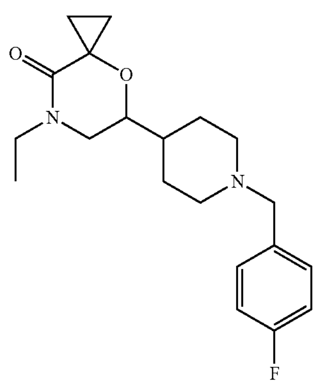 [SMILES: CCN1CC(C2CCN(Cc3ccc(F)cc3)CC2)OC2(CC2)C1=O] | 7-ethyl-5-(1-(4-fluorobenzyl)piperidin-4-yl)-4-oxa-7-azaspiro[2.5]octan-8-one |
| 36 | 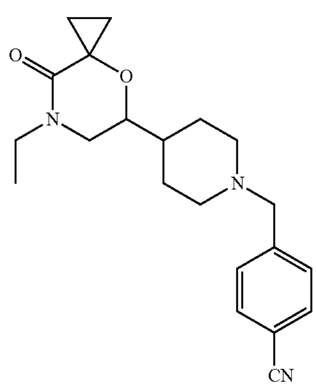 [SMILES: CCN1CC(C2CCN(Cc3ccc(C#N)cc3)CC2)OC2(CC2)C1=O] | 4-((4-(7-ethyl-8-oxo-4-oxa-7-azaspiro[2.5]octan-5-yl)piperidin-1-yl)methyl)benzonitrile |

-continued

| EX | Structure | Chemical name |
|---|---|---|
| 37 | 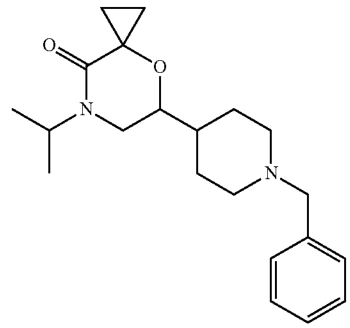 [SMILES: CC(C)N1CC(C2CCN(Cc3ccccc3)CC2)OC2(CC2)C1=O] | 5-(1-benzylpiperidin-4-yl)-7-isopropyl-4-oxa-7-azaspiro[2.5]octan-8-one |
| 38 | 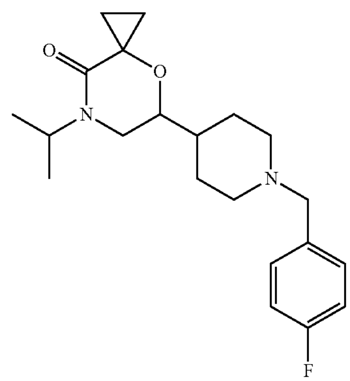 [SMILES: CC(C)N1CC(C2CCN(Cc3ccc(F)cc3)CC2)OC2(CC2)C1=O] | 5-(1-(4-fluorobenzyl)piperidin-4-yl)-7-isopropyl-4-oxa-7-azaspiro[2.5]octan-8-one |
| 39 | 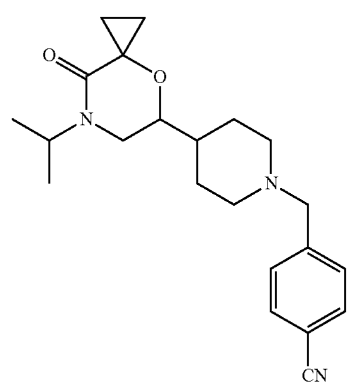 [SMILES: CC(C)N1CC(C2CCN(Cc3ccc(C#N)cc3)CC2)OC2(CC2)C1=O] | 4-((4-(7-isopropyl-8-oxo-4-oxa-7-azaspiro[2.5]octan-5-yl)piperidin-1-yl)methyl)benzonitrile |
| 40 | 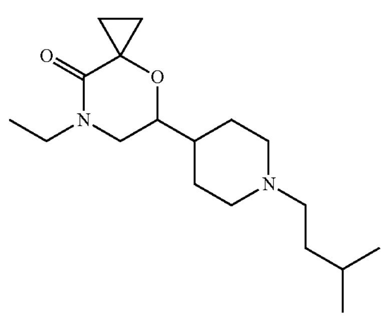 [SMILES: CCN1CC(C2CCN(CCC(C)C)CC2)OC2(CC2)C1=O] | 7-ethyl-5-(1-isopentylpiperidin-4-yl)-4-oxa-7-azaspiro[2.5]octan-8-one |

-continued

| EX | Structure | Chemical name |
|---|---|---|
| 41 | 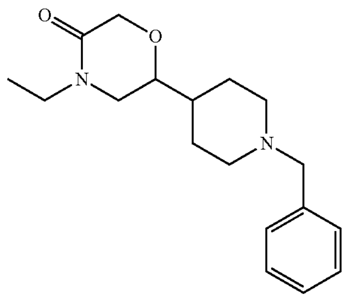 [SMILES: CCN1CC(C2CCN(Cc3ccccc3)CC2)OCC1=O] | 6-(1-benzylpiperidin-4-yl)-4-ethylmorpholin-3-one |
| 42 | 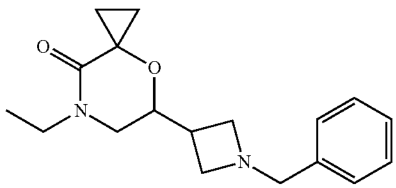 [SMILES: CCN1CC(C2CN(Cc3ccccc3)C2)OC2(CC2)C1=O] | 5-(1-benzylazetidin-3-yl)-7-ethyl-4-oxa-7-azaspiro[2.5]octan-8-one |
| 43 | 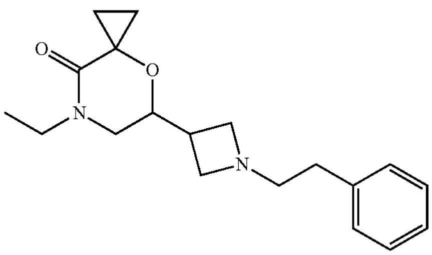 [SMILES: CCN1CC(C2CN(CCc3ccccc3)C2)OC2(CC2)C1=O] | 7-ethyl-5-(1-phenethylazetidin-3-yl)-4-oxa-7-azaspiro[2.5]octan-8-one |
| 44 | 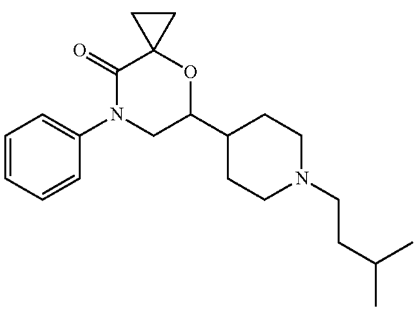 [SMILES: CC(C)CCN1CCC(C2CN(c3ccccc3)C(=O)C3(CC3)O2)CC1] | 5-(1-isopentylpiperidin-4-yl)-7-phenyl-4-oxa-7-azaspiro[2.5]octan-6-one |
| 45 | 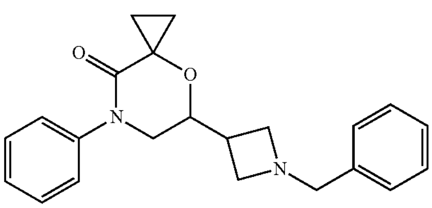 [SMILES: O=C1N(c2ccccc2)CC(C2CN(Cc3ccccc3)C2)OC12CC2] | 5-(1-benzylazetidin-3-yl)-7-phenyl-4-oxa-7-azaspiro[2.5]octan-8-one |
| 46 | 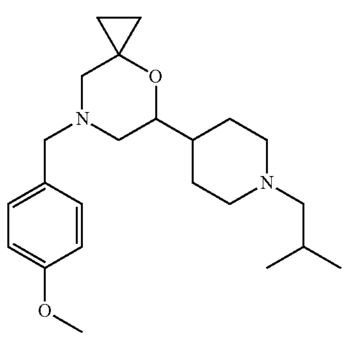 [SMILES: COc1ccc(CN2CC(C3CCN(CC(C)C)CC3)OC3(CC3)C2)cc1] | 5-(1-isobutylpiperidin-4-yl)-7-(4-methoxybenzyl)-4-oxa-7-azaspiro[2.5]octane |

-continued

| EX | Structure | Chemical name |
|---|---|---|
| 47 | 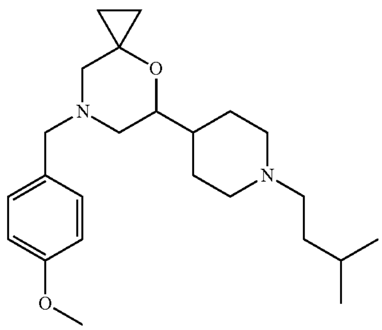 [SMILES: COc1ccc(CN2CC(C3CCN(CCC(C)C)CC3)OC3(CC3)C2)cc1] | 5-(1-isopentylpiperidin-4-yl)-7-(4-methoxybenzyl)-4-oxa-7-azaspiro[2.5]octane |
| 48 | 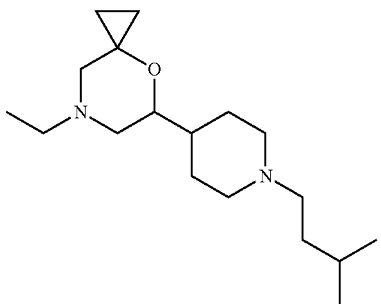 [SMILES: CCN1CC(C2CCN(CCC(C)C)CC2)OC2(CC2)C1] | 7-ethyl-5-(1-isopentylpiperidin-4-yl)-4-oxa-7-azaspiro[2.5]octane |
| 49 | 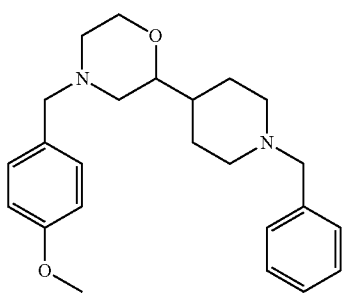 [SMILES: COc1ccc(CN2CCOC(C3CCN(Cc4ccccc4)CC3)C2)cc1] | 2-(1-benzylpiperidin-4-yl)-4-(4-methoxybenzyl)morpholine |
| 50 | 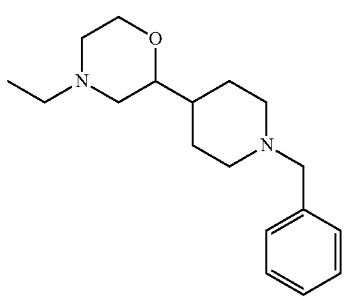 [SMILES: CCN1CCOC(C2CCN(Cc3ccccc3)CC2)C1] | 2-(1-benzylpiperidin-4-yl)-4-ethylmorpholine |
| 51 | | (5-(1-Isopentylpiperidin-4-yl)-4-oxa-7-azaspiro[2.5]octan-7-yl)(phenyl)methanone | optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred further embodiment, the compounds of the general Formula (I) are selected from

| 17 | 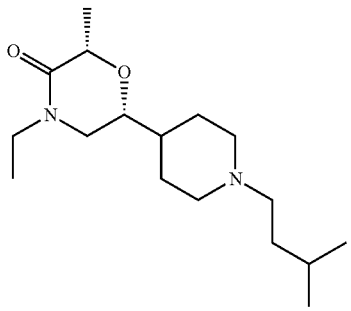 [SMILES: CCN1C[C@@H](C2CCN(CCC(C)C)CC2)O[C@@H](C)C1=O] | (2S,6R)-4-ethyl-6-(1-isopentylpiperidin-4-yl)-2-methylmorpholin-3-one |
| 18 | 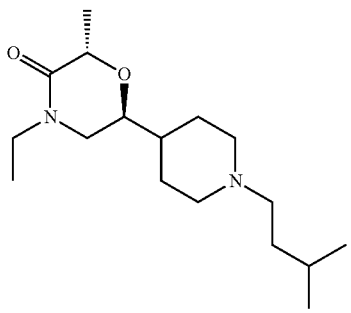 [SMILES: CCN1C[C@H](C2CCN(CCC(C)C)CC2)O[C@@H](C)C1=O] | (2S,6S)-4-ethyl-6-(1-isopentylpiperidin-4-yl)-2-methylmorpholin-3-one |
| 19 | 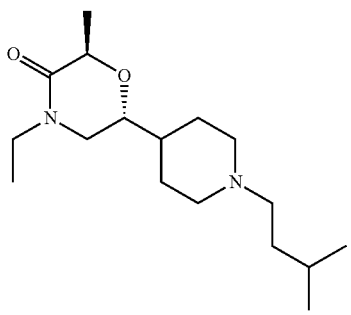 [SMILES: CCN1C[C@@H](C2CCN(CCC(C)C)CC2)O[C@H](C)C1=O] | (2R,6R)-4-ethyl-6-(1-isopentylpiperidin-4-yl)-2-methylrnorpholin-3-one |
| 20 | 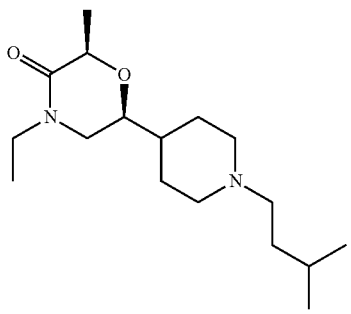 [SMILES: CCN1C[C@H](C2CCN(CCC(C)C)CC2)O[C@H](C)C1=O] | (2R,6S)-4-ethyl-6-(1-isopentylpiperidin-4-yl)-2-methylmorpholin-3-one |

| | | |
|---|---|---|
| 52 | 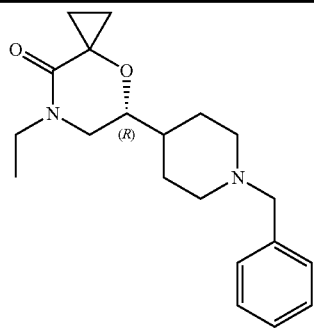 | (R)-5-(1-Benzylpiperidin-4-yl)-7-ethyl-4-oxa-7-azaspiro[2.5]octan-8-one |
| 53 | 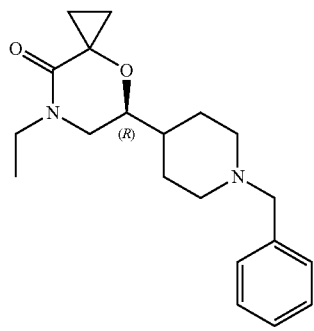 | (S)-5-(1-benzylpiperidin-4-yl)-7-ethyl-4-oxa-7-azaspiro[2.5]octan-8-one |
| 54 | 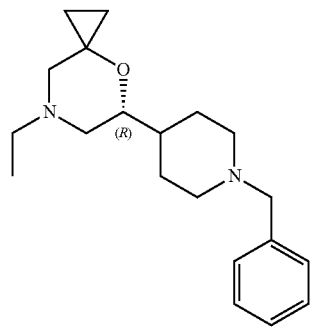 | (R)-5-(1-Benzylpiperidin-4-yl)-7-ethyl-4-oxa-7-azaspiro[2.5]octane |
| 55 | 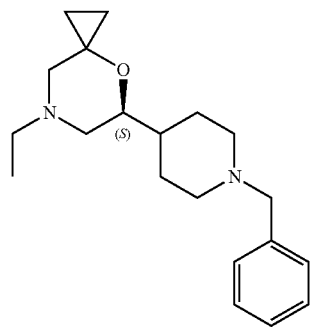 | (S)-5-(1-benzylpiperidin-4-yl)-7-ethyl-4-oxa-7-azaspiro[2.5]octane |
| 56 | 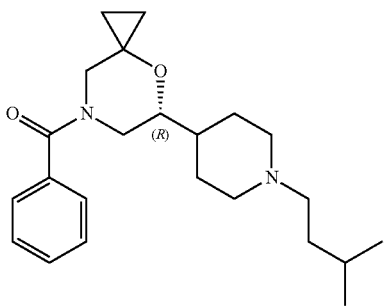 | (R)-(5-(1-isopentylpiperidin-4-yl)-4-oxa-7-azaspiro[2.5]octan-7-yl)(phenyl)methanone |

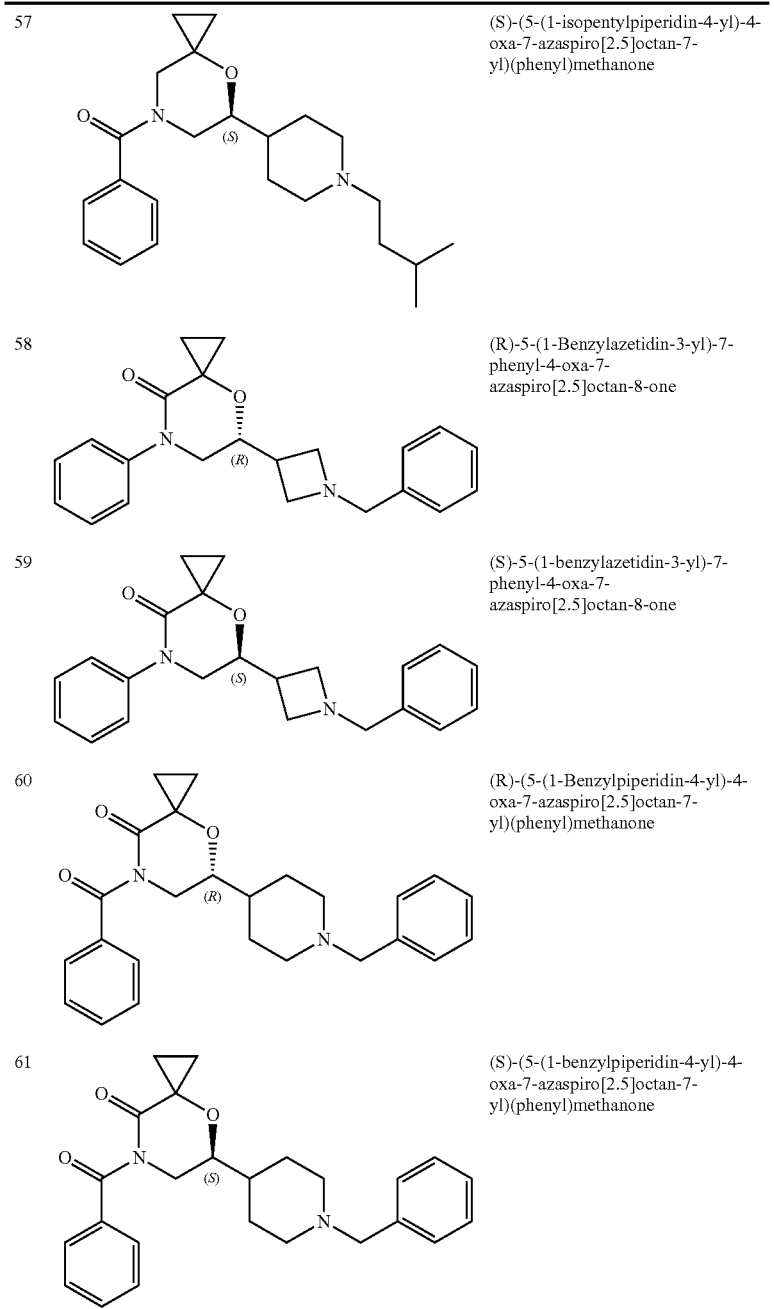

| 57 | (S)-(5-(1-isopentylpiperidin-4-yl)-4-oxa-7-azaspiro[2.5]octan-7-yl)(phenyl)methanone |
| 58 | (R)-5-(1-Benzylazetidin-3-yl)-7-phenyl-4-oxa-7-azaspiro[2.5]octan-8-one |
| 59 | (S)-5-(1-benzylazetidin-3-yl)-7-phenyl-4-oxa-7-azaspiro[2.5]octan-8-one |
| 60 | (R)-(5-(1-Benzylpiperidin-4-yl)-4-oxa-7-azaspiro[2.5]octan-7-yl)(phenyl)methanone |
| 61 | (S)-(5-(1-benzylpiperidin-4-yl)-4-oxa-7-azaspiro[2.5]octan-7-yl)(phenyl)methanone | optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I), $R_{1'}$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;

wherein said cycloalkyl, aryl or heterocyclyl in $R_{1'}$ if substituted, is substituted with one or more substituent/s selected from halogen, —$R_{11}$, —$OR_{11}$, —$NR_2$, —$NR_{11}R_{11'''}$, $NR_{11}C(O)R_{11'}$, —$NR_{11}S(O)_2R_{11'}$, —$S(O)_2NR_{11}R_{11'}$, —$NR_{11}C(O)NR_{11'}R_{11''}$, —$SR_{11}$, —$S(O)R_{11}$, $S(O)_2R_{11}$, —CN, haloalkyl, haloalkoxy, —$C(O)OR_{11}$, —$C(O)NR_{11}R_{11'}$, —$OCH_2CH_2OH$, —$NR_{11}S(O)_2NR_{11'}R_{11''}$ and $C(CH_3)_2OR_{11}$;

additionally, the cycloalkyl or non-aromatic heterocyclyl in $R_{1'}$ if substituted, may also be substituted with

or =O;
wherein the alkyl, alkenyl or alkynyl in $R_{1''}$, if substituted, is substituted with one or more substituent/s selected from —$OR_{11}$, halogen, —CN, haloalkyl, haloalkoxy and —$NR_{11}R_{11'''}$;
wherein $R_{11}$, $R_{11'}$ and $R_{11''}$ are independently selected from hydrogen, unsubstituted $C_{1-6}$ alkyl, unsubstituted $C_{2-6}$ alkenyl and unsubstituted $C_{2-6}$ alkynyl;
and wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment of the invention the compound of general Formula (I),
$R_2$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl,
wherein said cycloalkyl, aryl or heterocyclyl in $R_2$, if substituted, is substituted with one or more substituent/s selected from halogen, —$R_{12}$, —$OR_{12}$, —$NR_2$, —$NR_{12}R_{12'''}$, $NR_{12}C(O)R_{12'}$, —$NR_{12}S(O)_2R_{12'}$, —$S(O)_2NR_{12}R_{12'}$, —$NR_{12}C(O)NR_{12'}R_{12'}$, —$SR_{12}$, —$S(O)R_{12}$, $S(O)_2R_{12}$, —CN, haloalkyl, haloalkoxy, —$C(O)OR_{12}$, —$C(O)NR_{12}R_{12'}$, —$OCH_2CH_2OH$, —$NR_{12}S(O)_2NR_{12'}R_{12''}$ and $C(CH_3)_2OR_{12}$;
additionally, the cycloalkyl or non-aromatic heterocyclyl in $R_2$, if substituted, may also be substituted with

or =O;
wherein the alkyl, alkenyl or alkynyl in $R_2$, if substituted, is substituted with one or more substituent/s selected from —$OR_{12}$, halogen, —CN, haloalkyl, haloalkoxy and —$NR_{12}R_{12'''}$;
wherein $R_{12}$, $R_{12'}$ and $R_{12''}$ are independently selected from hydrogen, unsubstituted $C_{1-6}$ alkyl, unsubstituted $C_{2-6}$ alkenyl and unsubstituted $C_{2-6}$ alkynyl;
and wherein $R_{12'''}$ is selected from hydrogen, unsubstituted $C_{1-6}$ alkyl, unsubstituted $C_{2-6}$ alkenyl, unsubstituted $C_{2-6}$ alkynyl and -Boc;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment of the invention the compound of general Formula (I), the alkyl, alkenyl or alkynyl, other than those defined in $R_{1'}$ or $R_2$, if substituted, is substituted with one or more substituent/s selected from —$OR_{13}$, halogen, —CN, haloalkyl, haloalkoxy and —$NR_{13}R_{13'''}$;

wherein $R_{13}$, are independently selected from hydrogen, unsubstituted $C_{1-6}$ alkyl, unsubstituted $C_{2-6}$ alkenyl, and unsubstituted $C_{2-6}$ alkynyl;
$R_{13'''}$ is selected from hydrogen, unsubstituted $C_{1-6}$ alkyl, unsubstituted $C_{2-6}$ alkenyl, unsubstituted $C_{2-6}$ alkynyl and -Boc;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding-salt thereof, or a corresponding solvate thereof.

In another embodiment of the invention the compound of general Formula (I),
the aryl, heterocyclyl or cycloalkyl other than those defined in $R_{1'}$ or $R_2$, if substituted, is substituted with one or more substituent/s selected from halogen, —$R_{14}$, —$OR_{14}$, —$NO_2$, —$NR_{14}R_{14'''}$, $NR_{14}C(O)R_{14'}$, —$NR_{14}S(O)_2R_{14'}$, —$S(O)_2NR_{14}R_{14'}$, —$NR_{14}C(O)NR_{14'}R_{14''}$, —$SR_{14}$, —$S(O)R_{14}$, $S(O)_2R_{14}$, —CN, haloalkyl, haloalkoxy, —$C(O)OR_{14}$, —$C(O)NR_{14}R_{14'}$, —$OCH_2CH_2OH$, —$NR_{14}S(O)_2NR_{14}R_{14''}$ and $C(CH_3)_2OR_{14}$;
additionally, wherein the cycloalkyl or non-aromatic heterocyclyl, other than those defined in $R_{1''}$ or $R_2$, if substituted, may also be substituted with

or =O;
wherein $R_{14}$, $R_{14'}$ and $R_{14''}$ are independently selected from hydrogen, unsubstituted $C_{1-6}$alkyl, unsubstituted $C_{2-6}$ alkenyl, unsubstituted $C_{2-6}$ alkynyl, unsubstituted aryl, unsubstituted cycloalkyl and unsubstituted heterocyclyl;
and wherein $R_{14'''}$ is selected from hydrogen, unsubstituted $C_{1-6}$ alkyl, unsubstituted $C_{2-6}$ alkenyl, unsubstituted $C_{2-6}$ alkynyl and -Boc;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_{1'}$ of any of the embodiments of the present invention,
the cycloalkyl, aryl or heterocyclyl in $R_{1'}$ if substituted, is substituted with one or more substituents selected from halogen, —$R_{11}$, —$OR_{11}$, —$NR_2$, —$NR_{11}R_{11'''}$, $NR_{11}C(O)R_{11'}$, —$NR_{11}S(O)_2R_{11'}$, —$S(O)_2NR_{11}R_{11'}$, —$NR_{11}C(O)NR_{11'}R_{11''}$, —$SR_{11}$, —$S(O)R_{11}$, $S(O)_2R_{11}$, —CN, haloalkyl, haloalkoxy, —$C(O)OR_{11}$, —$C(O)NR_{11}R_{11'}$, —$OCH_2CH_2OH$, —$NR_{11}S(O)_2NR_{11'}R_{11''}$ and $C(CH_3)_2OR_{11}$;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_{1'}$ of any of the embodiments of the present invention, the cycloalkyl or non-aromatic heterocyclyl in $R_{1'}$ if substituted; may also be substituted with

or =O;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_{1'}$ of any of the embodiments of the present invention, the aryl in $R_{1'}$ if substituted, is substituted with —$OR_{11}$; wherein the aryl is phenyl and $R_{11}$ is substituted or unsubstituted methyl; $R_{11}$ is preferably unsubstituted methyl;

optionally in form of one of the stereoisomers, preferably enantiomers or diastereomers, a racemate or in form of a mixture of at least two of the stereoisomers, preferably enantiomers, and/or diastereomers, in any mixing ratio, or a corresponding salt thereof, or a corresponding solvate thereof.

In a preferred embodiment of the compound according to the invention of general Formula (I) and in relation to $R_{1'}$ of any of the embodiments of the present invention, the alkyl, alkenyl or alkynyl in $R_{1'}$ if substituted, is substituted with one or more substituent/s selected from —$OR_{11}$, halogen, —CN, haloalkyl, haloalkoxy and —$NR_{11}R_{11'''}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in, relation to $R_2$ of any of the embodiments of the present invention, the cycloalkyl, aryl or heterocyclyl in $R_2$, if substituted, is substituted with one or more substituent/s selected from halogen, —$R_{12}$, —$OR_{12}$, —$NR_2$, —$NR_{12}R_{12'''}$, —$NR_{12}C(O)R_{12'}$, —$NR_{12}S(O)_2R_{12'}$, —$S(O)_2NR_{12}R_{12'}$, —$NR_{12}C(O)NR_{12'}R_{12'''}$, —$SR_{12}$, —$S(O)R_{12'}$, $S(O)_2R_{12'}$, —CN, haloalkyl, haloalkoxy, —$C(O)OR_{12'}$, —$C(O)NR_{12}R_{12'}$, —$OCH_2CH_2OH$, —$NR_{12}S(O)_2NR_{12'}R_{12''}$ and $C(CH_3)_2OR_{12}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_2$ of any of the embodiments of the present invention, the cycloalkyl or non-aromatic heterocyclyl in $R_2$, if substituted, may also be substituted with

or =O;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_2$ of any of the embodiments of the present invention, the aryl in $R_2$, if substituted, is substituted with halogen or —CN; wherein the aryl is phenyl and the halogen is fluorine;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_2$ of any of the embodiments of the present invention, the alkyl, alkenyl or alkynyl in $R_2$, if substituted, is substituted with one or more substituent/s selected from —$OR_{12}$, halogen, —CN, haloalkyl, haloalkoxy and —$NR_{12}R_{12'''}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to alkyls other than those defined in $R_{1'}$ or $R_2$ of any of the embodiments of the present invention, the alkyl, alkenyl or alkynyl, other than those defined in $R_{1'}$ or $R_2$, if substituted, is substituted with one or more substituent/s selected from —$OR_{13}$, halogen, —CN, haloalkyl, haloalkoxy and —$NR_{13}R_{13'''}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to the cycloalkyl, aryl or heterocyclyl other than those defined in $R_{1'}$ or $R_2$ of any of the embodiments of the present invention, the aryl, heterocyclyl or cycloalkyl other than those defined in $R_{1'}$ or $R_2$, if substituted, is substituted with one or more substituent/s selected from halogen, —$R_{14}$, —$OR_{14}$, —$NR_2$, —$NR_{14}R_{14'''}$, —$NR_{14}C(O)R_{14'}$, —$NR_{14}S(O)_2R_{14'}$, —$S(O)_2NR_{14}R_{14'}$, —$NR_{14}C(O)NR_{14'}R_{14'''}$, —$SR_{14}$, —$S(O)R_{14}$, $S(O)_2R_{14}$, —CN, haloalkyl, haloalkoxy, —$C(O)OR_{14}$, —$C(O)NR_{14}R_{14'}$, —$OCH_2CH_2OH$, —$NR_{14}S(O)_2NR_{14}R_{14''}$ and $C(CH_3)_2OR_{14}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to the cycloalkyl, aryl or heterocyclyl other than those defined in $R_{1'}$ or $R_2$ of any of the embodiments of the present invention, the cycloalkyl or non-aromatic heterocyclyl, other than those defined in $R_{1'}$ or $R_2$, if substituted, may also be substituted with

or =O;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In an embodiment of the compound according to the invention of general Formula (I), the halogen is fluorine, chlorine, iodine or bromine, preferably fluorine or chlorine;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In an embodiment of the compound according to the invention of general Formula (I), the halogen is fluorine, chlorine, iodine or bromine, preferably fluorine or chlorine; more preferably fluorine:

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In an embodiment of the compound according to the invention of general Formula (I), the haloalkyl is —$CF_3$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment of the compound according to the invention of general Formula (I), the haloalkoxy is —$OCF_3$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

As this invention is aimed at providing a compound or a chemically related series of compounds which act as ligands of the $\sigma_1$ receptor it is a very preferred embodiment in which the compounds are selected which act as ligands of the $\sigma_1$ receptor and especially compounds which have a binding expressed as $K_i$ which is preferably <1000 nM, more preferably <500 nM, even more preferably <100 nM.

In the following the phrase "compound of the invention" is used. This is to be understood as any compound according to the invention as described above according to general Formula (I), (I'), (I²'), (I³'), (I⁴'), (I⁵'), (I⁶'), (I⁴ᵃ'), (I⁵ᵃ'), (I⁶ᵃ'), (I⁴ᵇ'), (I⁵ᵇ'), (I⁶ᵇ') (I⁴ᶜ'), (I⁵ᶜ') (I⁶ᶜ') and also (I⁷').

The compounds of the invention represented by the above described Formula (I) may include enantiomers depending on the presence of chiral centres or isomers depending on the presence of multiple bonds (e.g. Z, E).

The single isomers, enantiomers or diastereoisomers and mixtures thereof fall within the scope of the present invention.

For the sake of clarity the expression "a compound according to Formula (I), wherein $R_1$, $R_2$, $R_3$, $R_{3'}$, $R_5$, $R_{5'}$, $R_6$, $R_{6'}$, X, Y, q, r, m and n are as defined in the description in the detailed description" would (just like the expression "a compound of Formula (I) as defined in any one of claims 1 to 11" found in the claims) refer to "a compound according to Formula (I)", wherein the definitions of the respective substituents $R_1$ etc. (also from the cited claims) are applied. In addition, this would also mean, though (especially in regards to the claims) that also one or more disclaimers defined in the description (or used in any of the cited claims like e.g. claim 1) would be applicable to define the respective compound. Thus, a disclaimer found in e.g. claim 1 would be also used to define the compound "of Formula (I) as defined in any one of claims 1 to 11".

In general the processes are described below in the experimental part. The starting materials are commercially available or can be prepared by conventional methods.

A preferred aspect of the invention is also a process for the production of a compound according to Formula (I).

A preferred aspect of the invention is a process for the production of a compound according to Formula (I),

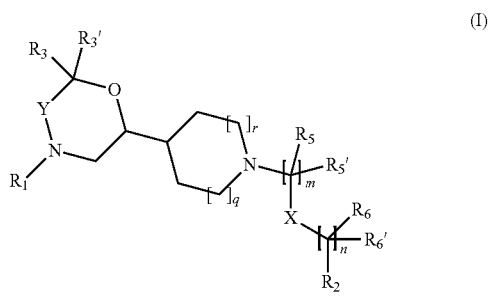

and wherein $R_1$, $R_2$, $R_3$, $R_{3'}$, $R_5$, $R_{5'}$, $R_6$, $R_{6'}$, m, n, q, r, X and Y are as defined in the description, following schemes 1 to 4.

In all processes and uses described underneath, the values of $R_1$, $R_{1'}$, $R_2$, $R_3$, $R_{3'}$, $R_4$, $R_{4'}$, $R_5$, $R_{5'}$, $R_6$, $R_{6'}$, m, n, p, q, r, X and Y are as defined in the description (unless otherwise stated), LG represents a leaving, group, such such as halogen, mesylate, tosylate or triflate, with the proviso that when Y=CO it can only be chloro or bromo, W represents an aldehyde or another leaving group (such as halogen, mesylate, tosylate or triflate), P represents a suitable protecting group (preferably Boc) and P' represents an orthogonal protecting group (preferably 4-methoxybenzyl or benzyl).

A preferred embodiment of the invention is a process for the production of a compound according to Formula (I), wherein $R_1$ is —$(CR_4R_{4'})_pR_{1'}$ (compound of formula Ia), said process comprises:

a) the intramolecular cyclization of a compound of formula VII

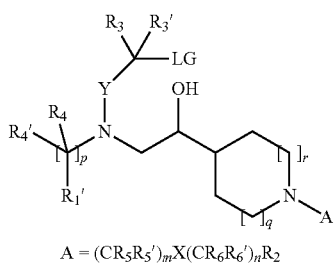

A = (CR$_5$R$_5'$)$_m$X(CR$_6$R$_6'$)$_n$R$_2$ or b) the reaction of a compound of formula VIIIH

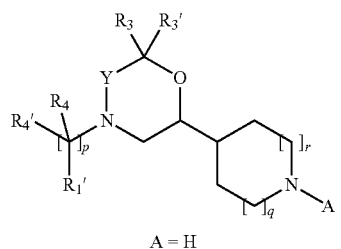

A = H with a compound of formula IX, X or XI,

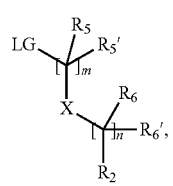

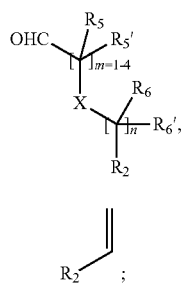

or c1) when Y is CH$_2$, by the alkylation of a compound of formula XIII

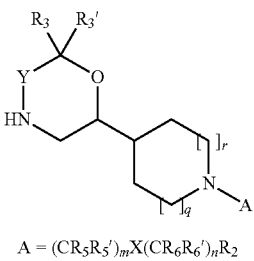

A = (CR$_5$R$_5'$)$_m$X(CR$_6$R$_6'$)$_n$R$_2$ with a compound of formula IV

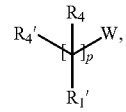

being the compound of formula IV an alkylating agent and W a leaving group, or alternatively by the reductive amination reaction of a compound of formula XIII with a compound of formula IV, being the compound of formula IV an aldehyde or ketone and W a C(O)H or C(O) group;

or c2) when Y is C(O), by the alkylation of a compound of formula XIII

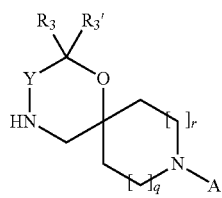

A = (CR$_5$R$_5'$)$_m$X(CR$_6$R$_6'$)$_n$R$_2$ with a compound of formula IV

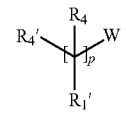

being the compound of formula IV an alkylating agent and W a leaving group.

A preferred embodiment of the invention is a process for the production of a compound according to Formula (I), wherein R$_1$ is —(CR$_4$R$_4'$)$_p$R$_1'$ (compound of formula Ia), said process comprises the intramolecular cyclization of a compound of formula VII

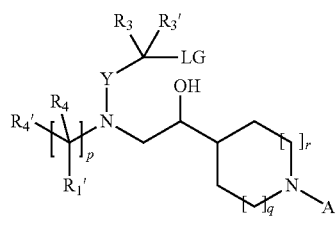

VII

A = (CR$_5$R$_5'$)$_m$X(CR$_6$R$_6'$)$_n$R$_2$

A preferred embodiment of the invention is a process for the production of a compound according to Formula (I), wherein R, is —(CR$_4$R$_4'$)$_p$R$_1'$ (compound of formula Ia), said process comprises the reaction of a compound of formula VIIIH

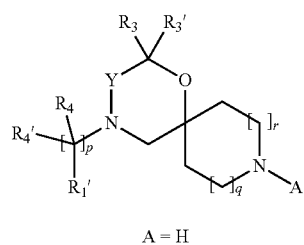

VIIIH

A = H with a compound of formula IX, X or XI,

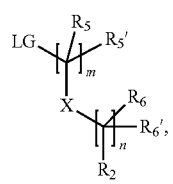

IX

X

XI

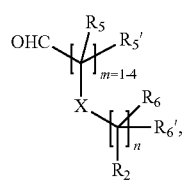

A preferred embodiment of the invention is a process for the production of a compound according to Formula (I), wherein R, is —(CR$_4$R$_4'$)$_p$R$_1'$ (compound of formula Ia) and when Y is CH$_2$, said process comprises the alkylation of a compound of formula XIII

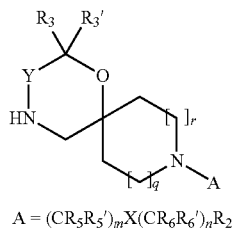

XIII

A = (CR$_5$R$_5'$)$_m$X(CR$_6$R$_6'$)$_n$R$_2$ with a compound of formula IV

IV

R$_4'$—(R$_4$)$_p$—W,
  |
  R$_1'$ being the compound of formula IV an alkylating agent and W a leaving group, or alternatively by the reductive amination reaction of a compound of formula XIII with a compound of formula IV, being the compound of formula IV an aldehyde or ketone and W a C(O)H or C(O) group.

A preferred embodiment of the invention is a process for the production of a compound according to Formula (I), wherein R$_1$ is —(CR$_4$R$_4'$)$_p$R$_1'$ and Y is C(O), said process comprises the alkylation of a compound of formula XIII

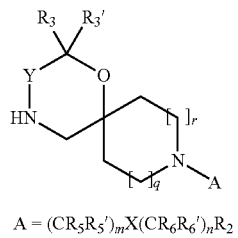

XIII

A = (CR$_5$R$_5'$)$_m$X(CR$_6$R$_6'$)$_n$R$_2$ with a compound of formula IV

IV

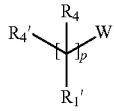

being the compound of formula IV an alkylating agent and W a leaving group.

In another preferred embodiment of the invention is a process for the preparation, of compounds of general formula (I) wherein R$_1$ is —(CR$_4$R$_4'$)$_p$R$_1'$, Y represents CO and R$_3$ and R$_3'$ taken together with the connecting C-atom form a cyclopropyl (compounds of formula Id), said process comprises a) a cyclopropanation reaction of compounds of formula XXI

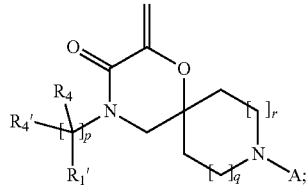

XXI

A = (CR$_5$R$_5'$)$_m$X(CR$_6$R$_6'$)$_n$R$_2$ or b) the treatment of a compound of formula Ic, wherein s is 1, and R$_s$ and R$_{s'}$ are hydrogen

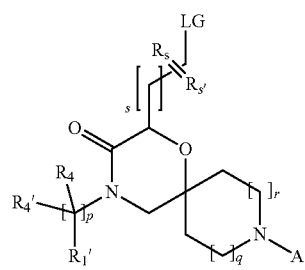

Ic

A = (CR$_5$R$_5'$)$_m$X(CR$_6$R$_6'$)$_n$R$_2$ with a strong base in an aprotic solvent, at a suitable temperature;

or c) the reaction of a compound of formula XXV

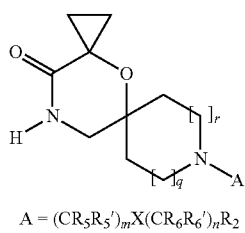

XXV

A = (CR$_5$R$_5'$)$_m$X(CR$_6$R$_6'$)$_n$R$_2$ with a compound of formula IV

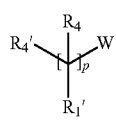

IV or d) the reaction of a compound of formula XIXH

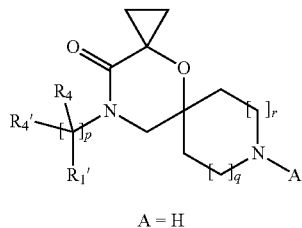

XIXH

A = H with a compound of formula IX, X or XI

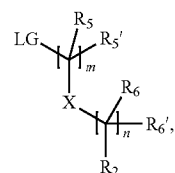

IX

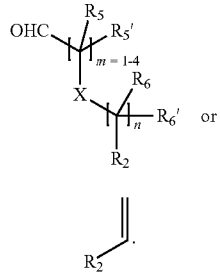

X

XI

In another preferred embodiment of the invention is a process for the preparation, of compounds of general formula (I) wherein R$_1$ is —(CR$_4$R$_{4'}$)$_p$R$_{1'}$, Y represents CO and R$_3$ and R$_{3'}$ taken together with the connecting C-atom form a cyclopropyl (compounds of formula Id), said process comprises a cyclopropanation reaction of compounds of formula XXI

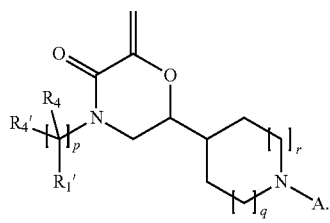

XXI

A = (CR$_5$R$_5'$)$_m$X(CR$_6$R$_6'$)$_n$R$_2$

In another preferred embodiment of the invention is a process for the preparation, of compounds of general formula (I) wherein R$_1$ is —(CR$_4$R$_{4'}$)$_p$R$_{1'}$, Y represents CO and R$_3$ and R$_{3'}$ taken together with the connecting C-atom form a cyclopropyl (compounds of formula Id), said process comprises the treatment of a compound of formula Ic, wherein s is 1, and R$_s$ and R$_{s'}$ are hydrogen

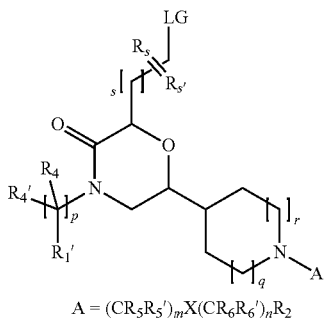

Ic

A = (CR₅R₅')ₘX(CR₆R₆')ₙR₂ with a strong base in an aprotic solvent, at a suitable temperature.

In another preferred embodiment of the invention is a process for the preparation, of compounds of general formula (I) wherein $R_1$ is —$(CR_4R_{4'})_pR_{1'}$, Y represents CO and $R_3$ and $R_{3'}$ taken together with the connecting C-atom form a cyclopropyl (compounds of formula Id), said process comprises the reaction of a compound of formula XXV

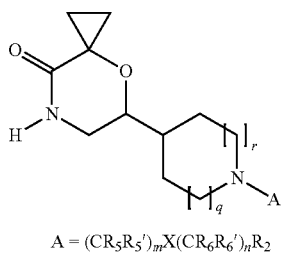

XXV

A = (CR₅R₅')ₘX(CR₆R₆')ₙR₂ with a compound of formula. IV

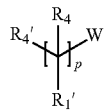

IV

In another preferred embodiment of the invention is a process, for the preparation, of compounds of general formula (I) wherein $R_1$ is —$(CR_4R_{4'})_pR_{1'}$, Y represents CO and $R_3$ and $R_{3'}$ taken together with the connecting C-atom form a cyclopropyl (compounds of formula Id), said process comprises the reaction of a compound of formula XIXH

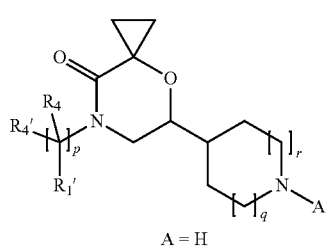

XIXH

A = H with a compound of formula IX, X or XI

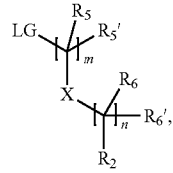

IX

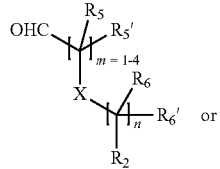

X or

XI

In another particular embodiment a compound of Formula Ia, II, IIP, III, IIIP, IV, V, VP, VI, VII, VIIP, VIIIP, VIIIH, IX, X, XI, XII, XIIP, XIII, XIIIP, XIIIH, XIV, XIVP, XV, XVP, XVI, XVIP, XVIH, Ib, XVIIP, XVIIH, Ic, XVIIIP, Id, XIXP, XIXH, Ie, XXP, XXH, XXI, XXIP, XXIH, XXII, XXIIP, XXIIH, XXIII, XXIIIP, XXIIIH, XXIV, XXIVP, XXIVH, XXV, XXVP, XXVH, If, XXVIP, XXVIH, XXVIIa, XXVIIb, XXVIIc, Ig, XXVIIIP, XXVIIIH, Ih, XXIXP, XXIXH, Ii, XXXP, XXXH, XXXI, XXXIP, XXXIH, XXXII, XXXIIP, XXXIIH, XXXIII, XXXIIIP, XXXIIIH, XXXIV, XXXIVP, XXXIVH, XXXV, Ij, XXXVIP or XXXVIH,

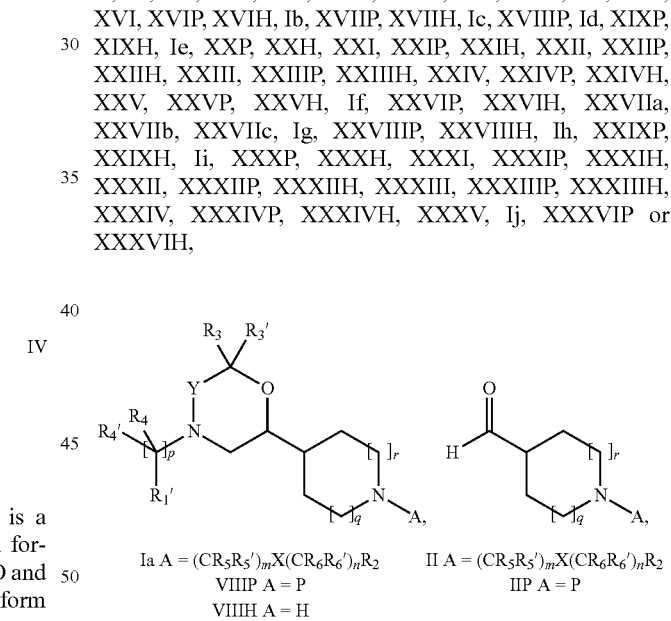

Ia A = (CR₅R₅')ₘX(CR₆R₆')ₙR₂
VIIIP A = P
VIIIH A = H

II A = (CR₅R₅')ₘX(CR₆R₆')ₙR₂
IIP A = P

III A = (CR₅R₅')ₘX(CR₆R₆')ₙR₂
IIIP A = P

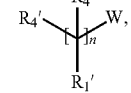

IV

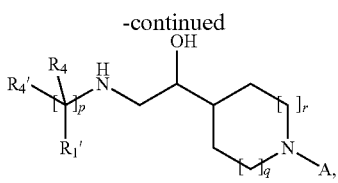
V A = (CR_5R_5')_mX(CR_6R_6')_nR_2
VP A = P
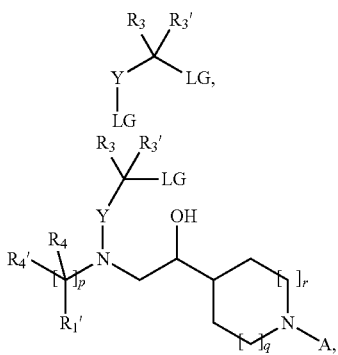
VII A = (CR_5R_5')_mX(CR_6R_6')_nR_2
VIIP A = P
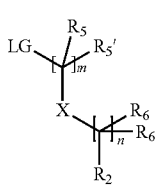
IX
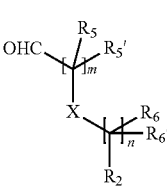
X
XI
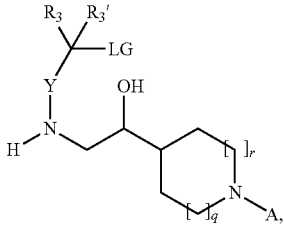
XII A = (CR_5R_5')_mX(CR_6R_6')_nR_2
XIIP A = P
XIII A = (CR_5R_5')_mX(CR_6R_6')_nR_2
XIIIP A = P
XIIIH A = H
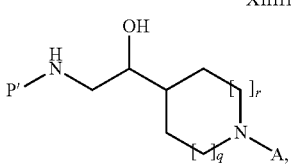
XIV A = (CR_5R_5')_mX(CR_6R_6')_nR_2
XIVP A = P
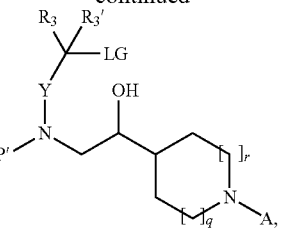
XV A = (CR_5R_5')_mX(CR_6R_6')_nR_2
XVP A = P
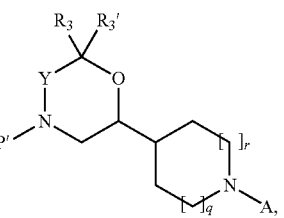
XVI A = (CR_5R_5')_mX(CR_6R_6')_nR_2
XVIP A = P
XVIH A = H
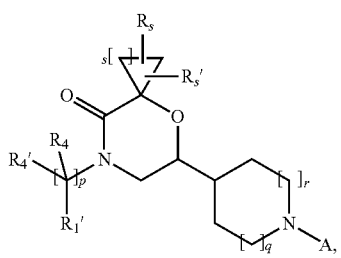
Ib A = (CR_5R_5')_mX(CR_6R_6')_nR_2
XVIIP A = P
XVIIH A = H
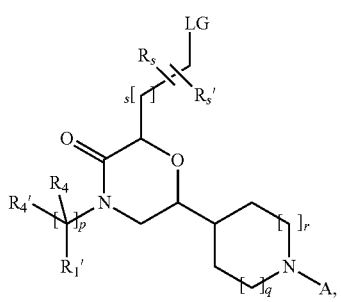
Ic A = (CR_5R_5')_mX(CR_6R_6')_nR_2
XVIIIP A = P
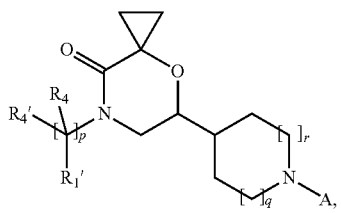
Id A = (CR_5R_5')_mX(CR_6R_6')_nR_2
XIXP A = P
XIXH A = H -continued

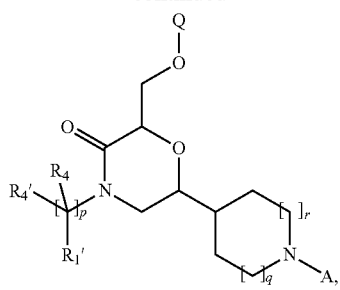

Ie A = (CR$_5$R$_5'$)$_m$X(CR$_6$R$_6'$)$_n$R$_2$
XXP A = P
XXH A = H

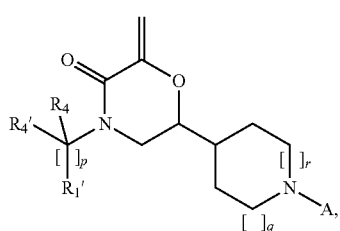

XXe A = (CR$_5$R$_5'$)$_m$X(CR$_6$R$_6'$)$_n$R$_2$
XXIP A = P
XXIH A = H

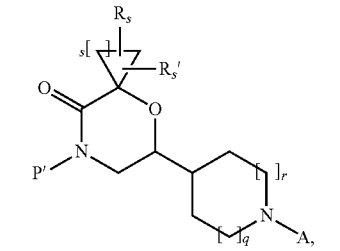

XXII A = (CR$_5$R$_5'$)$_m$X(CR$_6$R$_6'$)$_n$R$_2$
XXIIP A = P
XXIIH A = H

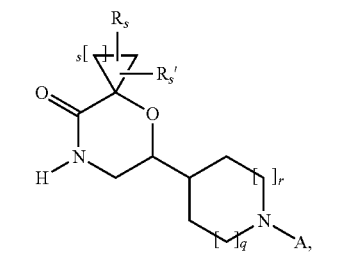

XXIII A = (CR$_5$R$_5'$)$_m$X(CR$_6$R$_6'$)$_n$R$_2$
XXIIIP A = P
XXIIIH A = H

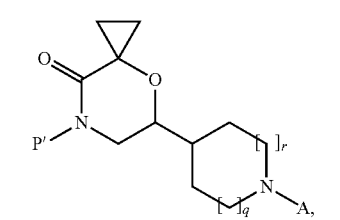

XXIVA = (CR$_5$R$_5'$)$_m$X(CR$_6$R$_6'$)$_n$R$_2$
XXIVP A = P
XXIVH A = H

-continued

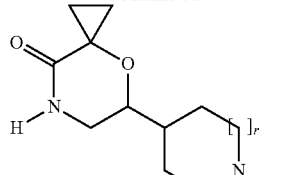

XXV A = (CR$_5$R$_5'$)$_m$X(CR$_6$R$_6'$)$_n$R$_2$
XXVP A = P
XXVH A = H

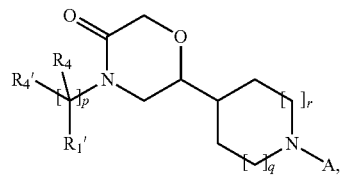

If A = (CR$_5$R$_5'$)$_m$X(CR$_6$R$_6'$)$_n$R$_2$
XXVIP A = P
XXIIIH A = H

R$_3$X',  XXVIIa

R$_3'$X',  XXVIIb

XXVIIc

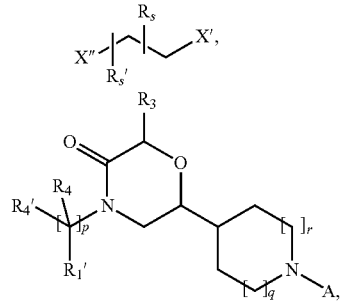

Ig A = (CR$_5$R$_5'$)$_m$X(CR$_6$R$_6'$)$_n$R$_2$
XVIIIP A = P
XVIIIH A = H

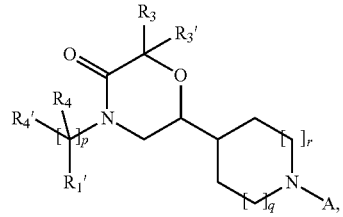

Ih A = (CR$_5$R$_5'$)$_m$X(CR$_6$R$_6'$)$_n$R$_2$
XXIXP A = P
XXIXH A = H

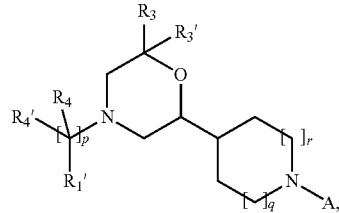

Ii A = (CR$_5$R$_5'$)$_m$X(CR$_6$R$_6'$)$_n$R$_2$
XXXP A = P
XXXH A = H

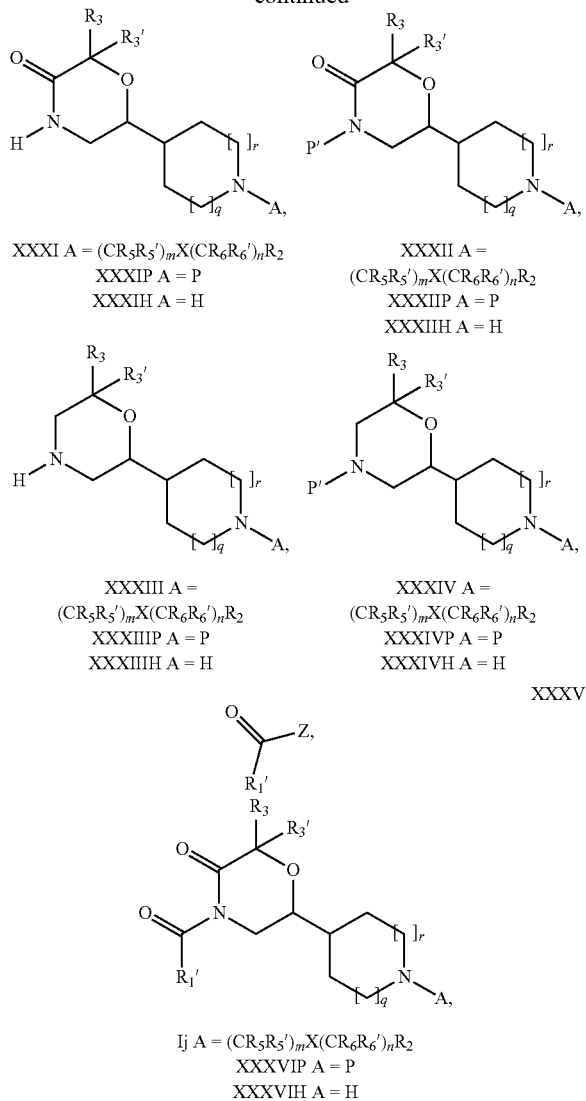

is used for the preparation of a compound of Formula (I).

The obtained reaction products may, if desired, be purified by conventional methods, such as crystallisation and chromatography. Where the above described processes for the preparation of compounds of the invention give rise to mixtures of stereoisomers, these, isomers may be separated by conventional techniques such as preparative chromatography. If there are chiral centers the compounds may be prepared in racemic form, or individual enantiomers may be prepared either by enantiospecific, synthesis or by resolution.

One preferred pharmaceutically acceptable form of a compound of the invention is the crystalline form, including such form in pharmaceutical composition. In the case of salts and also solvates of the compounds of the invention the additional ionic and solvent moieties must also be non-toxic. The compounds of the invention may present different polymorphic forms, it is intended that the invention encompasses all such forms.

Another aspect of the invention refers to a pharmaceutical composition which comprises a compound according to the invention as described above according to general formula I or a pharmaceutically acceptable salt or stereoisomer thereof, and a pharmaceutically acceptable carrier, adjuvant or vehicle. The present invention thus provides pharmaceutical compositions comprising a compound of this invention, or a pharmaceutically acceptable salt or stereoisomers thereof together with a pharmaceutically acceptable carrier, adjuvant, or vehicle, for administration to a patient.

Examples of pharmaceutical compositions include any solid (tablets; pills, capsules, granules etc.) or liquid (solutions, suspensions or emulsions) composition for oral, topical or parenteral administration.

In a preferred embodiment the pharmaceutical compositions are in oral form, either solid or liquid. Suitable dose forms for oral administration may be tablets, capsules, syrops or solutions and may contain conventional excipients known in the art such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulfate.

The solid oral compositions may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to methods well known in normal pharmaceutical practice, in particular with an enteric coating.

The pharmaceutical compositions may also be adapted for parenteral administration, such as sterile solutions, suspensions or lyophilized products in the appropriate unit dosage form. Adequate excipients can be used, such as bulking agents, buffering agents or surfactants.

The mentioned formulations will be prepared using standard methods such as those described or referred to in the Spanish and US Pharmacopoeias and similar reference texts.

Administration of the compounds or compositions of the present invention may be by any suitable method, such as intravenous infusion, oral preparations, and intraperitoneal and intravenous administration. Oral administration is preferred because of the convenience for the patient and the chronic character of the diseases to be treated.

Generally an effective administered amount of a compound of the invention will depend on the relative efficacy of the compound chosen, the severity of the disorder being treated and the weight of the sufferer. However, active compounds will typically be administered once or more times a day for example 1, 2, 3 or 4 times daily, with typical total daily doses in the range of from 0.1 to 1000 mg/kg/day.

The compounds and compositions of this invention may be used with other drugs to provide a combination therapy. The other drugs may form part of the same composition, or be provided as a separate composition for administration at the same time or at different time.

Another aspect of the invention refers to the use of a compound, of the invention or a pharmaceutically acceptable salt or isomer thereof in the manufacture of a medicament.

Another aspect of the invention refers to a compound of the invention according as described above according to general formula I, or a pharmaceutically acceptable salt or isomer thereof, for use as a medicament for the treatment of pain. Preferably the pain is medium to severe pain, visceral pain, chronic pain, cancer pain, migraine, inflammatory pain, acute pain or neuropathic pain, allodynia or hyperalgesia. This may include mechanical allodynia or thermal hyperalgesia.

Another aspect of the invention refers to the use of a compound of the invention in the manufacture of a medicament for the treatment or prophylaxis of pain.

In a preferred embodiment the pain is selected from medium to severe pain, visceral pain, chronic pain, cancer pain, migraine, inflammatory pain, acute pain or neuropathic pain, allodynia or hyperalgesia, also preferably including mechanical allodynia or thermal hyperalgesia.

Another aspect of this invention relates to a method of treating or preventing pain which method comprises administering to a patient in need of such a treatment a therapeutically effective amount of a compound as above defined or a pharmaceutical composition thereof. Among the pain syndromes that can be treated are medium to severe pain, visceral pain, chronic pain, cancer pain, migraine, inflammatory pain, acute pain or neuropathic pain, allodynia or hyperalgesia, whereas this could also include mechanical allodynia or, thermal hyperalgesia.

The present invention is illustrated below with the aid of examples. These illustrations are given solely by way of example and do not limit the general spirit of the present invention.

General Experimental Part (Methods and Equipment of the Synthesis and Analysis

Scheme 1:

A 3-step process is described for the preparation of compounds of general formula (I) wherein $R_1$ is $—(CR_4R_{4'})_pR_{1'}$ (compounds of formula Ia) starting from a compound of formula II, as shown in the following scheme:

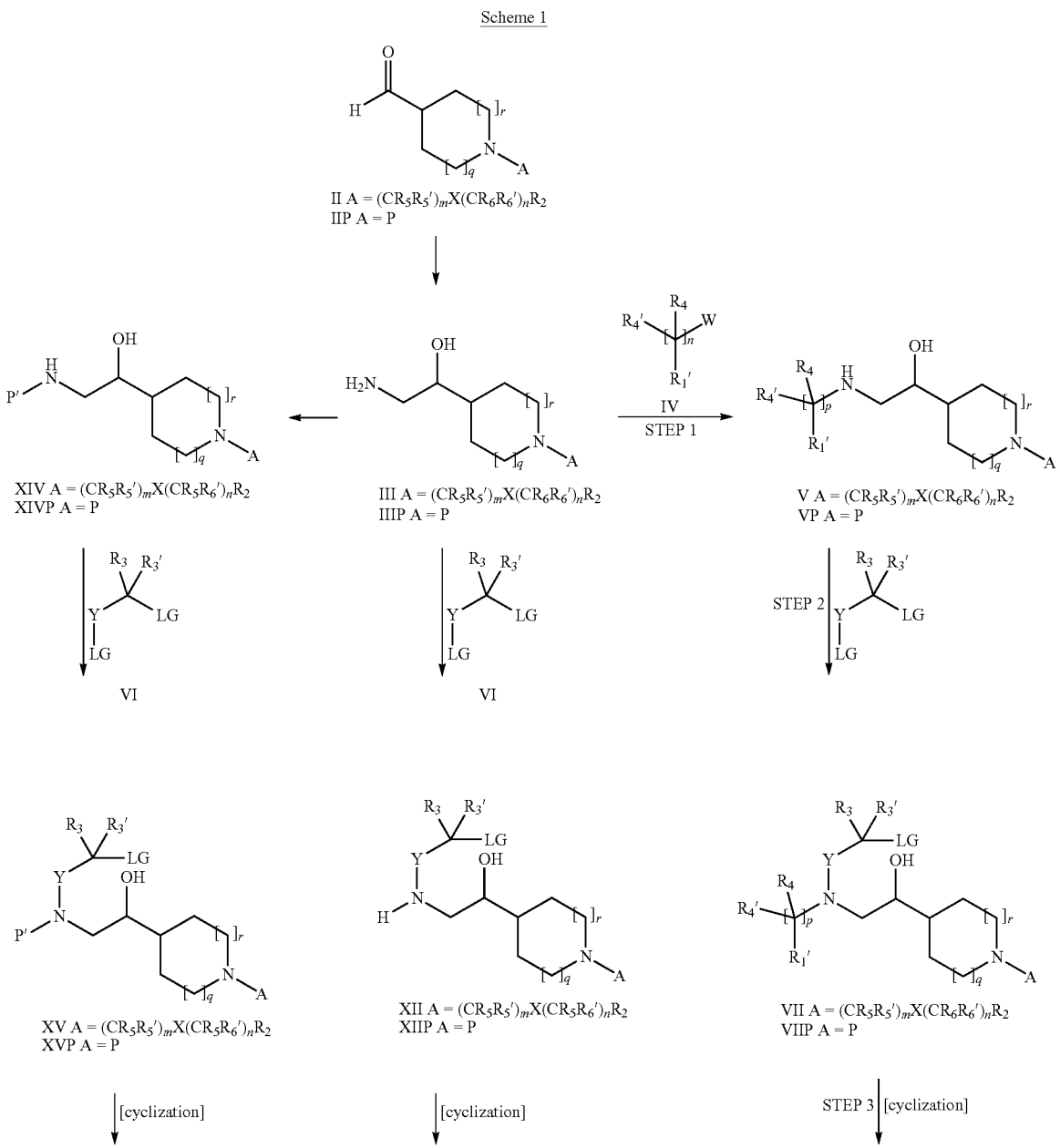

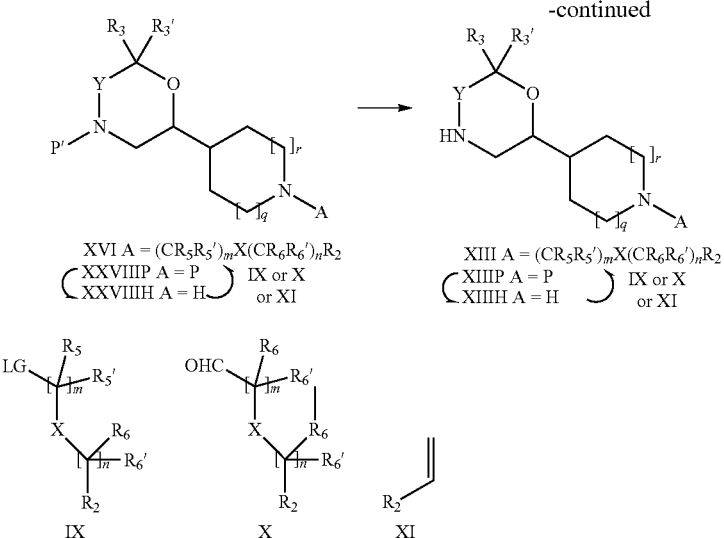

wherein $R_1'$, $R_2$, $R_3$, $R_3'$, $R_4$, $R_4'$, $R_5$, $R_5'$, $R_6$, $R_6'$, X, Y, m, n, p, q and r have the meanings as defined above for a compound of formula (I), LG represents a leaving group such as halogen, mesylate, tosylate or triflate, with the proviso that when Y=CO it can only be chloro or bromo, W represents an aldehyde or another leaving group (such as halogen, mesylate, tosylate or triflate), P represents a suitable protecting group (preferably Boc) and P' represents an orthogonal protecting group (preferably 4-methoxybenzyl or benzyl).

The 3 step-process is carried out as described below:

Step 1:

A compound of formula V is prepared by reacting a compound of formula III with a compound of formula IV wherein W can be of different nature and different reaction conditions will apply:

a) When W represents a leaving group such as halogen, mesylate, tosylate or triflate, compound IV is an alkylating agent. The alkylation reaction is carried out in a suitable solvent, such as ACN, dichloromethane, 1,4-dioxane or dimethylformamide; in the presence of an inorganic base such as $K_2CO_3$ or $Cs_2CO_3$, or an organic base such as triethylamine or diisopropylethylamine; at a suitable temperature comprised between room temperature and the reflux temperature, or alternatively, the reactions can be carried out in a microwave reactor. Additionally, an activating agent such as NaI can be used.

b) Alternatively, compound IV can be an aldehyde or ketone wherein W represents a C(O)—H or C(O) group. The reductive amination reaction between a compound of formula III and a compound of formula IV is carried out in the presence of a reductive reagent, preferably sodium triacetoxyborohydride, in an aprotic solvent, preferably tetrahydrofuran or dichloroethane, optionally in the presence of an acid, preferably acetic acid.

Step 2:

A compound of formula VII is prepared by reacting a compound of formula V with a compound of formula VI. Depending on the meaning of Y, the compound of formula VI can be of different nature and different reaction conditions will apply:

a) When Y represents CO, VI is an acylating agent. The acylation reaction is carried out in a suitable solvent, such as dichloromethane or ethyl acetate-water mixtures; in the presence of an organic base such as triethylamine or diisopropylethylamine or an inorganic base such as $K_2CO_3$; and at a suitable temperature, preferably comprised between −78° C. and room temperature.

b) When Y represents $CH_2$, VI is an alkylating agent. The alkylation reaction may be carried out under the same reaction conditions described above for the reaction of a compound of formula III and a compound of formula IV wherein W is a leaving group. The OH group present may need protection previous to the alkylation reaction.

Step 3:

The intramolecular cyclization of a compound of formula VII renders a compound of formula Ia. The cyclization reaction is carried out in a suitable solvent, such as tetrahydrofuran; in the presence of a strong base such as potassium tert-butoxide or sodium hydride; and at a suitable temperature, comprised between −78° C. and the reflux temperature, preferably cooling.

Alternatively, the group —$(CR_5R_5')_mX(CR_6R_6')_nR_2$ can be incorporated in the last step of the synthesis by reaction of a compound of formula VIIIH with a compound of formula IX, X or XI, as shown in Scheme 1. A compound of formula VIIIH is obtained by deprotection of a compound of formula VIIIP, wherein P represents a suitable protecting group, preferably Boc (tert-butoxycarbonyl). When the protecting group is Boc, the deprotection can be conducted by adding a solution of a strong acid such as HCl, in a suitable solvent such as diethyl ether, 1,4-dioxane or methanol, or with TFA in dichloromethane. A compound of formula VIIIP is prepared from a compound of formula IIIP following the same sequence described for the synthesis of compounds of formula Ia.

The alkylation reaction between a compound of formula VIIIH (or a suitable salt such as trifluoroacetate or hydrochloride) and a compound of formula IX is carried out under the same reaction conditions described above for the reaction of a compound of formula III and a compound of formula IV wherein W is a leaving group.

The reductive amination reaction between a compound of formula VIIIH (or a suitable salt) and a compound of formula X is carried out under the same reaction conditions described above for the reaction of a compound of formula III and a compound of formula IV wherein W is a C(O)—H group.

The condensation reaction between a compound of general formula VIIIH and a compound of formula XI is preferably carried out in a suitable solvent, such as ethanol, isopropanol, n-butanol or 2-methoxyethanol, optionally in the presence of an organic base such as triethylamine or diisopropylethylamine, at a suitable temperature comprised between room temperature and the reflux temperature, preferably heating, or alternatively, the reactions can be carried out in a microwave reactor.

In another alternative approach, the —(CR$_4$R$_{4'}$)$_p$R$_{1'}$ substituent can be incorporated later in the sequence by the reaction of a compound of formula XIII with a compound of formula IV. Depending on the meaning of Y, W can be of different nature and different reaction conditions will apply:

a) When Y is CH$_2$, compound IV is an alkylating agent and W represents a leaving group such as halogen, mesylate, tosylate or triflate. The alkylation reaction is carried out under the same reaction conditions described above for the reaction of a compound of formula III and a compound of formula IV.
   Alternatively, compound IV can be an aldehyde or ketone wherein W represents a C(O)—H or C(O) group. The reductive amination reaction is carried out under the same reaction conditions described above for the reaction of a compound of formula III and a compound of formula IV.

b) When Y is C(O), compound IV is an alkylating agent and W represents a leaving group such as halogen, mesylate, tosylate or triflate. This alkylation reaction is carried out in an aprotic solvent, preferably dimethylformamide, in the presence of an inorganic base such as NaH, at a suitable temperature, preferably at room temperature.

A compound of formula XIII is synthesized following an analogous sequence as described for the synthesis of compounds of formula Ia, but performing step 2 directly with a compound of formula III. Alternatively, when Y is C(O), a compound of formula XIII can be prepared by reaction of a compound of formula XIIIH (prepared from a compound of formula XIIIP, wherein P represents a suitable protecting group) with a compound of formula IX, X or XI, as described above.

Additionally, a compound of formula XIII can be prepared from a compound of formula XVI, wherein P' represents an orthogonal protecting group. When Y is C(O), P' is preferably a 4-methoxybenzyl group and the deprotection reaction is carried out with cerium ammonium nitrate in a suitable solvent such as mixtures of ACN-water or by heating in TFA or hydrochloric acid. When Y is —CH$_2$—, P' is preferably a 4-methoxybenzyl or a benzyl group, and the deprotection reaction is preferably carried out by hydrogenation under hydrogen atmosphere and metal catalysis, preferably by the use of palladium over charcoal as catalyst in a suitable solvent such as methanol or ethanol, optionally in the presence of an acid such as acetic acid or hydrochloric acid.

A compound of formula XVI is synthesized from a compound of formula XIV following an analogous sequence as described for the synthesis of compounds of formula Ia. The protection of the amino group present in a compound of formula III to prepare a compound of formula XIV is performed following conventional protocols described in the literature.

Alternatively, a compound of formula XVI can be prepared by reaction of a compound of formula XVIIH (prepared from a compound of formula XVIIP, wherein P represents a suitable protecting group) with a compound of formula IX, X or XI, as described above.

Compounds of formula III can be prepared from compounds of formula II following several methodologies described in the bibliography, such as the reaction with nitromethane followed by reduction (i.e. WO2013/50448A1, Preparation S), or the reaction with diethylaluminum cyanide followed by reduction (i.e. WO2006/113837 Ex 118.a.ii&iii and WO2006/81289 Ex 19.a&b).

The compounds of general formula II, IIP, IV, VI, IX, X and XI wherein R$_{1'}$, R$_2$, R$_3$, R$_{3'}$, R$_4$, R$_{4'}$, R$_5$, R$_{5'}$, R$_6$; R$_{6'}$, LG, W, X, Y, m, n, p, q and r have the meanings as defined above, are commercially available or can be prepared by conventional methods described in the bibliography.

Scheme 2

The preparation of compounds of general formula (I) wherein Y represents CO and R$_3$ and R$_{3'}$ are taken together with the connecting C-atom to form a cycloalkyl (compounds of formula Ib) can be performed as described in the following scheme:

Scheme 2

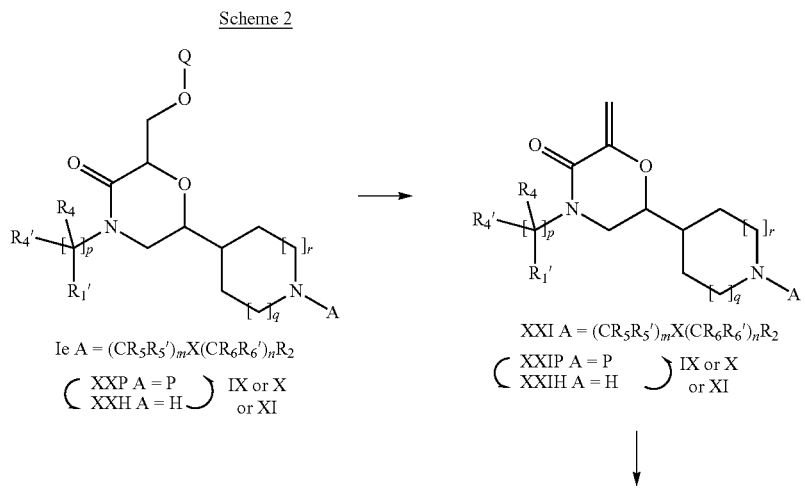

-continued

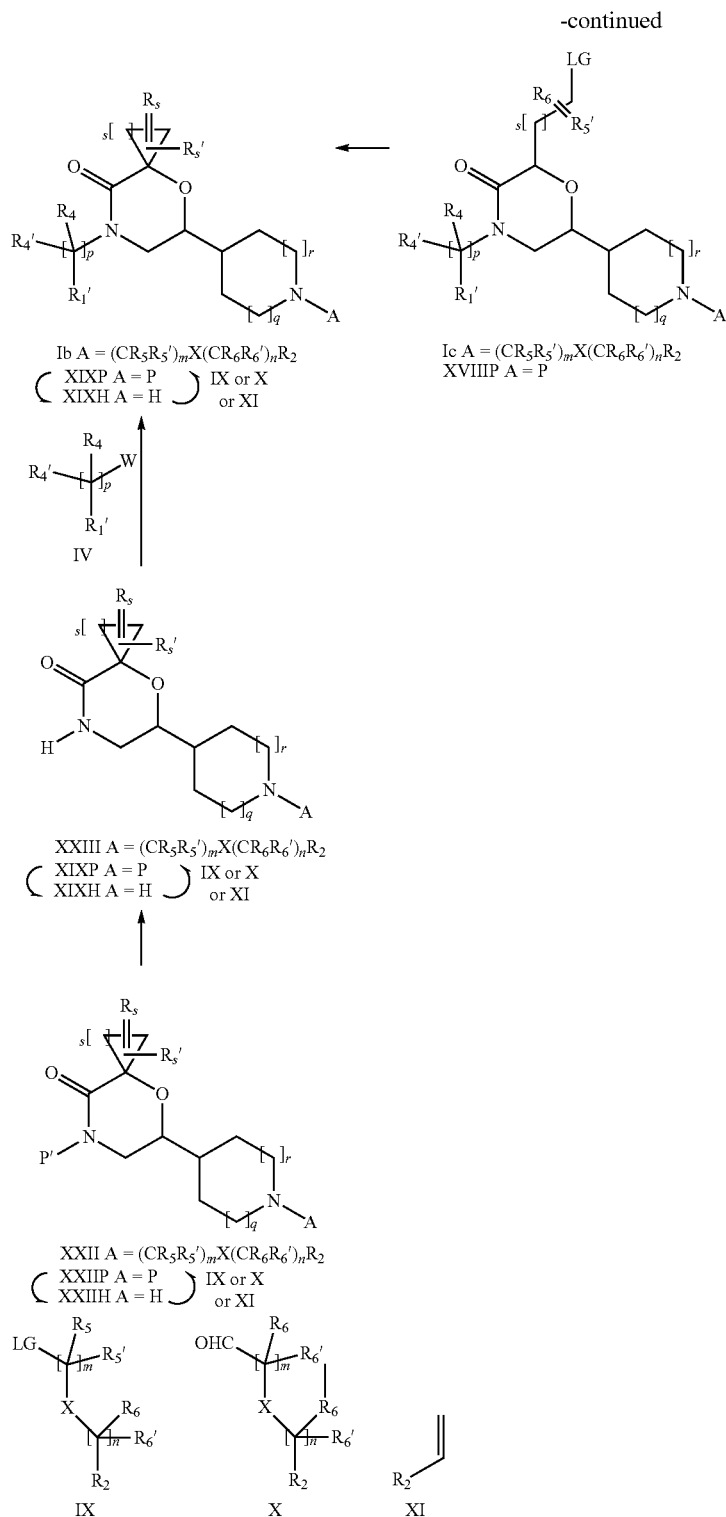
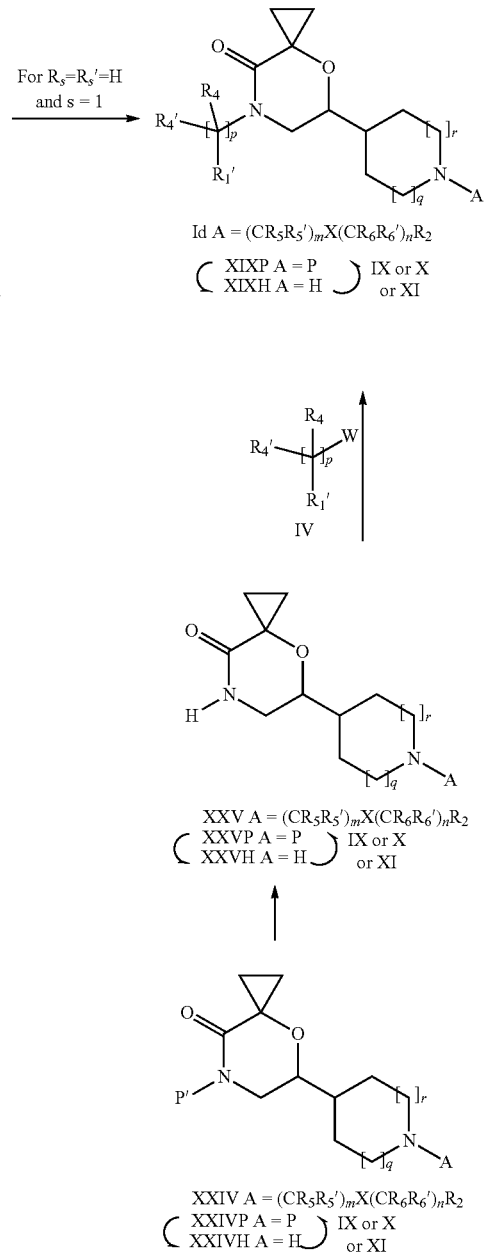

wherein $R_{1'}$, $R_2$, $R_4$, $R_{4'}$, $R_5$, $R_{5'}$, $R_6$, $R_{6'}$, X, Y, m, n, p, q and r have the meanings as defined above for a compound of formula (I), s represents 1, 2, 3 or 4, $R_s$ and $R_{s'}$ represent hydrogen or alkyl, LG represents a leaving group such as halogen, mesylate, tosylate or triflate, W represents another leaving group (such as halogen, mesylate, tosylate or triflate), P represents a suitable protecting group (preferably Boc), P' represents an orthogonal protecting group (preferably 4-methoxybenzyl), and Q represents methyl or benzyl.

A compound of formula Ib can be prepared from, a compound of formula Ic by treatment with a strong base such as lithium diisopropylamide or potassium tert-butoxide, in an aprotic solvent such as tetrahydrofuran, at a suitable temperature, preferably cooling. And analogously, a compound of formula Id (wherein $R_s=R_{s'}=H$ and s=1) can be prepared from a compound of formula Ic under the same reaction conditions.

Alternatively, compounds of formula Id can be prepared from compounds of formula XXI. The cyclopropanation reaction is carried out using a suitable methyl-transfer reagent such as trimethylsulfoxonium iodide or trimethylsulfonium iodide, in a suitable aprotic solvent such as dimethylsulfoxide, and in the presence of a strong base such as sodium hydride or potassium tert-butoxide, at a suitable temperature, preferably comprised between room temperature and 60° C. Alternatively, typical Simmons-Smith reaction conditions could be used, comprising the treatment of a compound of formula XXI with diiodomethane, a zinc source such as zinc-copper, zinc iodide or diethylzinc, in a suitable aprotic solvent, such as diethyl ether.

Compounds of formula XXI can be prepared from a compound of formula Ie wherein Q represents methyl or benzyl. The elimination reaction is carried out in the presence of a base, such as potassium tert-butoxide, in a suitable solvent, such as tetrahydrofuran.

In another alternative approach, the $—(CR_4R_{4'})_pR_{1'}$ substituent can be incorporated later in the synthesis. Thus, compounds of formula Ib and Id can be prepared from compounds of formula XXIII and XXV, respectively, following the reaction conditions described in Scheme 1 for the preparation of compounds of formula Ia from compounds of formula XIII. The compounds of formula XXIII and XXV can be prepared from suitable protected precursors XXII and XXIV, respectively, following the conditions described in Scheme 1.

In addition, the group $—(CR_5R_{5'})_mX(CR_6R_{6'})_nR_2$ can be incorporated in the last step of the synthesis to prepare compounds of formula Ib and Id from suitable protected precursors, by deprotection followed by reaction with a compound of formula IX or X or XI, as described in Scheme 1 for the preparation of compounds of formula Ia.

The compounds of general formula Ic and Ie can be prepared by the procedures described in Scheme 1 from a compound of formula V using suitable starting materials. The compounds of general formula XXII and XXIV can be prepared following the procedures described in Scheme 2 for the preparation of compounds of formula Ib and Id using the corresponding protected starting materials.

Scheme 3 and Scheme 4

Compounds of formula (I) can also be prepared starting from other compounds of formula (I), as described in Schemes 3 and 4 below.

Compounds of formula Ib, Ig and Ih can be prepared from a compound of formula If as shown in Scheme 3:

Scheme 3

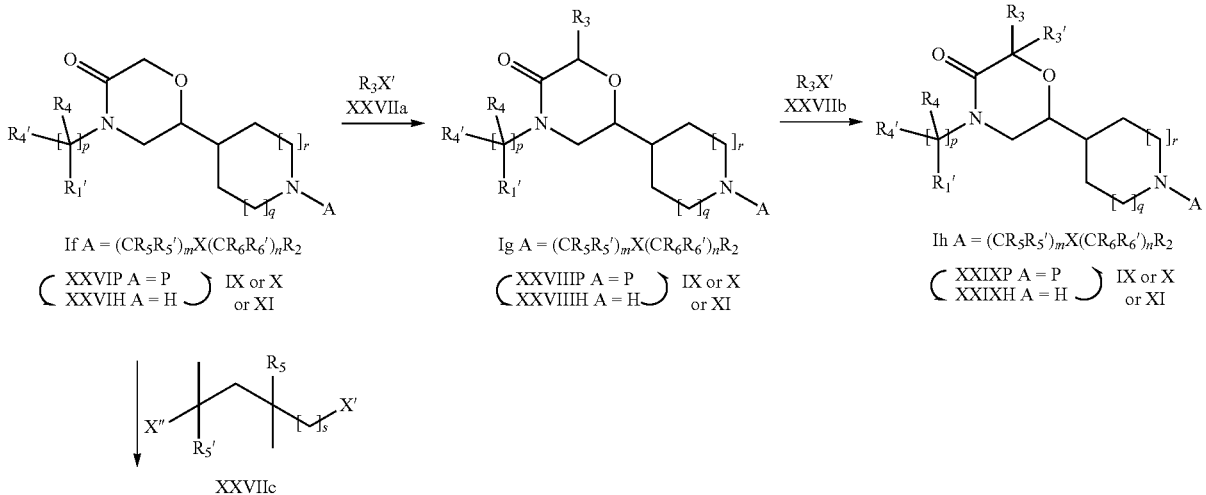

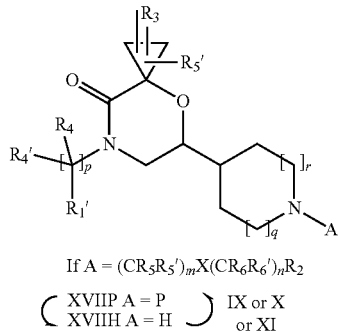

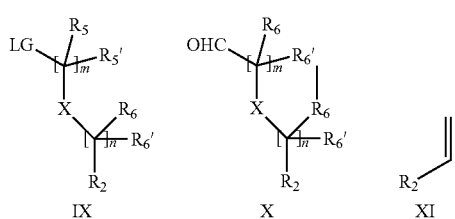

wherein $R_{1'}$, $R_2$, $R_3$, $R_{3'}$, $R_4$, $R_{4'}$, $R_5$, $R_{5'}$, $R_6$, $R_{6'}$, X, m, n, p, q and r have the meanings as defined above for a compound of formula (I), s represents 1, 2, 3 or 4, $R_s$ and $R_{s'}$ represent hydrogen or alkyl, LG, X' and X" independently represent a leaving group such as halogen, mesylate, tosylate or triflate, and P represents a suitable protecting group (preferably Boc).

A compound of formula Ig can be prepared by treating a compound of formula If with an alkylating agent of formula XXVIIa in the presence of a strong base such as lithium diisopropylamide or potassium tert-butoxide, in an aprotic solvent such as tetrahydrofuran, at a suitable temperature, preferably comprised between −78° C. and room temperature. A second alkylation can be performed under the same reaction conditions to prepare a compound of formula Ih. An analogous double-alkylation process can be used for the preparation of compounds of formula Ib, by reacting a compound of formula If with an alkylating agent of formula XXVIIc, as an alternative to the procedure-described in Scheme 2 for the preparation of compounds of formula Ib.

In addition, the group $-(CR_5R_{5'})_mX(CR_6R_{6'})_nR_2$ can be incorporated in the last step of the synthesis to prepare, compounds of formula Ib, If, Ig and Ih from suitable protected precursors, by deprotection followed by reaction with a compound of formula IX or X or XI, under the reaction conditions described in Scheme 1 for the preparation of compounds of formula Ia.

The compounds of general formula If and Ig can be prepared by the procedures described in Scheme 1 using suitable starting materials.

The compounds of general formula XXVIIa, XXVIIb and XXVIIc wherein $R_3$, $R_{3'}$, $R_s$, $R_{s'}$, X', X" and s have the meanings as defined above, are commercially available or can be prepared by conventional methods described in the bibliography.

Scheme 4 shows the preparation, of compounds of formula (I) wherein Y is $CH_2$ from compounds of formula (I) wherein Y is C(O):

Scheme 4

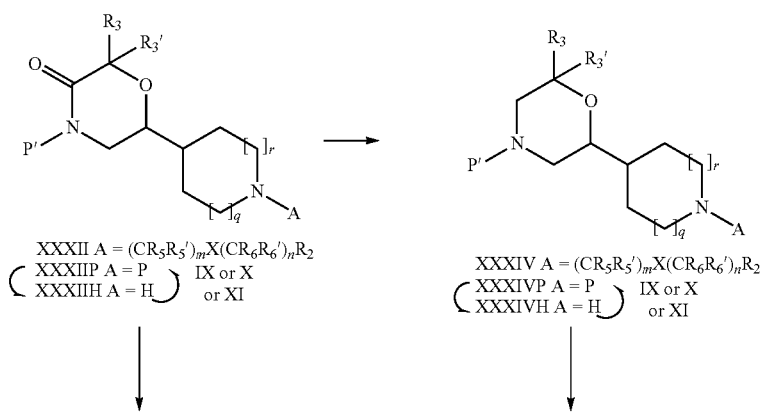

-continued

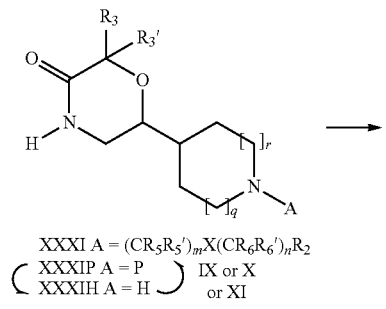

XXXI A = (CR$_5$R$_5'$)$_m$X(CR$_6$R$_6'$)$_n$R$_2$
{ XXXIP A = P } IX or X
{ XXXIH A = H } or XI

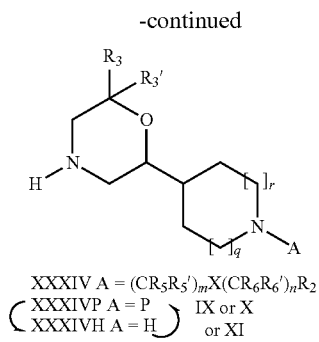

XXXIV A = (CR$_5$R$_5'$)$_m$X(CR$_6$R$_6'$)$_n$R$_2$
{ XXXIVP A = P } IX or X
{ XXXIVH A = H } or XI

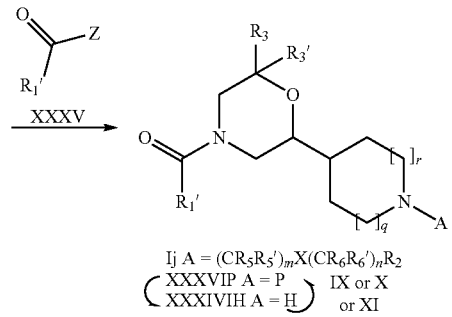

Ij A = (CR$_5$R$_5'$)$_m$X(CR$_6$R$_6'$)$_n$R$_2$
{ XXXVIP A = P } IX or X
{ XXXIVIH A = H } or XI

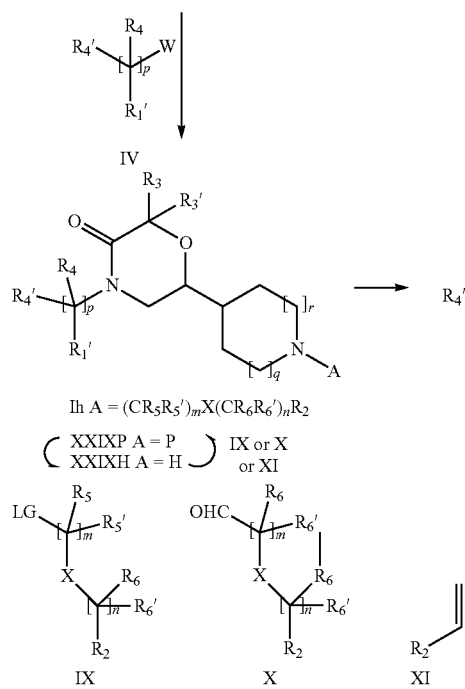

Ih A = (CR$_5$R$_5'$)$_m$X(CR$_6$R$_6'$)$_n$R$_2$
{ XXIXP A = P } IX or X
{ XXIXH A = H } or XI

II A = (CR$_5$R$_5'$)$_m$X(CR$_6$R$_6'$)$_n$R$_2$
{ XXXP A = P } IX or X
{ XXXH A = H } or XI

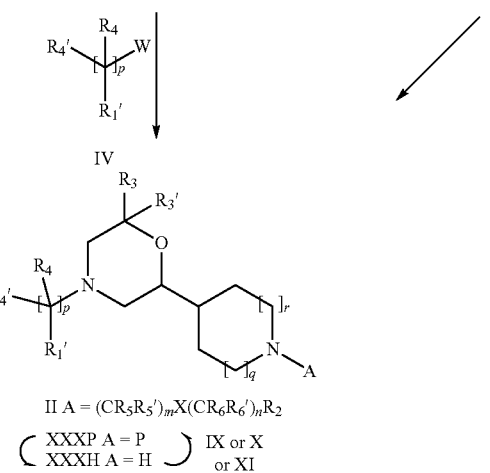

wherein R$_1'$, R$_2$, R$_3$R$_3'$, R$_4$, R$_4'$, R$_5$, R$_5'$, R$_6$, R$_6'$, X, m, n, p, q, and r have the meanings as defined above for a compound of formula (I), LG represents a leaving group such as halogen, mesylate, tosylate or triflate, W represents an aldehyde or another leaving group (such as halogen, mesylate, tosylate or triflate), P represents a suitable protecting group (preferably Boc), P' represents an orthogonal protecting group (preferably 4-methoxybenzyl or benzyl) and Z represents OH or halogen (preferably bromo or chloro).

The reduction reaction of a compound of formula Ih or Ij to yield a compound of formula Ii can be performed using a suitable reducing agent such as lithium aluminium hydride, borane-tetrahydrofuran complex or borane-dimethyl sulphide complex, in a suitable solvent such as tetrahydrofuran or diethyl ether, at a suitable temperature comprised between room temperature and the reflux temperature, preferably heating.

The reduction reaction can also be performed on a suitable precursor to (compounds of formula XXXI or XXXII) or a protected derivative (compounds of formula XXIXP, XXXIP or XXXIIP or XXXVIP wherein A=P). When P represents Boc, borane is the preferred reducing agent.

The compounds of general formula Ih can be prepared by the procedures described in Schemes 1 to 3 using suitable starting materials, or they can be prepared from a compound of formula XXXI or XXXII. The deprotection of a compound of formula XXXII to give a compound of formula XXXI and the subsequent reaction with a compound of formula IV to yield a compound of formula Ih are performed following the procedures described in Scheme 1.

The compounds of general formula XXXI and XXXII can be prepared according to the procedures described in Scheme 1 using suitable starting materials.

Accordingly, the compounds of general formula Ii may be prepared from a compound of formula-XXXIII or XXXIV following an analogous procedure.

A compound of formula Ij is prepared by reacting a compound of formula XXXIII with an acylating agent of formula XXXV. When Z is halogen, the reaction is carried out in a suitable solvent, such as dichloromethane, tetrahydrofuran, ethyl acetate or ethyl acetate-water mixtures; in the presence of an organic base such as triethylamine or diisopropylethylamine or an inorganic base such as K$_2$CO$_3$; and at a suitable temperature, preferably comprised between 0° C. and room temperature. Additionally, an activating, agent such as 4-dimethylaminopyridine can be used.

When Z is OH, the acylation reaction is carried out using a suitable coupling reagent such as N-(3-dimethylaminopropyl)-N'-ethylcarbodiimide (EDC), dicyclohexylcarbodiimide (DCC), N-[(dimethylamino)-1H-1,2,3-triazolo-[4,5-b]pyridin-1-ylmethylene]-N-methylmethanaminium hexafluorophosphate N-oxide (HATU) or N,N,N',N'-tetramethyl-O-(1H-benzotriazol-1-yl)uronium hexafluorophosphate (HBTU), optionally in the presence of 1-hydroxybenzotriazole, optionally in the presence of an organic base such as N-methylmorpholine or diisopropylethylamine, in a suitable solvent such as dichloromethane or dimethylformamide, and at a suitable temperature, preferably at room temperature.

In addition, the group —$(CR_5R_{5'})_mX(CR_6R_{6'})_nR_2$ may be incorporated at different stages of the synthesis to prepare compounds of formula Ih, Ii and Ij from suitable protected precursors, by deprotection followed by reaction with a compound of formula IX or X or XI, as described in Scheme 1 for the preparation of compounds of formula Ia.

Moreover, certain compounds of the present invention can also be obtained starting from other compounds of formula (I) by appropriate conversion reactions of functional groups, in one or several steps, using well-known reactions in organic chemistry under standard experimental conditions.

In addition, a compound of formula I that shows chirality can also be obtained by resolution of a racemic compound of formula I either by chiral preparative HPLC or by crystallization of a diastereomeric salt or co-crystal. Alternatively, the resolution step can be carried out at a previous stage, using any suitable intermediate.

EXAMPLES

Intermediates and Examples

The following abbreviations are used in the examples:
ACN: ACN
AcOH: acetic acid
Boc: tert-butoxycarbonyl
CAN: cerium ammonium nitrate
Conc: concentrated
DCM: dichloromethane
DMF: dimethylformamide
EX: example
h: hour/s
HPLC: high performance liquid chromatography
INT: intermediate
MeOH: methanol
MS: mass spectrometry
Min.: minutes
Quant: quantitative
Ret.: retention
r.t.: room temperature
Sat: saturated
s.m.: starting material
TFA: trifluoroacetic acid
THF: tetrahydrofuran
Wt: weight The following method was used to obtain the HPLC-MS data:
Column: Kinetex EVO 50×4.6 mm 2.6 um
Temperature: 40° C.
Flow: 2.0 mL/min
Gradient: $NH_4HCO_3$ pH 8: ACN (95:5)—0.5 min—(95:5)—6.5 min—(0:100)—1 min—(0:100)
Sample dissolved aprox. 1 mg/mL in $NH_4HCO_3$ pH 8/ACN Alternatively, method B was used in some cases:

Method B
Column: Kinetex EVO 50×4.6 mm 2.6 um
Temperature: 40° C.
Flow: 1.5 mL/min
Gradient: $NH_4HCO_3$ pH 8: ACN (95:5)—0.5 min—(95:5)—6.5 min—(0:100)—2 min—(0:100)
Sample dissolved aprox. 1 mg/mL in $NH_4HCO_3$ pH 8/ACN Synthesis of Intermediates Intermediate 1A: tert-Butyl 4-(1-hydroxy-2-((4-methoxybenzyl)amino)ethyl)piperidine-1-carboxylate

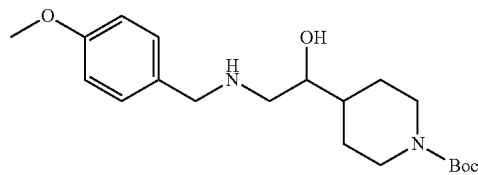 [SMILES: COc1ccc(CNCC(O)C2CCN(C(=O)OC(C)(C)C)CC2)cc1]

To a solution of tert-butyl 4-(2-amino-1-hydroxyethyl)piperidine-1-carboxylate (obtained as described in WO2013/50448A1) (3.68 g, 15.1 mmol) in dry THF (95 mL), 4-methoxybenzaldehyde (1.56 mL, 12.8 mmol), acetic acid (0.95 mL, 16.6 mmol) and sodium triacetoxyborohydride (6.38 g, 30.1 mmol) were added. The resulting mixture was stirred at r.t. overnight. An aqueous saturated solution of $NaHCO_3$ was carefully added and it was extracted with ethyl acetate. The organic phases were combined, washed with brine, dried over $MgSO_4$, filtered and concentrated to dryness to give the title compound (5.0 g, 91% yield), which was used in the following step without further purification.

Intermediate 1B: tert-Butyl 3-(1-hydroxy-2-((4-methoxybenzyl)amino)ethyl)azetidine-1-carboxylate

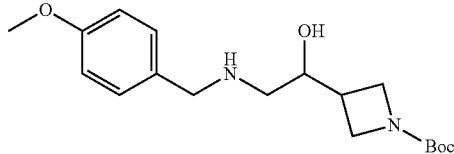 [SMILES: COc1ccc(CNCC(O)C2CN(C(=O)OC(C)(C)C)C2)cc1]

Following the procedure described for the preparation of Intermediate 1A but starting from tert-butyl 3-(2-amino-1-hydroxyethyl)azetidine-1-carboxylate, the title compound was obtained.

Intermediate 1C: tert-Butyl 4-(2-(ethylamino)-1-hydroxyethyl)piperidine-1-carboxylate

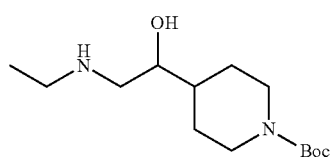 [SMILES: CCNCC(O)C1CCN(C(=O)OC(C)(C)C)CC1]

Following the procedure described for the preparation of Intermediate 1A but using acetaldehyde instead of 4-methoxybenzaldehyde, the title compound was obtained.

Intermediate 1D: tert-Butyl 4-(1-hydroxy-2-(isopropylamino)ethyl)piperidine-1-carboxylate

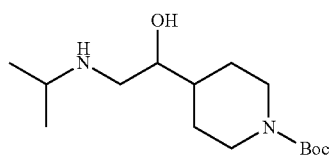 [SMILES: CC(C)NCC(O)C1CCN(C(=O)OC(C)(C)C)CC1]

Following the procedure described for the preparation of Intermediate 1A but using acetone instead of 4-methoxybenzaldehyde, the title compound was obtained.

Intermediate 2A: tert-Butyl 4-(7-(4-methoxybenzyl)-8-oxo-4-oxa-7-azaspiro[2.5]octan-5-yl)piperidine-1-carboxylate

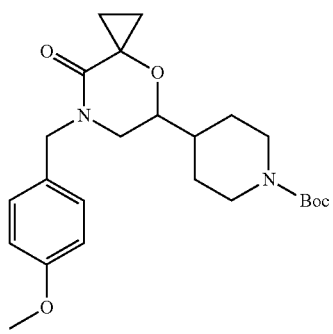 [SMILES: COc1ccc(CN2CC(C3CCN(C(=O)OC(C)(C)C)CC3)OC3(CC3)C2=O)cc1]

Step 1. tert-Butyl 4-(2-(2-bromo-4-chloro-N-(4-methoxybenzyl)butanamido)-1-hydroxyethyl)piperidine-1-carboxylate: To a solution of intermediate 1A (5.00 g, 13.7 mmol) in ethyl acetate (50 mL), a solution of $K_2CO_3$ (3.41 g, 24.7 mmol) in water (35 mL) was added. After cooling to 0-5° C., a solution of 2-bromo-4-chlorobutanoyl chloride (prepared as described in U.S. Pat. No. 6,114,541A1, 4.10 g, 18.7 mmol) in ethyl acetate (20 mL) was added dropwise. The reaction mixture was stirred at 0-5° C. for 1 h and then, it was diluted with water. The layers were separated and the aqueous phase was extracted with ethyl acetate. The organic phases were combined, washed with 0.5 M HCl aqueous solution and then $NaHCO_3$ sat solution, dried over $MgSO_4$, filtered and concentrated to dryness to give the title compound (6.58 g, crude product).

Step 2. Title compound: A solution of the crude product obtained in step 1 (6.58 g, 12.0 mmol) in dry THF (65 mL) was cooled under nitrogen to −78° C. After-addition of potassium tert-butoxide solution. (24.1 mL, 1M in THF, 24.1 mmol), the reaction mixture was stirred at −30° C. for 2 h. It was then warmed-up to 0-5° C. and additional potassium tert-butoxide solution (24.1 mL, 1M in THF, 24.1 mmol) was added. The mixture was stirred at 0-5° C. for 2 h. $NH_4Cl$ sat solution was then added, and the aqueous phase was extracted with, ethyl acetate. The organic phases were combined, dried over $MgSO_4$, filtered and concentrated under vacuum. The residue was purified by flash chromatography, silica gel, gradient DCM to MeOH/DCM (1:8) to give the title compound (2.58 g, 44% yield for the 2 steps).

This method was used for the preparation of intermediates 2B-2D using suitable starting materials:

| INT | Structure | Chemical name | s.m. |
|---|---|---|---|
| 2B | 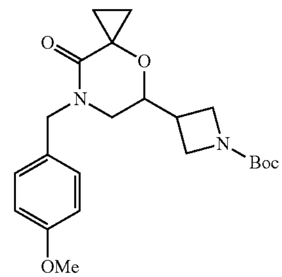 [SMILES: COc1ccc(CN2CC(C3CN(C(=O)OC(C)(C)C)C3)OC3(CC3)C2=O)cc1] | tert-butyl 3-(7-(4-methoxybenzyl)-8-azaspiro[2.5]octan-5-yl)azetidine-1-carbaylate | 1B |
| 2C | 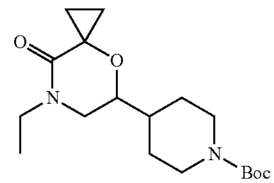 [SMILES: CCN1CC(C2CCN(C(=O)OC(C)(C)C)CC2)OC2(CC2)C1=O] | tert-butyl 4-(7-ethyl-8-oxo-4-oxa-7-azaspiro[2.5]octan-5-yl)piperidine-1-carboxylate | 1C |
| 2D | 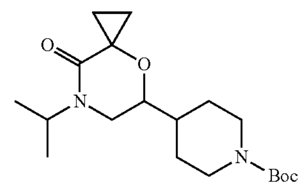 [SMILES: CC(C)N1CC(C2CCN(C(=O)OC(C)(C)C)CC2)OC2(CC2)C1=O] | tert-butyl 4-(7-isopropyl-8-oxo-4-oxa-7-azaspiro[2.5]octan-5-yl)piperidine-1-carboxylate | 1D |

Intermediate 2E: tert-Butyl 4-(4-(4-methoxybenzyl)-5-oxomorpholin-2-yl)piperidine-1-carboxylate

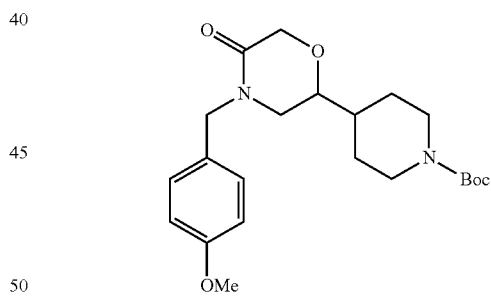

Step 1. tert-Butyl 4-(2-(2-chloro-N-(4-methoxybenzyl)acetamido)-1-hydroxyethyl)piperidine-1-carboxylate: To a solution of intermediate 1A (1.42 g, 3.89 mmol) in ethyl acetate (14 mL), a solution of $K_2CO_3$ (1.5 g, 10:9 mmol) in water (11 mL) was added. After cooling to 0° C., a solution 2-chloroacetyl chloride (0.42 mL, 5.28 mmol) in ethyl acetate (2 mL) was added dropwise. The reaction mixture was stirred at 0-5° C. for 1 h and then it was diluted with water. The layers were separated and the aqueous phase was extracted with ethyl acetate. The organic phases were combined, washed with cold 0.5 M HCl aqueous solution and then $NaHCO_3$ sat solution, dried over $MgSO_4$, filtered and concentrated to dryness to give the title compound (1.14 g, 67% yield).

Step 2). Title compound: A solution of the crude product obtained in Step 1 (1.14 g, 2.6 mmol) in THF (11 mL) was cooled to −78° C. using a dry ice/acetone bath. After addition of potassium tert-butoxide solution (3.9 mL, 1M in THF, 3.9 mmol), the reaction mixture was stirred at −78° C. for 1 h. NH₄Cl sat solution was then added, and the aqueous phase was extracted with ethyl acetate (×3). The organic phases were combined, dried over MgSO₄, filtered and concentrated under vacuum to give the title compound (981 mg, 94% yield).

This method was used for the preparation of intermediates 2F-2G using suitable starting materials:

| INT | Structure | Chemical name | s.m. |
|---|---|---|---|
| 2F | 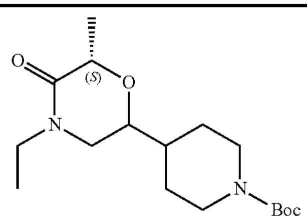 | tert-butyl 4-((6S)-4-ethyl-6-methyl-5-oxomorpholin-2-yl)piperidine-1-carboxylate | 1C |
| 2G | 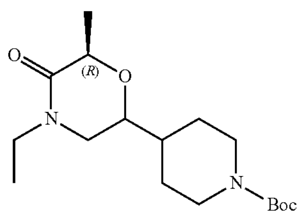 | tert-butyl 4-((6R)-4-ethyl-6-methyl-5-oxomorpholin-2-yl)piperidine-1-carboxylate | 1C |

Intermediate 3A: 5-(1-Benzylpiperidin-4-yl)-4-oxa-7-azaspiro[2.5]octan-8-one

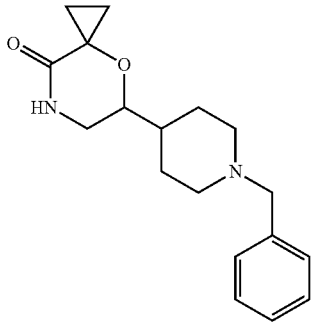 [SMILES: O=C1NCC(C2CCN(Cc3ccccc3)CC2)OC12CC2]

Step 1. 5-(Piperidin-4-yl)-4-oxa-7-azaspiro[2.5]octan-8-one trifluoroacetate. Intermediate 2A (1.50 g, 3.48 mmol) was dissolved in TFA (26.7 mL, 348 mmol) and the mixture stirred at 80° C. in a sealed tube for 5 days. The reaction was concentrated to dryness to give the title compound as a crude product (1.13 g, quant yield), that was used in the following step without further purification.

Step 2. Title compound: To a mixture of the crude product obtained in step 1 (0.565 g, 1.74 mmol) in dichloroethane (12 mL) and methanol (1 mL), benzaldehyde (0.266 mL, 2.61 mmol) was added. The reaction mixture was stirred at r.t. for 15 min. and then sodium triacetoxyborohydride (0.277 g, 2.61 mmol) was added in portions. The resulting mixture was stirred at r.t. overnight. Water and conc NH₃, were carefully added and, it was extracted with ethyl acetate. The organic phases were combined, washed with brine, dried over Na₂SO₄, filtered and concentrated to dryness. The residue was purified by flash chromatography, silica gel, gradient DCM to MeOH/DCM (1:4) to give the title compound (114 mg, 22% yield for the two steps).

Intermediate 3B: 5-(1-Phenethylpiperidin-4-yl)-4-oxa-7-azaspiro[2.5]octan-8-one

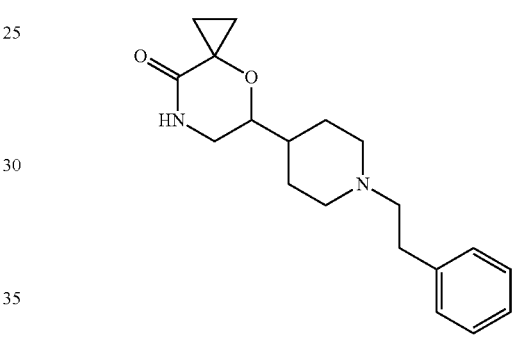

A mixture of the crude product obtained in step 1 of intermediate 3A (0.565 g, 1.74 mmol), (2-bromoethyl)benzene (0.38 mL, 2.79 mmol) and K₂CO₃ (1.20 g, 8.71 mmol) in ACN (7 mL) was heated at 80° C. in a sealed tube overnight. 1M NaOH aqueous solution was added, and the reaction mixture was extracted with ethyl acetate. The organic phases were combined, washed with brine, dried over MgSO₄, filtered and concentrated to dryness. The residue was purified by flash chromatography, silica gel, gradient DCM to MeOH/DCM (1:4) to give the title compound (370 mg, 68% yield for the two steps).

Intermediates 3C and 3D were prepared according to the procedure described for the preparation of Intermediate 3A, using suitable starting materials:

| INT | Structure | Chemical name | s.m. |
|---|---|---|---|
| 3C | 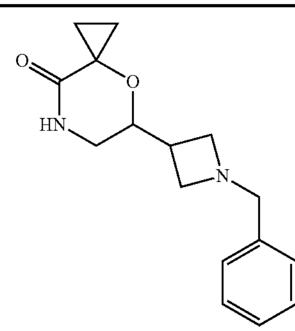 | 5-(1-benzylazetidin-3-yl)-4-oxa-7-azaspiro[2.5]octan-8-one | 2B |

141
-continued

| INT | Structure | Chemical name | s.m. |
|---|---|---|---|
| 3D | 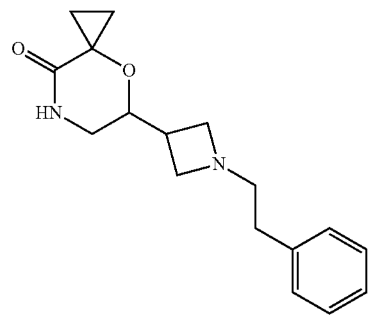 [SMILES: O=C1NCC(C2CN(CCc3ccccc3)C2)OC12CC2] | 5-(1-phenethylazetidin-3-yl)-4-oxa-7-azaspiro[2.5]octan-8-one | 2B |

Intermediate 3E: 5-(1-Isopentylpiperidin-4-yl)-4-oxa-7-azaspiro[2.5]octan-8-one

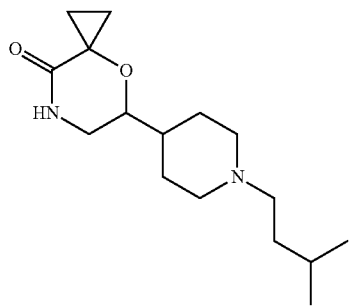 [SMILES: CC(C)CCN1CCC(C2CNC(=O)C3(CC3)O2)CC1]

A mixture of Example 16 (1.20 g, 3.0 mmol), CAN (4.93 g, 9.0 mmol), ACN (15 mL) and water (15 mL) was stirred at r.t. overnight. NaHCO₃ sat solution was added to the reaction mixture, that was filtered over a pad of celite and then it was extracted with ethyl acetate. The organic phases were combined, washed with brine, dried over MgSO₄, filtered and concentrated to dryness. The residue was purified by flash chromatography, silica gel, gradient DCM to MeOH/DCM (1:4) to give the title compound (184 mg, 22% yield).

Intermediate 3F: 6-(1-Benzylpiperidin-4-yl)morpholin-3-one

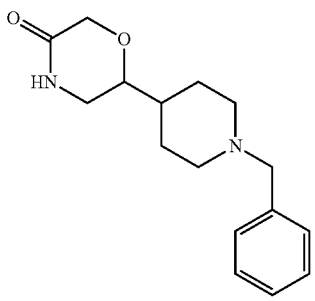 [SMILES: O=C1COC(C2CCN(Cc3ccccc3)CC2)CN1]

Following the procedure described for the preparation of Intermediate 3E but starting from Example 21, the title compound was obtained.

Intermediate 4: tert-Butyl 4-(7-(4-methoxybenzyl)-4-oxa-7-azaspiro[2.5]octan-5-yl)piperidine-1-carboxylate

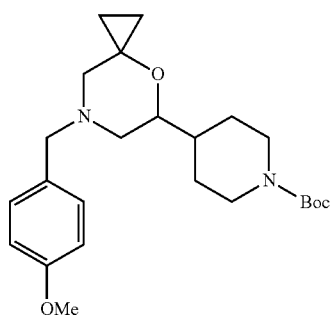 [SMILES: COc1ccc(CN2CC(C3CCN(C(=O)OC(C)(C)C)CC3)OC3(CC3)C2)cc1]

To a solution of intermediate 2A (0.75 g, 1.74 mmol) in THF (4.5 mL), borane-tetrahydrofuran complex solution (5.2 mL, 1M in THF, 5.2 mmol) was added dropwise at r.t. The reaction mixture was stirred at 65° C. for 3 h, then it was cooled to r.t. Additional borane-tetrahydrofuran complex solution (5.2 mL, 1M in THF, 5.2 mmol) was added and the mixture was stirred at 65° C. for 3 h to get the reaction to completion. The mixture was cooled with an ice-water bath and 1M NaOH aqueous sol was carefully added, and then the resulting mixture was heated to 70° C. for 6 h. After cooling to r.t., it was diluted with ethyl acetate. The phases were separated and the aqueous phase was back extracted with ethyl acetate. The organic phases were combined, dried over MgSO₄, filtered and concentrated to dryness to give the title compound as a crude product that was used as such without further purification (682 mg, 94% yield).

Intermediate 5: tert-Butyl 4-(4-oxa-7-azaspiro[2.5]octan-5-yl)piperidine-1-carboxylate acetate

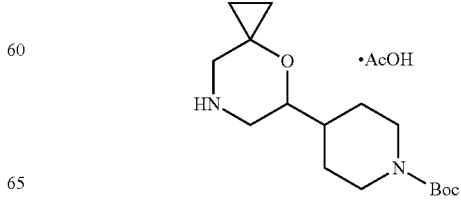

A mixture of intermediate 4 (0.682 g, 1.64 mmol), AcOH (0.093 mL, 1.64 mmol) and palladium (68 mg, 10% wt on carbon) in methanol (2 mL) was stirred under 3 bars of $H_2$ at 50° C. for 1 day. The catalyst was filtered off and the solvent was removed under vacuum to give the title compound as a crude product that was used as such without further purification (583 mg, quant yield)

Intermediate 6: tert-Butyl 4-(7-benzoyl-4-oxa-7-azaspiro[2.5]octan-5-yl)piperidine-1-carboxylate

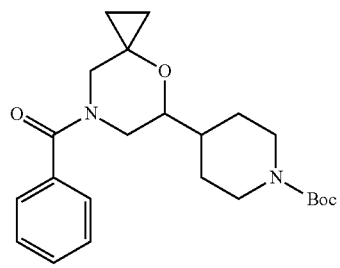 [SMILES: CC(C)(C)OC(=O)N1CCC(C2CN(C(=O)c3ccccc3)CC3(CC3)O2)CC1]

To a solution of intermediate 5 (583 mg, 1.64 mmol) in DCM (6 mL) at 0° C., triethylamine (0.34 mL, 2.45 mmol) and benzoyl chloride (0.23 mL, 1.96 mmol) were added. The reaction mixture was stirred at r.t. for 2 h, then sat aqueous $NaHCO_3$ solution was added. The phases were separated and the aqueous phase was back extracted with DCM. The organic phases were combined, washed with 1M NaOH aqueous solution, dried over $MgSO_4$, filtered and concentrated to dryness. The residue was purified by flash chromatography, silica gel, gradient DCM to MeOH/DCM (1:4) to give the title compound (365 mg, 56% yield).

Intermediate 7: tert-Butyl 3-(7-ethyl-8-oxo-4-oxa-7-azaspiro[2.5]octan-5-yl)azetidine-1-carboxylate

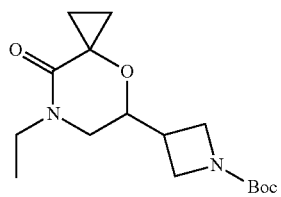 [SMILES: CCN1CC(C2CN(C(=O)OC(C)(C)C)C2)OC2(CC2)C1=O]

Step 1. 5-(Azetidin-3-yl)-4-oxa-7-azaspiro[2.5]octan-8-one trifluoroacetate. Intermediate 2B (1.50 g, 3.73 mmol) was dissolved in TFA (28.5 mL, 372 mmol) and the mixture was stirred at 80° C. in a sealed tube overnight. It was concentrated to dryness and the residue was diluted with water. The aqueous phase was washed twice with ethyl acetate, that was discarded, and it was evaporated to dryness to give the title compound as a crude product (1.33 g, overweight, quant yield assumed).

Step 2. tert-Butyl 3-(8-oxo-4-oxa-7-azaspiro[2.5]octan-5-yl)azetidine-1-carboxylate. A solution of di-tert-butyl dicarbonate (313 mg, 1.43 mmol) in 1,4-dioxane (0.57 mL) was added to a solution of the product obtained in Step 1 (283 mg, 0.95 mmol) in 1M NaOH solution (2.87 mL, 2.87 mmol), and the mixture was stirred at r.t. overnight. Then, it was extracted with ethyl acetate (×3). The organic phases were combined, washed with brine, dried over $Na_2SO_4$, filtered and concentrated to dryness. The residue was purified by flash chromatography, silica gel, gradient DCM to MeOH/DCM (1:9) to give the title compound (190 mg, 70% yield).

Step 3. Title compound: To a solution of the product obtained in Step 2 (190 mg, 0.67 mmol) in dry DMF (6.7 mL), NaH (54 mg, 60 wt % in mineral oil, 1.35 mmol) was added at 0° C. under a nitrogen atmosphere. The reaction mixture was stirred at 0° C. for 30 min, then 1-iodoethane (0.06 mL, 0.74 mmol) was added and the resulting mixture was stirred at r.t. for 2 h. Aqueous sat. $NaHCO_3$ solution was added to the reaction mixture and it was extracted with ethyl acetate (×3). The organic phases were combined, washed with brine, dried over $Na_2SO_4$, filtered and concentrated to dryness. The residue was purified by flash chromatography, silica gel, gradient DCM to MeOH/DCM (1:9) to give the title compound (210 mg, quant yield).

SYNTHESIS OF EXAMPLES

Example 1: 7-(4-Methoxybenzyl)-5-(1-phenethylpiperidin-4-yl)4-oxa-7-azaspiro[2.5]octan-8-one

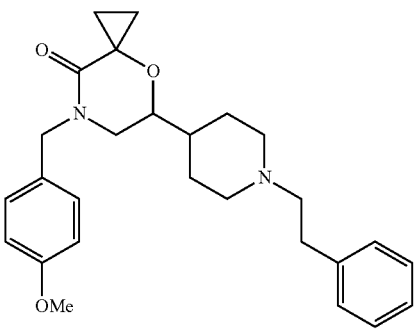 [SMILES: COc1ccc(CN2CC(C3CCN(CCc4ccccc4)CC3)OC3(CC3)C2=O)cc1]

Step 1. 7-(4-Methoxybenzyl)-5-(piperidin-4-yl)-4-oxa-7-azaspiro[2.5]octan-8-one trifluoroacetate. To a solution of intermediate 2A (500 mg, 1.16 mmol) in DCM (5 mL), TFA (0.89 mL, 11.6 mmol) was added, and the reaction mixture was stirred at r.t. for 3 h. The solvent was evaporated to dryness to give the title compound as a crude product (1.06 g, 49 wt %, quant yield), that was used in the following step without further purification.

Step 2. Title compound: A mixture of the crude product obtained in step 1 (0.526 g, 49 wt %, 0.580 mmol), (2-bromoethyl)benzene (0.127 mL, 0.929 mmol) and $K_2CO_3$ (0.401 g, 2.90 mmol) in ACN (6 mL) was heated at 80° C. in a sealed tube overnight. 1M NaOH aqueous solution was added, and the reaction mixture was extracted with ethyl acetate. The organic phases were combined, washed with brine, dried over $MgSO_4$, filtered and concentrated to dryness. The residue was purified by flash chromatography, silica gel, gradient DCM to MeOH/DCM (1:4) to give the title compound (171 mg, 68% yield for the two steps).

HPLC retention time: 4.93 min; MS: 435.2 (M+H).

This method was used for the preparation of example 2 using suitable starting materials:

| EX | Structure | Chemical name | Ret time (min) | MS (M + H) |
|---|---|---|---|---|
| 2 | 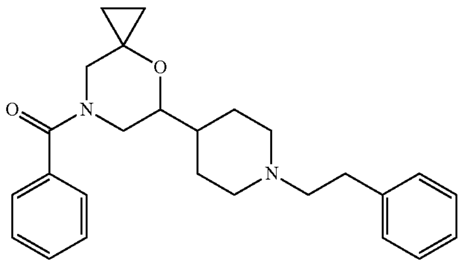 [SMILES: O=C(c1ccccc1)N1CC(C2CCN(CCc3ccccc3)CC2)OC2(CC2)C1] | (5-(1-phenethylpiperidin-4-yl)-4-oxa-7-azaspiro[2.5]octan-7-yl)(phenyl)methanone | 4.75 | 405.2 |

Example 3: 5-(1-Benzylpiperidin-4-yl)-7-(4-methoxybenzyl)-4-oxa-7-azaspiro[2.5]octan-8-one

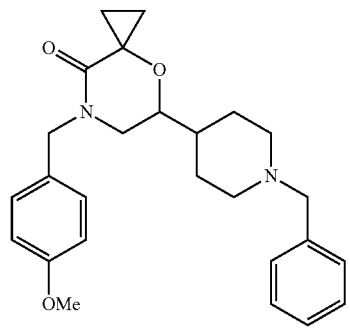 [SMILES: COc1ccc(CN2CC(C3CCN(Cc4ccccc4)CC3)OC3(CC3)C2=O)cc1]

To a solution of the crude product obtained in step 1 of example 1 (0.526 g, 49 wt %, 0.580 mmol) in dry THF (4 mL), benzaldehyde (0.088 mL, 0.870 mmol) was added. The reaction mixture was stirred at r.t. for 15 min. and then sodium triacetoxyborohydride (0.578 g, 2.73 mmol) was added in portions. The resulting mixture was stirred at r.t. overnight. Water and $NH_3$ conc were carefully added and it was extracted with ethyl acetate. The organic phases were combined, washed with brine, dried over $MgSO_4$, filtered and concentrated to dryness. The residue was purified by flash chromatography, silica gel, gradient DCM to MeOH/DCM (1:4), then repurified by flash chromatography, $C_{18}$, gradient aqueous $NH_4HCO_3$ (pH 8) to ACN to give the title compound (58 mg, 23% yield for the two steps).

HPLC retention time: 5.01 min; MS: 421.3 (M+H).

This method was used for the preparation of examples 4-6 using suitable starting materials:

| EX | Structure | Chemical name | Ret time (min) | MS (M + H) |
|---|---|---|---|---|
| 4 | 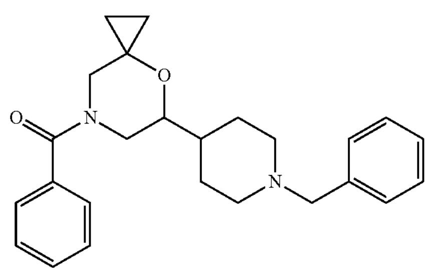 [SMILES: O=C(c1ccccc1)N1CC(C2CCN(Cc3ccccc3)CC2)OC2(CC2)C1] | (5-(1-benzylpiperidin-4-yl)-4-oxa-7-azaspiro[2.5]octan-7-yl)(phenyl)methanone | 4.72 | 391.2 |
| 5 | 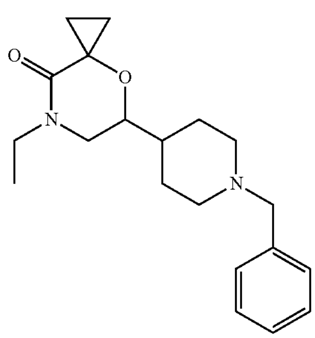 [SMILES: CCN1CC(C2CCN(Cc3ccccc3)CC2)OC2(CC2)C1=O] | 5-(1-benzylpiperidin-4-yl)-7-ethyl-4-oxa-7-azaspiro[2.5]octan-8-one | 4.16 | 329.2 |

| EX | Structure | Chemical name | Ret time (min) | MS (M + H) |
|---|---|---|---|---|
| 6 | 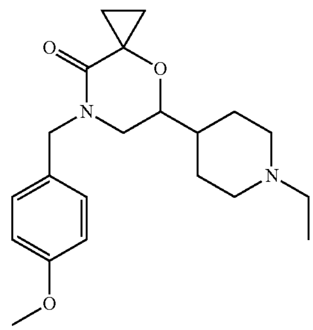 [SMILES: CCN1CCC(C2CN(Cc3ccc(OC)cc3)C(=O)C3(CC3)O2)CC1] | 5-(1-ethylpiperidin-4-yl)-7-(4-methoxybenzyl)-4-oxa-7-azaspiro[2.5]octan-8-one | 3.38 | 359.2 |

Example 7: 7-Ethyl-5-(1-phenethylpiperidin-4-yl)-4-oxa-7-azaspiro[2.5]octan-8-one

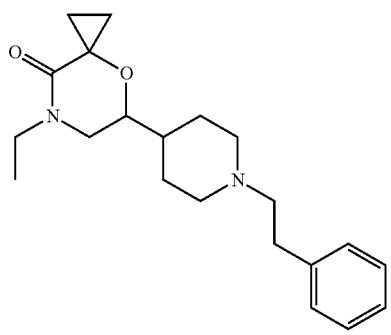

To a solution of intermediate 3B (0.200 g, 0.636 mmol) in dry DMF (6.4 mL), NaH (51 mg, 60 wt % in mineral oil, 1.27 mmol) was added at 0° C. The reaction mixture was stirred at 0° C. for 30 min, then 1-iodoethane (0.077 mL, 0.954 mmol) was added and the resulting mixture was stirred at r.t. for 3 h. An aqueous sat. NaHCO$_3$ solution was added to the reaction mixture and it was extracted with ethyl acetate. The organic phases were combined, washed with brine, dried over MgSO$_4$, filtered and concentrated to dryness. The residue was purified by flash chromatography, silica gel, gradient DCM to MeOH/DCM (1:4) to give the title compound (175 mg, 80% yield).

HPLC retention time: 4.11 min; MS: 343.2 (M+H).

This method was used for the preparation of example 8 using suitable starting materials:

| EX | Structure | Chemical name | Ret time (min) | MS (M + H) |
|---|---|---|---|---|
| 8 | 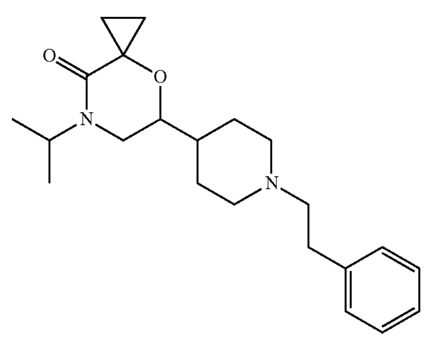 [SMILES: CC(C)N1CC(C2CCN(CCc3ccccc3)CC2)OC2(CC2)C1=O] | 7-isopropyl-5-(1-phenethylpiperidin-4-yl)-4-oxa-7-azaspiro[2.5]octan-8-one | 4.39 | 357.2 |

Example 9: 5-(1-Phenethylpiperidin-4-yl)-7-phenyl-4-oxa-7-azaspiro[2.5]octan-8-one

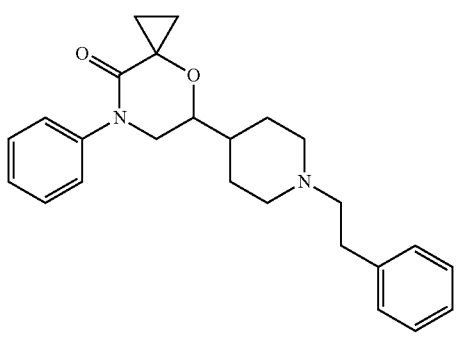 [SMILES: O=C1N(c2ccccc2)CC(C2CCN(CCc3ccccc3)CC2)OC12CC2]

A mixture of intermediate 3B (0.100 g, 0.318 mmol), cesium carbonate (0.135 g, 0.700 mmol), tris(dibenzylideneacetone)dipalladium(0) (14 mg, 0.016 mmol), 4,5-bis(diphenylphosphino)-9,9-dimethylxanthene (16 mg, 0.027 mmol) and bromobenzene (0.040 mL, 0.382 mmol) in dry 1,4-dioxane (2.5 mL) was heated under an argon atmosphere in a sealed tube at 110° C. overnight. The reaction mixture was cooled, the solids were filtered off and it was concentrated to dryness. Additional cesium carbonate (0.135 g, 0.700 mmol), tris(dibenzylideneacetone)dipalladium(0) (14 mg, 0.016 mmol), 4,5-bis(diphenylphosphino)-9,9-dimethylxanthene (16 mg, 0.027 mmol), bromobenzene (0.040 g, 0.382 mmol) and dry 1,4-dioxane (2.5 mL) were added. After stirring for an additional day at 110° C. under an argon atmosphere, the solids were filtered off and the solvent evaporated to dryness. The residue was purified by flash chromatography, silica gel, gradient DCM to MeOH/DCM (1:4) to give the title compound (87 mg, 70% yield).

HPLC retention time: 4.72 min; MS: 391.2 (M+H).

This method was used for the preparation of example 10 using suitable starting materials:

| EX | Structure | Chemical name | Ret time (min) | MS (M + H) |
|---|---|---|---|---|
| 10 | 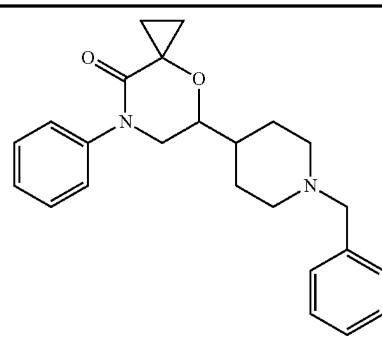 | 5-(1-benzylpiperidin-4-yl)-7-phenyl-4-oxa-7-azaspiro[2.5]octan-8-one | 4.81 | 377.2 |

Example 11: 7-Ethyl-5-(1-phenethylpiperidin-4-yl)-4-oxa-7-azaspiro[2.5]octane

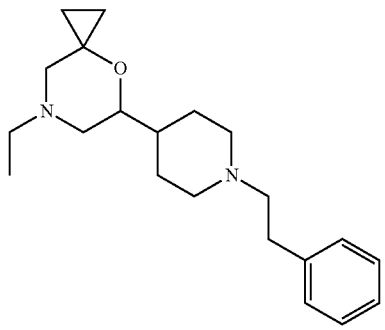 [SMILES: CCN1CC(C2CCN(CCc3ccccc3)CC2)OC2(CC2)C1]

To a solution of example 7 (120 mg, 0.350 mmol) in THF (0.5 mL), cooled at 0° C., lithium aluminium hydride solution (1.05 mL, 1M in THF, 1.05 mmol) was added dropwise. The reaction mixture was stirred at 50° C. overnight, then NaHCO$_3$ sat aqueous solution was added, and the aqueous phase was extracted with ethyl acetate. The organic phases were combined, washed with water, dried over MgSO$_4$, filtered and concentrated to dryness. The residue was purified by flash chromatography, silica gel, gradient DCM to MeOH/DCM (1:4) to give the title compound (83 mg, 72% yield).

HPLC retention time: 4.06 min; MS: 329.2 (M+H)

This method was used for the preparation of examples 12-14 using suitable starting materials:

| EX | Structure | Chemical name | Ret time (min) | MS (M + H) |
|---|---|---|---|---|
| 12 | 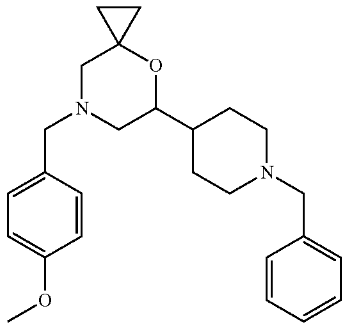 [SMILES: COc1ccc(CN2CC(C3CCN(Cc4ccccc4)CC3)OC3(CC3)C2)cc1] | 5-(1-benzylpiperidin-4-yl)-7-(4-methoxybenzyl)-4-oxa-7-azaspiro[2.5]octane | 5.34 | 407.2 |
| 13 | 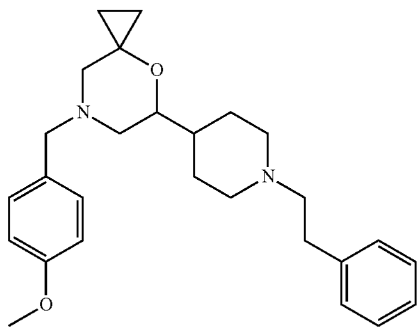 [SMILES: COc1ccc(CN2CC(C3CCN(CCc4ccccc4)CC3)OC3(CC3)C2)cc1] | 7-(4-methoxybenzyl)-5-(1-phenethylpiperidin-4-yl)-4-oxa-7-azaspiro[2.5]octane | 5.22 | 421.2 |
| 14 | 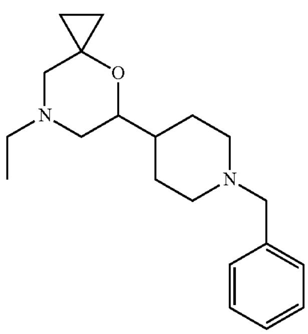 [SMILES: CCN1CC(C2CCN(Cc3ccccc3)CC2)OC2(CC2)C1] | 5-(1-benzylpiperidin-4-yl)-7-ethyl-4-oxa-7-asazaspiro[2.5]octane | 4.11 | 315.2 |

Examples 15 and 16 were prepared according to the procedure described in Example 1, using suitable starting materials:

| EX | Structure | Chemical name | Ret time (min) | MS (M + H) |
|---|---|---|---|---|
| 15 | 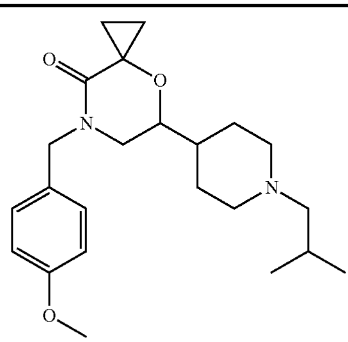 | 5-(1-isobutylpiperidin-4-yl)-7-(4-methoxybenzyl)-4-oxa-7-azaspiro[2.5]octan-8-one | 4.59 | 387.2 |

| EX | Structure | Chemical name | Ret time (min) | MS (M + H) |
|---|---|---|---|---|
| 16 | 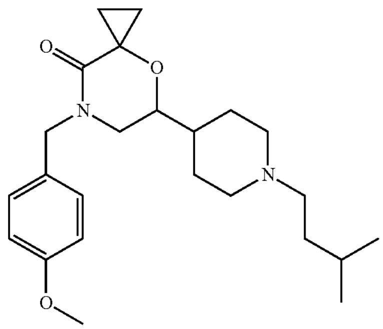 [SMILES: COc1ccc(CN2CC(C3CCN(CCC(C)C)CC3)OC3(CC3)C2=O)cc1] | 5-(1-isopentylpiperidin-4-yl)-7-(4-methoxybenzyl)-4-oxa-7-azaspiro[2.5]octan-8-one | 4.56 | 401.3 |

Examples 17 to 20 are prepared according to the procedure described in Example 1, using suitable starting materials:

| 17 | | (2S,6R)-4-ethyl-6-(1-isopentylpiperidin-4-yl)-2-methylmorpholin-3-one |
|---|---|---|
| 18 | | (2S,6S)-4-ethyl-6-(1-isopentylpiperidin-4-yl)-2-methylmorpholin-3-one |
| 19 | | (2R,6R)-4-ethyl-6-(1-isopentylpiperidin-4-yl)-2-methylmorpholin-3-one |
| 20 | | (2R,6S)-4-ethyl-6-(1-isopentylpiperidin-4-yl)-2-methylmorpholin-3-one |

Examples 21 to 39 were prepared according to the procedure described in Example 3, using suitable starting materials:

| EX | Structure | Chemical name | Ret time (min) | MS (M + H) |
|---|---|---|---|---|
| 21 | 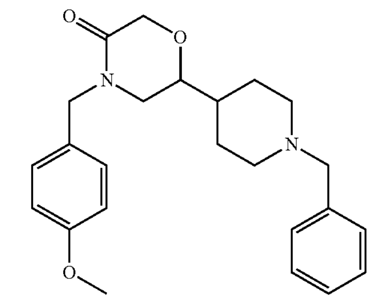 [SMILES: COc1ccc(CN2CC(C3CCN(Cc4ccccc4)CC3)OCC2=O)cc1] | 6-(1-benzylpiperidin-4-yl)-4-(4-methoxybenzyl)morpholin-3-one | 4.37 | 395.2 |
| 22 | 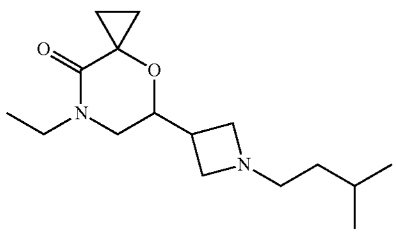 [SMILES: CCN1CC(C2CN(CCC(C)C)C2)OC2(CC2)C1=O] | 7-ethyl-5-(1-isopentylazetidin-3-yl)-4-oxa-7-azaspiro[2.5]octan-8-one | 3.16 | 281.2 |
| 23 | 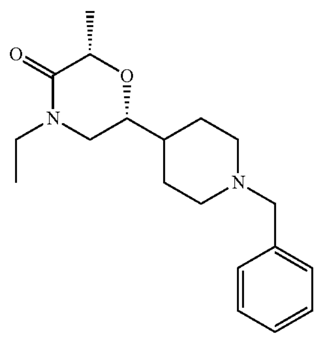 [SMILES: CCN1C[C@@H](C2CCN(Cc3ccccc3)CC2)O[C@@H](C)C1=O] | (2S,6R)-6-(1-benzylpiperidin-4-yl)-4-ethyl-2-methylmorpholin-3-one | 4.1 (meth B) | 317.1 |
| 24 | 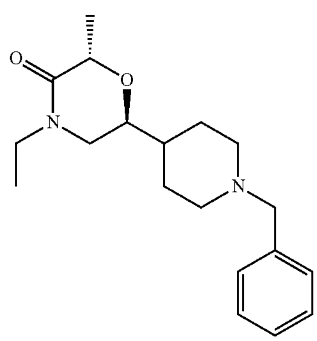 [SMILES: CCN1C[C@H](C2CCN(Cc3ccccc3)CC2)O[C@@H](C)C1=O] | (2S,6S)-6-(1-benzylpiperidin-4-yl)-4-ethyl-2-methylmorpholin-3-one | 4.27 (meth B) | 317.2 |
| 25 | 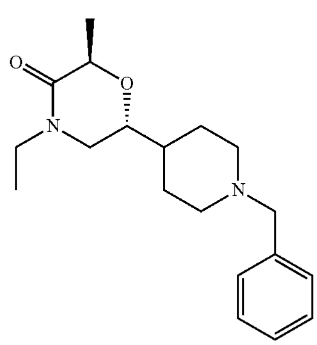 [SMILES: CCN1C[C@@H](C2CCN(Cc3ccccc3)CC2)O[C@H](C)C1=O] | (2R,6R)-6-(1-benzylpiperidin-4-yl)-4-ethyl-2-methylmorpholin-3-one | 4.34 (meth B) | 317.2 |

-continued

| EX | Structure | Chemical name | Ret time (min) | MS (M + H) |
|---|---|---|---|---|
| 26 | 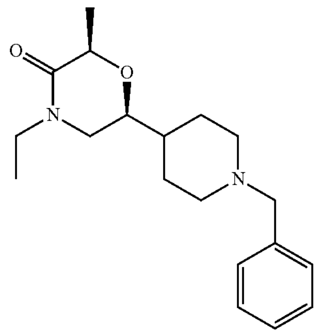 [SMILES: CCN1C[C@H](C2CCN(Cc3ccccc3)CC2)O[C@H](C)C1=O] | (2R,6S)-6-(1-benzylpiperidin-4-yl)-4-ethyl-2-methylmorpholin-3-one | 4.17 (meth B) | 317.1 |
| 27 | 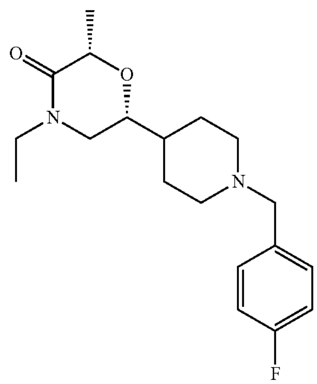 [SMILES: CCN1C[C@@H](C2CCN(Cc3ccc(F)cc3)CC2)O[C@@H](C)C1=O] | (2S,6R)-4-ethyl-6-(1-(4-fluorobenzyl)piperidin-4-yl)-2-methylmorpholin-3-one | 4.38 (meth B) | 335.2 |
| 28 | 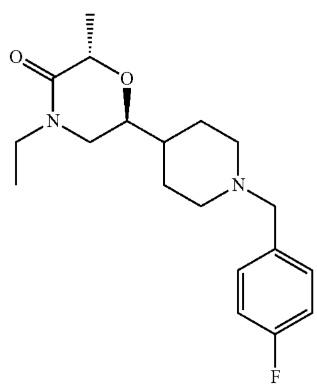 [SMILES: CCN1C[C@H](C2CCN(Cc3ccc(F)cc3)CC2)O[C@@H](C)C1=O] | (2S,6S)-4-ethyl-6-(1-(4-fluorobenzyl)piperidin-4-yl)-2-methylmorpholin-3-one | 4.50 (meth B) | 335.1 |
| 29 | 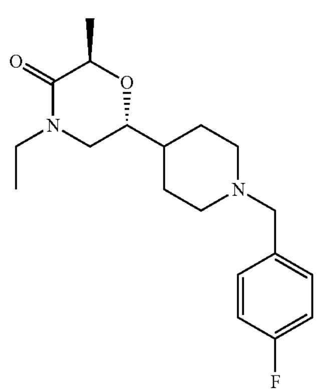 [SMILES: CCN1C[C@@H](C2CCN(Cc3ccc(F)cc3)CC2)O[C@H](C)C1=O] | (2R,6R)-4-ethyl-6-(1-(4-fluorobenzyl)piperidin-4-yl)-2-methylmorpholin-3-one | 4.47 (meth B) | 335.1 |

-continued

| EX | Structure | Chemical name | Ret time (min) | MS (M + H) |
|---|---|---|---|---|
| 30 | 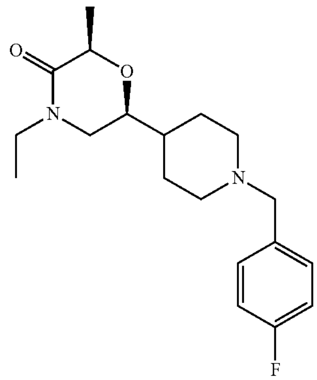 [SMILES: CCN1C[C@H](C2CCN(Cc3ccc(F)cc3)CC2)O[C@H](C)C1=O] | (2R,6S)-4-ethyl-6-(1-(4-fluorobenzyl)piperidin-4-yl)-2-methylmorpholin-3-one | 4.32 (meth B) | 335.1 |
| 31 | 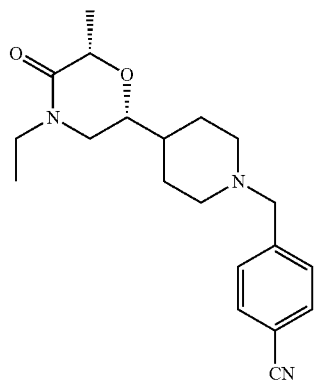 [SMILES: CCN1C[C@@H](C2CCN(Cc3ccc(C#N)cc3)CC2)O[C@@H](C)C1=O] | 4-((4-((2R,6S)-4-ethyl-6-methyl-5-oxomorpholin-2-yl)piperidin-1-yl)methyl)benzonitrile | 4.18 (meth B) | 342.1 |
| 32 | 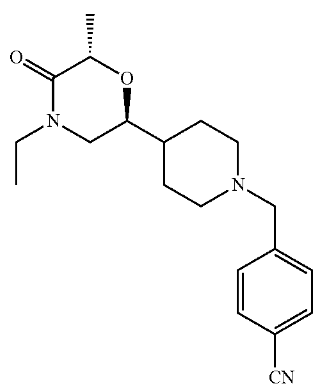 [SMILES: CCN1C[C@H](C2CCN(Cc3ccc(C#N)cc3)CC2)O[C@@H](C)C1=O] | 4-((4-((2S,6S)-4-ethyl-6-methyl-5-oxomorpholin-2-yl)piperidin-1-yl)methyl)benzonitrile | 4.33 (meth B) | 342.1 |
| 33 | 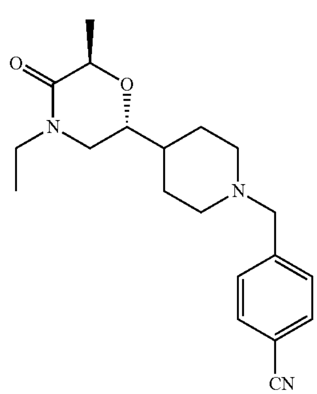 [SMILES: CCN1C[C@@H](C2CCN(Cc3ccc(C#N)cc3)CC2)O[C@H](C)C1=O] | 4-((4-((2R,6R)-4-ethyl-6-methyl-5-oxomorpholin-2-yl)piperidin-1-yl)methyl)benzonitrile | 4.32 (meth B) | 342.2 |

-continued

| EX | Structure | Chemical name | Ret time (min) | MS (M + H) |
|---|---|---|---|---|
| 34 | 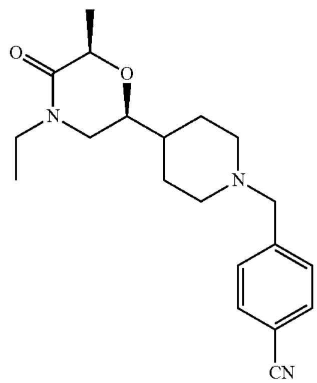 [SMILES: CCN1C[C@H](C2CCN(Cc3ccc(C#N)cc3)CC2)O[C@H](C)C1=O] | 4-((4-((2S,6R)-4-ethyl-6-methyl-5-oxomorpholin-2-yl)piperidin-1-yl)methyl)benzonitrile | 4.17 (meth B) | 342.2 |
| 35 | 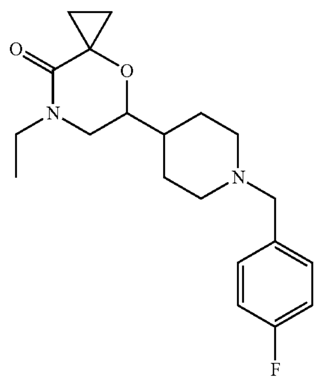 [SMILES: CCN1CC(C2CCN(Cc3ccc(F)cc3)CC2)OC2(CC2)C1=O] | 7-ethyl-5-(1-(4-fluorobenzyl)piperidin-4-yl)-4-oxa-7-azaspiro[2.5]octan-8-one | 4.74 (meth B) | 347.1 |
| 36 | 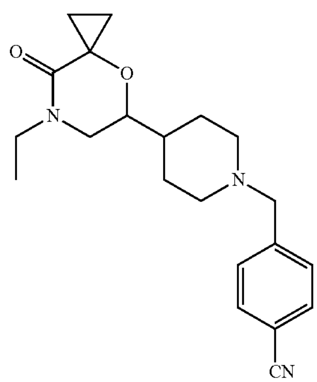 [SMILES: CCN1CC(C2CCN(Cc3ccc(C#N)cc3)CC2)OC2(CC2)C1=O] | 4-((4-(7-ethyl-8-oxo-4-oxa-7-azaspiro[2.5]octan-5-yl)piperidin-1-yl)methyl)benzonitrile | 4.53 (meth B) | 354.2 |
| 37 | 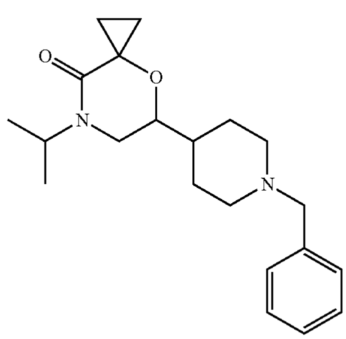 [SMILES: CC(C)N1CC(C2CCN(Cc3ccccc3)CC2)OC2(CC2)C1=O] | 5-(1-benzylpiperidin-4-yl)-7-isopropyl-4-oxa-7-azaspiro[2.5]octan-8-one | 4.92 (meth B) | 343.2 |

| EX | Structure | Chemical name | Ret time (min) | MS (M + H) |
|---|---|---|---|---|
| 38 | 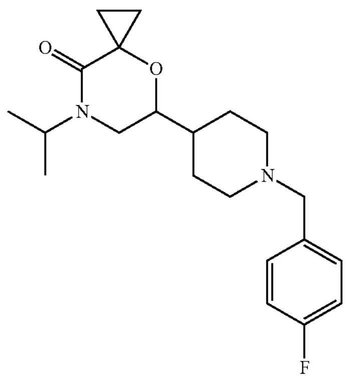 [SMILES: CC(C)N1CC(C2CCN(Cc3ccc(F)cc3)CC2)OC2(CC2)C1=O] | 5-(1-(4-fluorobenzyl)piperidin-4-yl)-7-isopropyl-4-oxa-7-azaspiro[2.5]octan-8-one | 5.05 (meth B) | 361.1 |
| 39 | 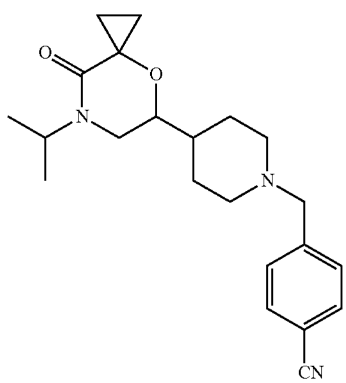 [SMILES: CC(C)N1CC(C2CCN(Cc3ccc(C#N)cc3)CC2)OC2(CC2)C1=O] | 4-((4-(7-isopropyl-8-oxo-4-oxa-7-azaspiro[2.5]octan-5-yl)piperidin-1-yl)methyl)benzonitrile | 4.83 (meth B) | 368.2 |

Examples 40 to 43 were prepared according to the procedure described in Example 7, using suitable starting materials:

| EX | Structure | Chemical name | Ret time (min) | MS (M + H) |
|---|---|---|---|---|
| 40 | 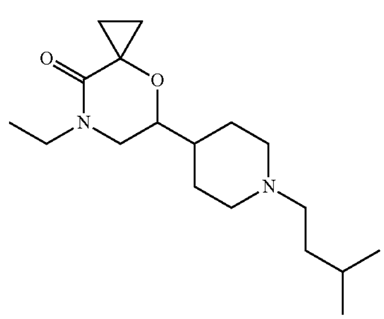 [SMILES: CCN1CC(C2CCN(CCC(C)C)CC2)OC2(CC2)C1=O] | 7-ethyl-5-(1-isopentylpiperidin-4-yl)-4-oxa-7-azaspiro[2.5]octan-8-one | 3.56 | 309.2 |

-continued

| EX | Structure | Chemical name | Ret time (min) | MS (M + H) |
|---|---|---|---|---|
| 41 | 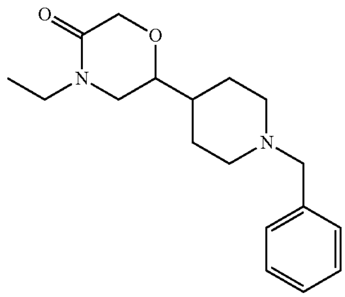 [SMILES: CCN1CC(C2CCN(Cc3ccccc3)CC2)OCC1=O] | 6-(1-benzylpiperidin-4-yl)-4-ethylmorpholin-3-one | 3.49 | 303.2 |
| 42 | 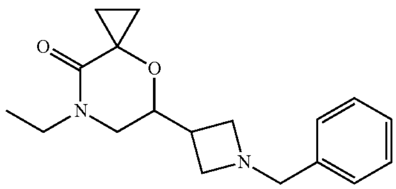 [SMILES: CCN1CC(C2CN(Cc3ccccc3)C2)OC2(CC2)C1=O] | 5-(1-benzylazetidin-3-yl)-7-ethyl-4-oxa-7-azaspiro[2.5]octan-8-one | 3.49 | 301.2 |
| 43 | 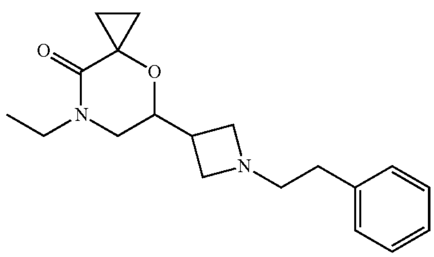 [SMILES: CCN1CC(C2CN(CCc3ccccc3)C2)OC2(CC2)C1=O] | 7-ethyl-5-(1-phenethylazetidin-3-yl)-4-oxa-7-azaspiro[2.5]octan-8-one | 3.63 | 315.1 |

Examples 44 to 45 were prepared according to the procedure described in Example 9, using suitable starting materials:

| EX | Structure | Chemical name | Ret time (min) | MS (M + H) |
|---|---|---|---|---|
| 44 | 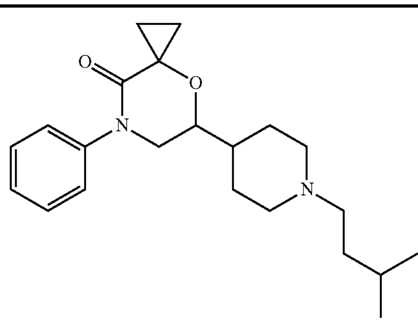 | 5-(1-isopentylpiperidin-4-yl)-7-phenyl-4-oxa-7-azaspiro[2.5]octan-8-one | 4.28 | 357.2 |
| 45 | 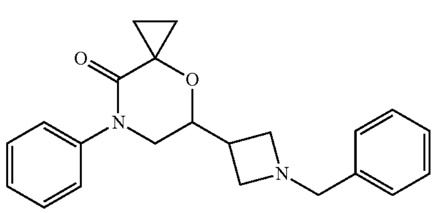 [SMILES: O=C1N(c2ccccc2)CC(C2CN(Cc3ccccc3)C2)OC12CC2] | 5-(1-benzylazetidin-3-yl)-7-phenyl-4-oxa-7-azaspiro[2.5]octan-8-one | 4.08 | 349.2 |

Examples 46 to 50 were prepared according to the procedure described in Example 11, using suitable starting materials:

| EX | Structure | Chemical name | Ret time (min) | MS (M + H) |
|---|---|---|---|---|
| 46 | 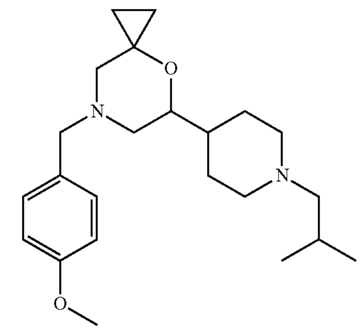 [SMILES: COc1ccc(CN2CC(C3CCN(CC(C)C)CC3)OC3(CC3)C2)cc1] | 5-(1-isobutylpiperidin-4-yl)-7-(4-methoxybenzyl)-4-oxa-7-azaspiro[2.5]octane | 4.76 | 373.3 |
| 47 | 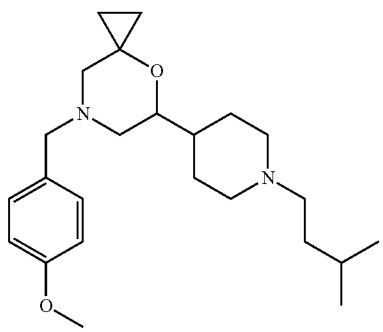 [SMILES: COc1ccc(CN2CC(C3CCN(CCC(C)C)CC3)OC3(CC3)C2)cc1] | 5-(1-isopentylpiperidin-4-yl)-7-(4-methoxybenzyl)-4-oxa-7-azaspiro[2.5]octane | 4.71 | 387.3 |
| 48 | 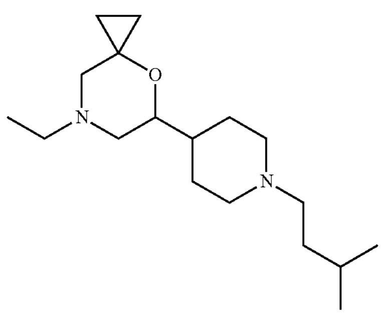 [SMILES: CCN1CC(C2CCN(CCC(C)C)CC2)OC2(CC2)C1] | 7-ethyl-5-(1-isopentylpiperidin-4-yl)-4-oxa-7-azaspiro[2.5]octane | 3.44 | 395.2 |
| 49 | 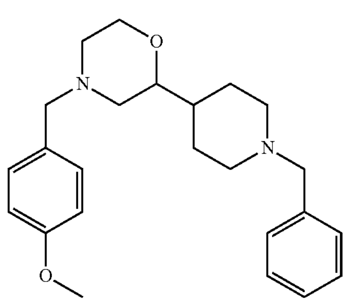 [SMILES: COc1ccc(CN2CCOC(C3CCN(Cc4ccccc4)CC3)C2)cc1] | 2-(1-benzylpiperidin-4-yl)-4-(4-methoxybenzyl)morpholine | 4.96 | 381.2 |

| EX | Structure | Chemical name | Ret time (min) | MS (M + H) |
|---|---|---|---|---|
| 50 | 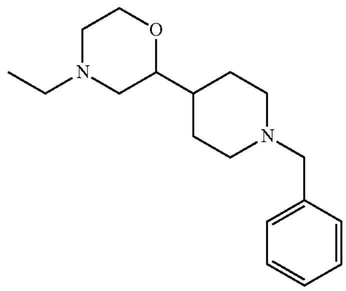 [SMILES: CCN1CCOC(C2CCN(Cc3ccccc3)CC2)C1] | 2-(1-benzylpiperidin-4-yl)-4-ethylmorpholine | 3.70 | 289.2 |

Example 51: (5-(1-Isopentylpiperidin-4-yl)-4-oxa-7-azaspiro[2.5]octan-7-yl)(phenyl)methanone

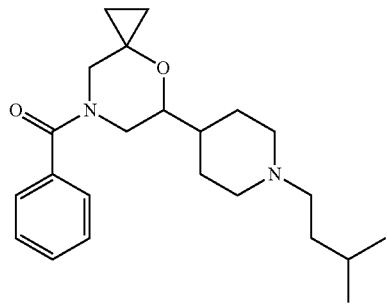 [SMILES: CC(C)CCN1CCC(C2CN(C(=O)c3ccccc3)CC3(CC3)O2)CC1]

Step 1: 5-(1-Isopentylpiperidin-4-yl)-4-oxa-7-azaspiro[2.5]octane acetate. Following the procedure described for the preparation of Intermediate 5 but starting from Example 47 (160 mg, 0.41 mmol), the title compound was obtained as a crude product that was used in the next step (131 mg, 97% yield).

Step 2: Title compound. Following the acylation procedure described for the preparation of Intermediate 6 but starting from the product obtained in Step 1 (131 mg, 0.41 mmol), the title compound was obtained (70 mg, 46% yield).

HPLC retention time: 4.26 min; MS; 371.2 (M+H)

Examples 52 and 53: (R)-5-(1-Benzylpiperidin-4-yl)-7-ethyl-4-oxa-7-azaspiro[2.5]octan-8-one and (S)-5-(1-benzylpiperidin-4-yl)-7-ethyl-4-oxa-7-azaspiro[2.5]octan-8-one

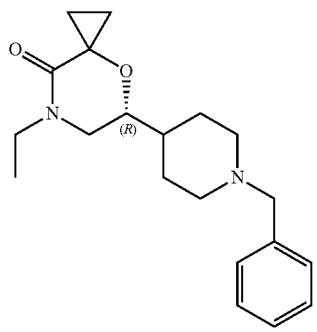

-continued

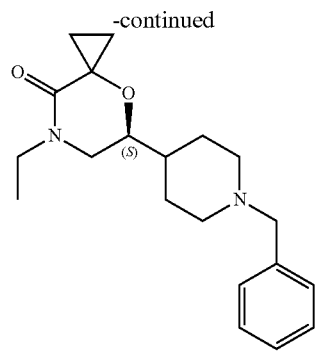

Starting from Example 5, a chiral preparative HPLC separation is carried out to give the title compounds.

Examples 54 and 55: (R)-5-(1-Benzylpiperidin-4-yl)-7-ethyl-4-oxa-7-azaspiro[2.5]octane and (S)-5-(1-benzylpiperidin-4-yl)-7-ethyl-4-oxa-7-azaspiro[2.5]octane

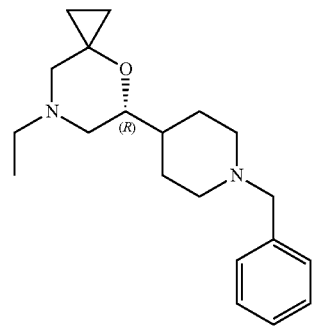

-continued

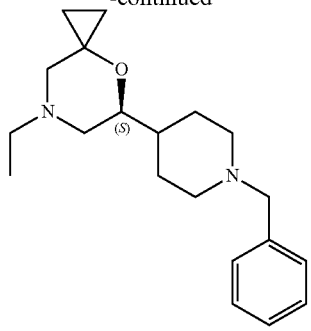

Starting from Example 14, a chiral preparative HPLC separation is carried out to give the title compounds.

Examples 56 and 57: (R)-(5-(1-Isopentylpiperidin-4-yl)-4-oxa-7-azaspiro[2.5]octan-7-yl)(phenyl)methanone and (S)-(5-(1-isopentylpiperidin-4-yl)-4-oxa-7-azaspiro[2.5]octan-7-yl)(phenyl)methanone

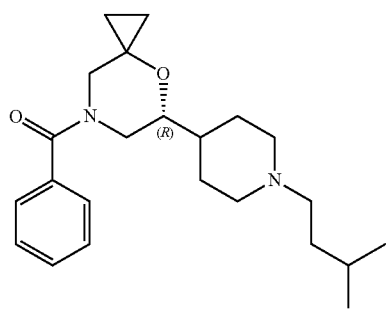

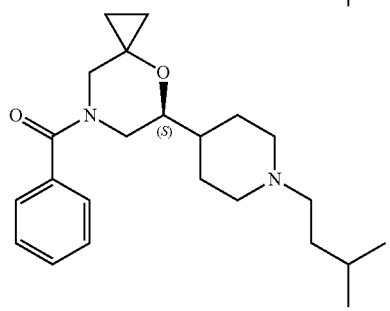

Starting from Example 51, a chiral preparative HPLC separation is carried out to give the title compounds.

Examples 58 and 59: (R)-5-(1-Benzylazetidin-3-yl)-7-phenyl-4-oxa-7-azaspiro[2.5]octan-8-one and (S)-5-(1-benzylazetidin-3-yl)-7-phenyl-4-oxa-7-azaspiro[2.5]octan-8-one

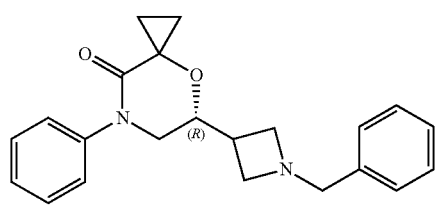

-continued

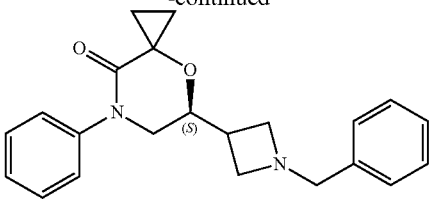

Starting from Example 45, a chiral preparative HPLC separation is carried out to give the title compounds.

Examples 60 and 61: (R)-(5-(1-Benzylpiperidin-4-yl)-4-oxa-7-azaspiro[2.5]octan-7-yl)(phenyl)methanone and (S)-(5-(1-benzylpiperidin-4-yl)-4-oxa-7-azaspiro[2.5]octan-7-yl)(phenyl)methanone

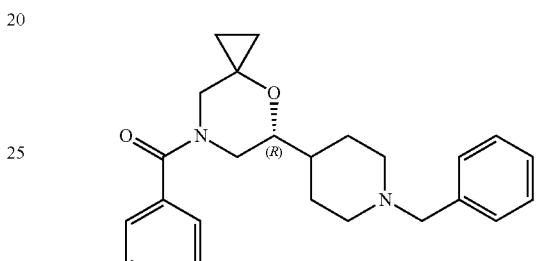

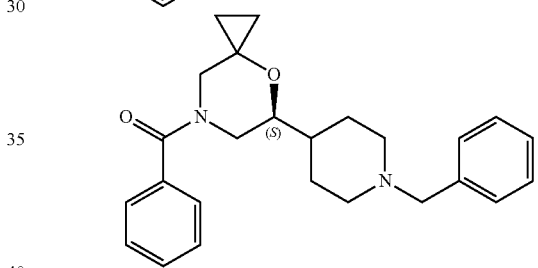

Starting from Example 4, a chiral preparative HPLC separation is carried out to give the title compounds.
Table of Examples with Binding to the $\sigma_1$-Receptor:
Biological Activity
Pharmacological Study
Human $\sigma_1$ Receptor Radioligand Assay To investigate binding properties of test compounds to human $\sigma_1$ receptor, transfected HEK-293 membranes and [$^3$H](+)-pentazocine (Perkin Elmer, NET-1056), as the radioligand, were used. The assay was carried out with 7 μg of membrane suspension, 5 nM of [$^3$H](+)-pentazocine in either absence or presence of either buffer or 10 μM Haloperidol for total and non-specific binding, respectively. Binding buffer contained Tris-HCl 50 mM at pH 8. Plates were incubated at 37° C. for 120 minutes. After the incubation period, the reaction mix was then transferred to MultiScreen HTS, FC plates (Millipore), filtered and plates were washed 3 times with ice-cold 10 mM Tris-HCL (pH7.4). Filters were dried and counted at approximately 40% efficiency in a MicroBeta scintillation counter (Perkin-Elmer) using EcoScint liquid scintillation cocktail
Results:

As this invention is aimed at providing a compound or a chemically related series of compounds which act as ligands of the $\sigma_1$ receptor it is a very preferred embodiment in which the compounds are selected which act as ligands of the $\sigma_1$ receptor and especially compounds which have a binding expressed as $K_i$ which is preferably <1000 nM, more preferably <500 nM, even more preferably <100 nM.

The following scale as been adopted for representing the binding to the $\sigma_1$ receptor expressed as $K_i$:

+ $K_i$-$\sigma_1$>=500 nM
++ $K_i$-$\sigma_1$<500 nM
+++ $K_i$-$\sigma_1$<100 nM All compounds prepared in the present application exhibit binding to the $\sigma_1$ receptor, in particular the following binding results are shown:

| EXAMPLE | $K_i$-$\sigma_1$ |
|---|---|
| 1 | + |
| 2 | ++ |
| 3 | ++ |
| 4 | +++ |
| 5 | +++ |
| 6 | + |
| 7 | ++ |
| 8 | ++ |
| 9 | + |
| 10 | ++ |
| 11 | ++ |
| 12 | +++ |
| 13 | + |
| 14 | +++ |
| 15 | + |
| 16 | ++ |
| 21 | ++ |
| 22 | ++ |
| 23 | + |
| 24 | + |
| 25 | + |
| 26 | + |
| 27 | + |
| 28 | + |
| 29 | + |
| 30 | + |
| 31 | + |
| 32 | + |
| 33 | + |
| 34 | + |
| 35 | + |
| 36 | + |
| 37 | + |
| 38 | + |
| 39 | + |
| 40 | ++ |
| 41 | +++ |
| 42 | ++ |
| 43 | ++ |
| 44 | ++ |
| 45 | +++ |
| 46 | ++ |
| 47 | +++ |
| 48 | ++ |
| 49 | +++ |
| 50 | +++ |
| 51 | +++ |

The invention claimed is:
1. A compound of general Formula (I):

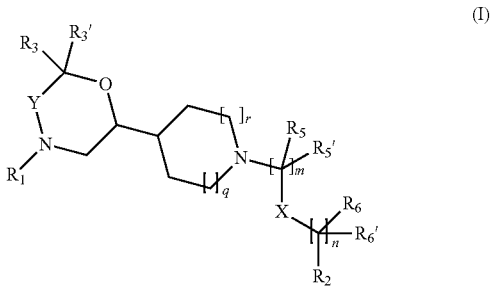

wherein
$R_1$ is

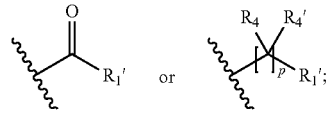

m is 1, 2, 3, 4 or 5;
n is 0, 1, 2, 3, 4 or 5;
p is 0 or 1;
q is 0, 1 or 2;
r is 0, 1 or 2;
Y is —$CH_2$— or —C(O)—;
X is a bond, —C($R_x R_{x'}$)—, —C(O)—, —O—, —C(O)N$R_7$—, —N$R_7$C(O)— or —C(O)O—;
  wherein $R_x$ is selected from the group consisting of halogen or substituted or unsubstituted $C_{1-6}$ alkyl, substituted or unsubstituted $C_{2-6}$ alkenyl substituted or unsubstituted $C_{2-6}$ alkynyl, and —O$R_7$;
  $R_{x'}$ is selected from the group consisting of hydrogen, halogen or substituted or unsubstituted $C_{1-6}$ alkyl, substituted or unsubstituted $C_{2-6}$ alkenyl and substituted or unsubstituted $C_{2-6}$ alkynyl;
  $R_7$ is selected from the group consisting of hydrogen, substituted or unsubstituted $C_{1-6}$ alkyl, substituted or unsubstituted $C_{2-6}$ alkenyl and substituted or unsubstituted $C_{2-6}$ alkynyl;
$R_{1'}$ is selected from the group consisting of substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;
$R_2$ is selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl,
$R_3$ and $R_{3'}$ are independently selected from the group consisting of hydrogen, substituted or unsubstituted $C_{1-6}$ alkyl, substituted or unsubstituted $C_{2-6}$ alkenyl and substituted or unsubstituted $C_{2-6}$ alkynyl; or
$R_3$ and $R_{3'}$, together with the carbon atom to which they are attached, form a substituted or unsubstituted cycloalkyl;

R<sub>4</sub> and R<sub>4'</sub> are independently selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, —CHOR<sub>9</sub> and —C(O)OR<sub>9</sub>;
  wherein R<sub>9</sub> is selected from the group consisting of hydrogen, substituted or unsubstituted $C_{1-9}$ alkyl, substituted or unsubstituted $C_{2-9}$ alkenyl and substituted or unsubstituted $C_{2-9}$ alkynyl;

R<sub>5</sub> and R<sub>5'</sub> are independently selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, —CHOR<sub>8</sub> and —C(O)OR<sub>8</sub>;
  wherein R<sub>8</sub> is selected from the group consisting of hydrogen, substituted or unsubstituted $C_{1-6}$ alkyl, substituted or unsubstituted $C_{2-6}$ alkenyl and substituted or unsubstituted $C_{2-6}$ alkynyl; or R<sub>5</sub> and R<sub>5'</sub>, together with the carbon atom to which they are attached, form a substituted or unsubstituted cycloalkyl or a substituted or unsubstituted heterocyclyl;

R<sub>6</sub> and R<sub>6'</sub> are independently selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, —CHOR<sub>10</sub> and —C(O)OR<sub>10</sub>;
  wherein R<sub>10</sub> is selected from the group consisting of hydrogen, substituted or unsubstituted $C_{1-6}$ alkyl, substituted or unsubstituted $C_{2-6}$ alkenyl and substituted or unsubstituted $C_{2-6}$ alkynyl;

optionally as a stereoisomer, including enantiomers and diastereomers, a racemate or a mixture of at least two stereoisomers, including enantiomers and/or diastereomers, in any mixing ratio, or a corresponding salt thereof, or a corresponding solvate thereof;

with the following proviso applying:

R<sub>1</sub> is not

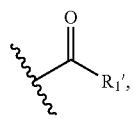

when Y is —C(O)—.

2. The compound according to claim 1, which is a compound of Formula (I')

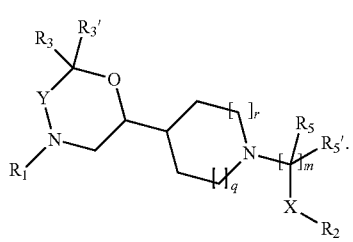

(I')

3. The compound according to claim 1, which is a compound of Formula (I<sup>2'</sup>)

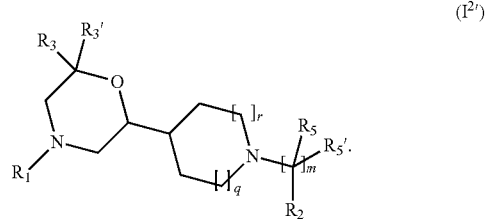

(I<sup>2'</sup>)

4. The compound according to claim 1, which is a compound of Formula (I<sup>3'</sup>)

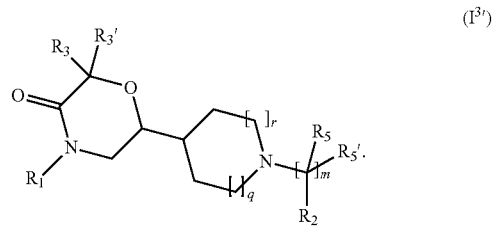

(I<sup>3'</sup>)

5. The compound according to claim 1, which is a compound of Formula (I<sup>4'</sup>), (I<sup>4a'</sup>), (I<sup>4b'</sup>) or (I<sup>4c'</sup>)

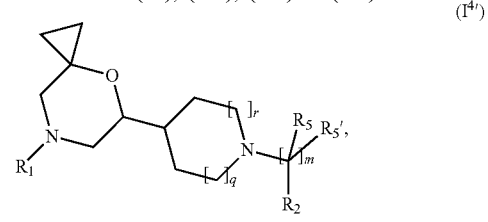

(I<sup>4'</sup>)

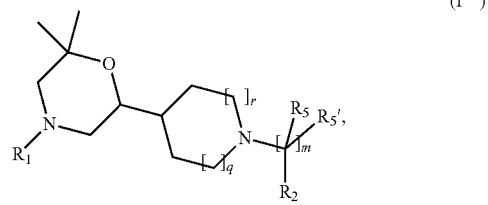

(I<sup>4a'</sup>)

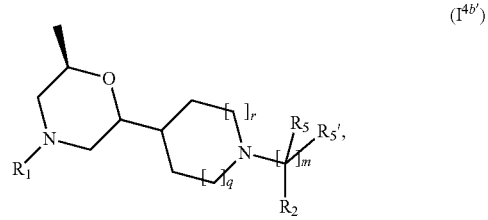

(I<sup>4b'</sup>)

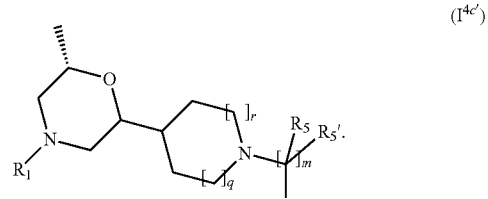

(I<sup>4c'</sup>)

6. The compound according to claim 1, which is a compound of Formula (I⁵'), (I⁵ᵃ'), (I⁵ᵇ') or (I⁵ᶜ')

(I⁵')

(I⁵ᵃ')

(I⁵ᵇ')

(I⁵ᶜ')

7. The compound according to claim 1, wherein $R_{1'}$ is selected from the group consisting of substituted or unsubstituted $C_{1-6}$ alkyl and substituted or unsubstituted aryl.

8. The compound according to claim 7, wherein $R_{1'}$ is a substituted or unsubstituted group selected from the group consisting of methyl, ethyl, isopropyl and phenyl.

9. The compound according to claim 1, wherein $R_2$ is selected from the group consisting of substituted or unsubstituted $C_{1-6}$ alkyl, and substituted or unsubstituted aryl.

10. The compound according to claim 9, wherein $R_2$ is a substituted or unsubstituted group selected from the group consisting of methyl, isopropyl, isobutyl and phenyl.

11. The compound according to claim 1, wherein $R_3$ and $R_{3'}$, together with the carbon atom to which they are attached, form a substituted or unsubstituted cycloalkyl.

12. The compound according to claim 11, wherein $R_3$ and $R_{3'}$ form a substituted or unsubstituted $C_{3-6}$ cycloalkyl.

13. The compound according to claim 11, wherein $R_3$ and $R_{3'}$ form a substituted or unsubstituted cyclopropyl.

14. The compound according to claim 1, which is selected from the group consisting of:
7-(4-methoxybenzyl)-5-(1-phenethylpiperidin-4-yl)-4-oxa-7-azaspiro[2.5]octan-8-one,
(5-(1-phenethylpiperidin-4-yl)-4-oxa-7-azaspiro[2.5]octan-7-yl)(phenyl)methanone,
5-(1-benzylpiperidin-4-yl)-7-(4-methoxybenzyl)-4-oxa-7-azaspiro[2.5]octan-8-one,
(5-(1-benzylpiperidin-4-yl)-4-oxa-7-azaspiro[2.5]octan-7-yl)(phenyl)methanone,
5-(1-benzylpiperidin-4-yl)-7-ethyl-4-oxa-7-azaspiro[2.5]octan-8-one,
5-(1-ethylpiperidin-4-yl)-7-(4-methoxybenzyl)-4-oxa-7-azaspiro[2.5]octan-8-one,
7-ethyl-5-(1-phenethylpiperidin-4-yl)-4-oxa-7-azaspiro[2.5]octan-8-one,
7-isopropyl-5-(1-phenethylpiperidin-4-yl)-4-oxa-7-azaspiro[2.5]octan-8-one,
5-(1-phenethylpiperidin-4-yl)-7-phenyl-4-oxa-7-azaspiro[2.5]octan-8-one,
5-(1-benzylpiperidin-4-yl)-7-phenyl-4-oxa-7-azaspiro[2.5]octan-8-one,
7-ethyl-5-(1-phenethylpiperidin-4-yl)-4-oxa-7-azaspiro[2.5]octane,
5-(1-benzylpiperidin-4-yl)-7-(4-methoxybenzyl)-4-oxa-7-azaspiro[2.5]octane,
7-(4-methoxybenzyl)-5-(1-phenethylpiperidin-4-yl)-4-oxa-7-azaspiro[2.5]octane and
5-(1-benzylpiperidin-4-yl)-7-ethyl-4-oxa-7-azaspiro[2.5]octane.

15. The compound according to claim 1, which is selected from the group consisting of:
5-(1-isobutylpiperidin-4-yl)-7-(4-methoxybenzyl)-4-oxa-7-azaspiro[2.5]octan-8-one,
5-(1-isopentylpiperidin-4-yl)-7-(4-methoxybenzyl)-4-oxa-7-azaspiro[2.5]octan-8-one,
(2S,6R)-4-ethyl-6-(1-isopentylpiperidin-4-yl)-2-methylmorpholin-3-one,
(2S,6S)-4-ethyl-6-(1-isopentylpiperidin-4-yl)-2-methylmorpholin-3-one,
(2R,6R)-4-ethyl-6-(1-isopentylpiperidin-4-yl)-2-methylmorpholin-3-one,
(2R,6S)-4-ethyl-6-(1-isopentylpiperidin-4-yl)-2-methylmorpholin-3-one,
6-(1-benzylpiperidin-4-yl)-4-(4-methoxybenzyl)morpholin-3-one,
7-ethyl-5-(1-isopentylazetidin-3-yl)-4-oxa-7-azaspiro[2.5]octan-8-one,
(2S,6R)-6-(1-benzylpiperidin-4-yl)-4-ethyl-2-methylmorpholin-3-one,
(2S,6S)-6-(1-benzylpiperidin-4-yl)-4-ethyl-2-methylmorpholin-3-one,
(2R,6R)-6-(1-benzylpiperidin-4-yl)-4-ethyl-2-methylmorpholin-3-one,
(2R,6S)-6-(1-benzylpiperidin-4-yl)-4-ethyl-2-methylmorpholin-3-one,
(2S,6R)-4-ethyl-6-(1-(4-fluorobenzyl)piperidin-4-yl)-2-methylmorpholin-3-one,
(2S,6S)-4-ethyl-6-(1-(4-fluorobenzyl)piperidin-4-yl)-2-methylmorpholin-3-one,
(2R,6R)-4-ethyl-6-(1-(4-fluorobenzyl)piperidin-4-yl)-2-methylmorpholin-3-one,
(2R,6S)-4-ethyl-6-(1-(4-fluorobenzyl)piperidin-4-yl)-2-methylmorpholin-3-one,
4-((4-((2R,6S)-4-ethyl-6-methyl-5-oxomorpholin-2-yl)piperidin-1-yl)methyl)benzonitrile,
4-((4-((2S,6S)-4-ethyl-6-methyl-5-oxomorpholin-2-yl)piperidin-1-yl)methyl)benzonitrile,
4-((4-((2R,6R)-4-ethyl-6-methyl-5-oxomorpholin-2-yl)piperidin-1-yl)methyl)benzonitrile,
4-((4-((2S,6R)-4-ethyl-6-methyl-5-oxomorpholin-2-yl)piperidin-1-yl)methyl)benzonitrile,
7-ethyl-5-(1-(4-fluorobenzyl)piperidin-4-yl)-4-oxa-7-azaspiro[2.5]octan-8-one, 4-((4-(7-ethyl-8-oxo-4-oxa-7-azaspiro[2.5]octan-5-yl)piperidin-1-yl)methyl)benzonitrile,
5-(1-benzylpiperidin-4-yl)-7-isopropyl-4-oxa-7-azaspiro[2.5]octan-8-one,
5-(1-(4-fluorobenzyl)piperidin-4-yl)-7-isopropyl-4-oxa-7-azaspiro[2.5]octan-8-one,
4-((4-(7-isopropyl-8-oxo-4-oxa-7-azaspiro[2.5]octan-5-yl)piperidin-1-yl)methyl)benzonitrile,
7-ethyl-5-(1-isopentylpiperidin-4-yl)-4-oxa-7-azaspiro[2.5]octan-8-one,
6-(1-benzylpiperidin-4-yl)-4-ethylmorpholin-3-one,
5-(1-benzylazetidin-3-yl)-7-ethyl-4-oxa-7-azaspiro[2.5]octan-8-one,
7-ethyl-5-(1-phenethylazetidin-3-yl)-4-oxa-7-azaspiro[2.5]octan-8-one,
5-(1-isopentylpiperidin-4-yl)-7-phenyl-4-oxa-7-azaspiro[2.5]octan-8-one,
5-(1-benzylazetidin-3-yl)-7-phenyl-4-oxa-7-azaspiro[2.5]octan-8-one,
5-(1-isobutylpiperidin-4-yl)-7-(4-methoxybenzyl)-4-oxa-7-azaspiro[2.5]octane,
5-(1-isopentylpiperidin-4-yl)-7-(4-methoxybenzyl)-4-oxa-7-azaspiro[2.5]octane,
7-ethyl-5-(1-isopentylpiperidin-4-yl)-4-oxa-7-azaspiro[2.5]octane,
2-(1-benzylpiperidin-4-yl)-4-(4-methoxybenzyl)morpholine,
2-(1-benzylpiperidin-4-yl)-4-ethylmorpholine,
(5-(1-Isopentylpiperidin-4-yl)-4-oxa-7-azaspiro[2.5]octan-7-yl)(phenyl)methanone,
(R)-5-(1-Benzylpiperidin-4-yl)-7-ethyl-4-oxa-7-azaspiro[2.5]octan-8-one,
(S)-5-(1-benzylpiperidin-4-yl)-7-ethyl-4-oxa-7-azaspiro[2.5]octan-8-one,
(R)-5-(1-Benzylpiperidin-4-yl)-7-ethyl-4-oxa-7-azaspiro[2.5]octane,
(S)-5-(1-benzylpiperidin-4-yl)-7-ethyl-4-oxa-7-azaspiro[2.5]octane,
(R)-(5-(1-Isopentylpiperidin-4-yl)-4-oxa-7-azaspiro[2.5]octan-7-yl)(phenyl)methanone,
(S)-(5-(1-isopentylpiperidin-4-yl)-4-oxa-7-azaspiro[2.5]octan-7-yl)(phenyl)methanone,
(R)-5-(1-Benzylazetidin-3-yl)-7-phenyl-4-oxa-7-azaspiro[2.5]octan-8-one,
(S)-5-(1-benzylazetidin-3-yl)-7-phenyl-4-oxa-7-azaspiro[2.5]octan-8-one,
(R)-(5-(1-Benzylpiperidin-4-yl)-4-oxa-7-azaspiro[2.5]octan-7-yl)(phenyl)methanone and
(S)-(5-(1-benzylpiperidin-4-yl)-4-oxa-7-azaspiro[2.5]octan-7-yl)(phenyl)methanone.

16. A process for the preparation of the compound according to claim 1, wherein $R_1$ is —$(CR_4R_{4'})_pR_{1'}$, which process comprises:

a) the intramolecular cyclization of a compound of formula VII

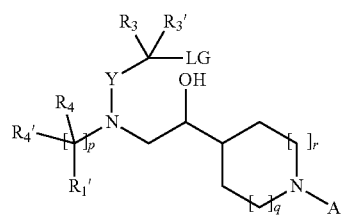

VII $A = (CR_5R_5')_mX(CR_6R_6')_nR_2$ wherein LG represents a leaving group, including halogen, mesylate, tosylate or triflate, with the proviso that when Y=CO, LG represents chloro or bromo, or b) the reaction of a compound of formula VIIIH

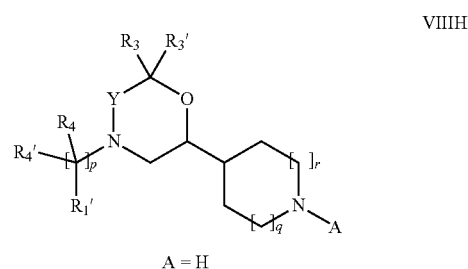

VIIIH

A = H with a compound of formula IX, X or XI,

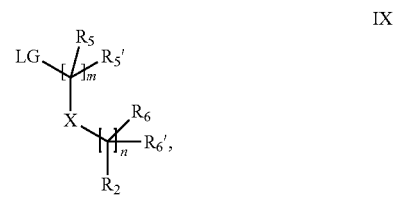

IX

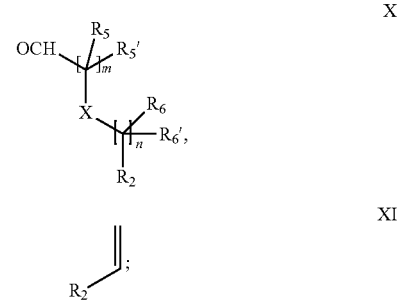

X

XI wherein LG represents a leaving group, including halogen, mesylate, tosylate or triflate, or c1) when Y is $CH_2$, by the alkylation of a compound of formula XIII

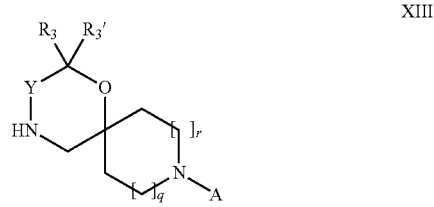

XIII $A = (CR_5R_5')_mX(CR_6R_6')_nR_2$ with a compound of formula IV

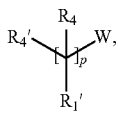

wherein the compound of formula IV is an alkylating agent and W is a leaving group, or alternatively by the reductive amination reaction of a compound of formula XIII with a compound of formula IV, wherein the compound of formula IV is an aldehyde or ketone and W is a C(O)H or C(O) group;

or c2) when Y is C(O), by the alkylation of a compound of formula XIII

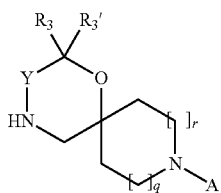

with a compound of formula IV

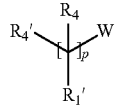

wherein the compound of formula IV is an alkylating agent and W is a leaving group, wherein $R_1'$, $R_2$, $R_3$, $R_3'$, $R_4$, $R_4'$, $R_5$, $R_5'$, $R_6$, $R_6'$, $R_7$, $R_8$, $R_9$, $R_{10}$, $R_x$, $R_{x'}$, X, Y, m, n, p, q and r have the meanings as defined in claim for the compound of Formula (I).

17. A process for the preparation of the compound of Formula (I) according to claim 1, employing a compound of Formula Ia, II, IIP, III, IIIP, IV, V, VP, VI, VII, VIIP, VIIIP, VIIIH, IX, X, XI, XII, XIIP, XIII, XIIIP, XIIIH, XIV, XIVP, XV, XVP, XVI, XVIP, XVIH, Ib, XVIIP, XVIIH, Ic, XVIIIP, Id, XIXP, XIXH, Ie, XXP, XXH, XXI, XXIP, XXIH, XXII, XXIIP, XXIIH, XXIII, XXIIIP, XXIIIH, XXIV, XXIVP, XXIVH, XXV, XXVP, XXVH, If, XXVIP, XXVIH, XXVIIa, XXVIIb, XXVIIc, Ig, XXVIIIP, XXVIIIH, Ih, XXIXP, XXIXH, Ii, XXXP, XXXH, XXXI, XXXIP, XXXIH, XXXII, XXXIIP, XXXIIIP, XXXIII, XXXIIIP, XXXIIIH, XXXIV, XXXIVP, XXXIVH, XXXV, Ij, XXXVIP or XXXVIH,

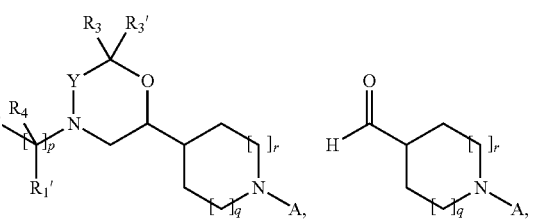

Ia A = $(CR_5R_5')_mX(CR_6R_6')_nR_2$
VIIIP A = P
VIIIH A = H

II A = $(CR_5R_5')_mX(CR_6R_6')_nR_2$
IIP A = P

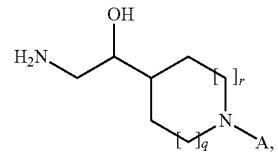

III A = $(CR_5R_5')_mX(CR_6R_6')_nR_2$
IIIP A = P

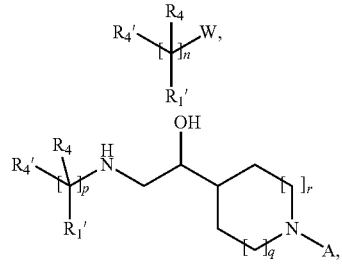

V A = $(CR_5R_5')_mX(CR_6R_6')_nR_2$
VP A = P

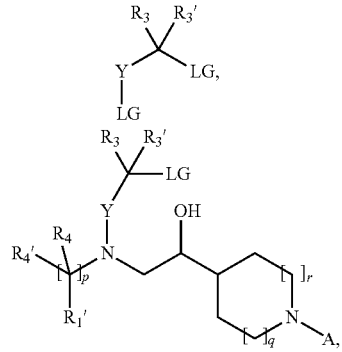

VII A = $(CR_5R_5')_mX(CR_6R_6')_nR_2$
VIIP A = P

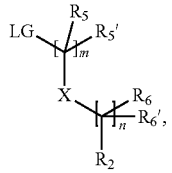

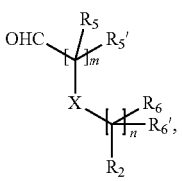

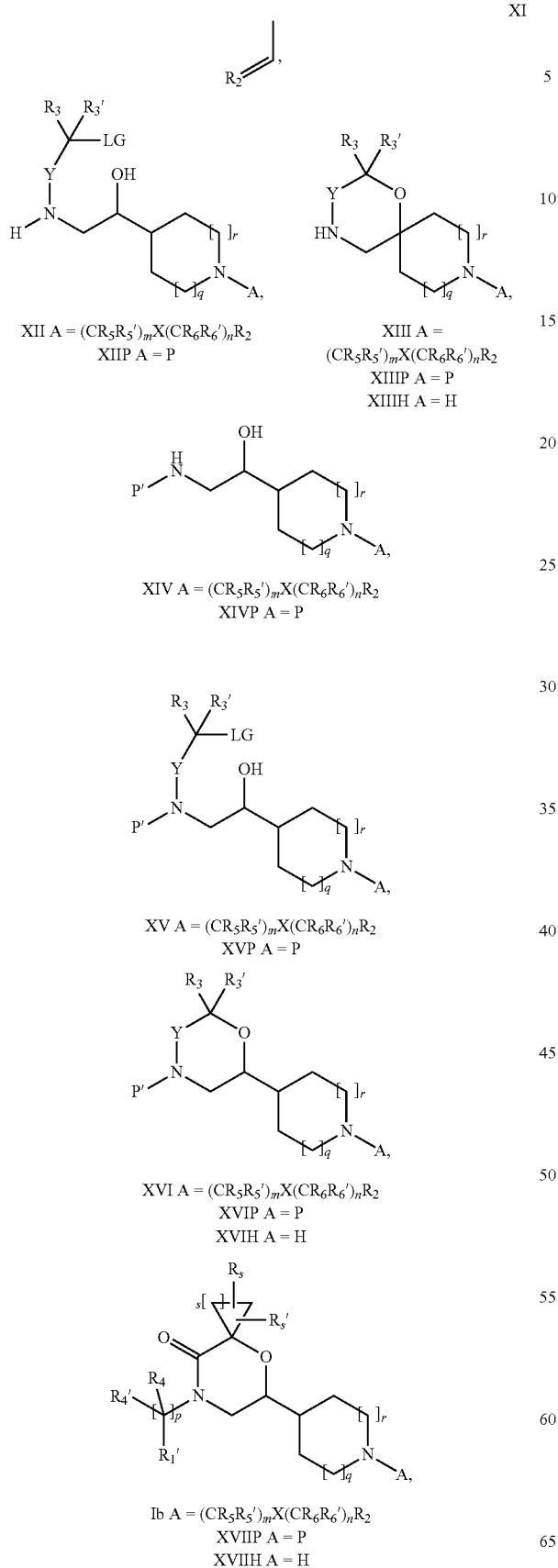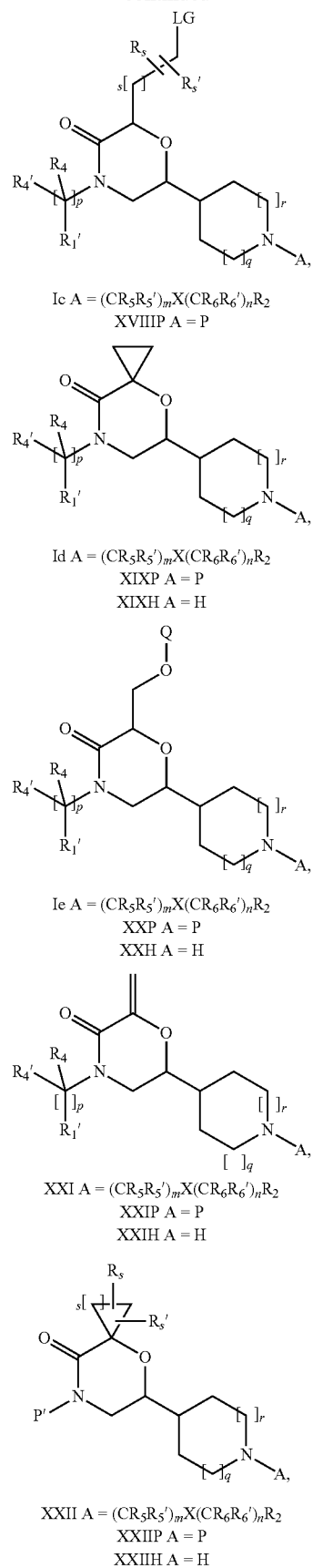

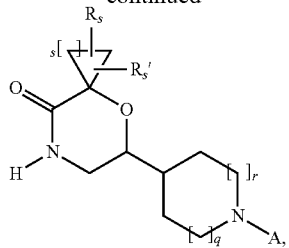

XXIII A = (CR₅R₅')ₘX(CR₆R₆')ₙR₂
XXIIIP A = P
XXIIIH A = H

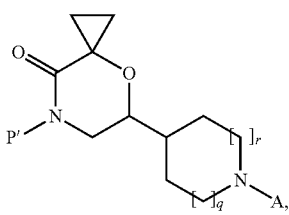

XXIV A = (CR₅R₅')ₘX(CR₆R₆')ₙR₂
XXIVP A = P
XXIVH A = H

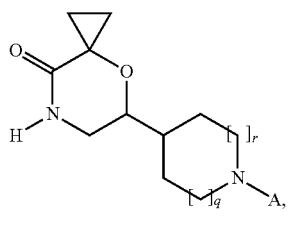

XXV A = (CR₅R₅')ₘX(CR₆R₆')ₙR₂
XXVP A = P
XXVH A = H

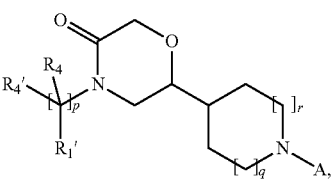

If A = (CR₅R₅')ₘX(CR₆R₆')ₙR₂
XXVIP A = P
XXIIIH A = H

R₃X',  XXVIIa

R₃'X',  XXVIIb

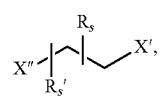  XXVIIc

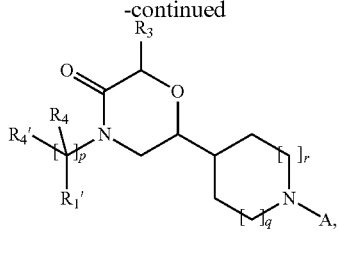

Ig A = (CR₅R₅')ₘX(CR₆R₆')ₙR₂
XVIIIP A = P
XVIIIH A = H

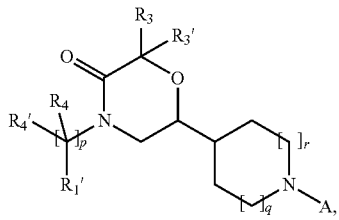

Ih A = (CR₅R₅')ₘX(CR₆R₆')ₙR₂
XXIXP A = P
XXIXH A = H

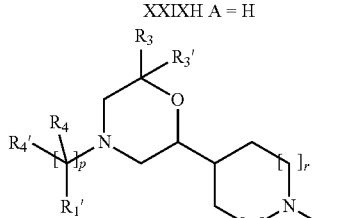

Ii A = (CR₅R₅')ₘX(CR₆R₆')ₙR₂
XXXP A = P
XXXH A = H

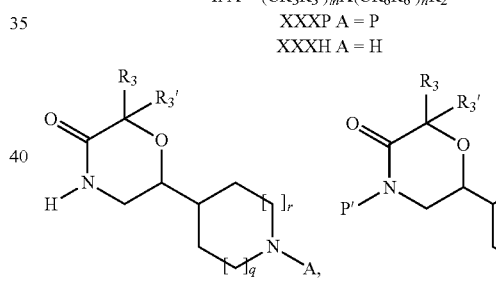

XXXI A = (CR₅R₅')ₘX(CR₆R₆')ₙR₂    XXXII A = (CR₅R₅')ₘX(CR₆R₆')ₙR₂
XXXIP A = P                        XXXIIP A = P
XXXIH A = H                        XXXIIH A = H

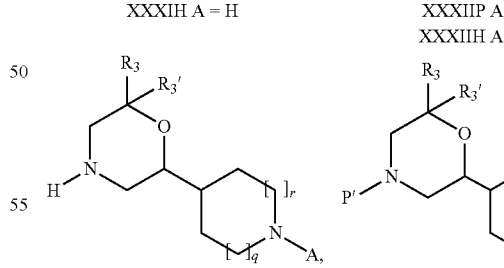

XXXIII A = (CR₅R₅')ₘX(CR₆R₆')ₙR₂    XXXIV A = (CR₅R₅')ₘX(CR₆R₆')ₙR₂
XXXIIIP A = P                        XXXIVP A = P
XXXIIIH A = H                        XXXIVH A = H

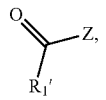   XXXV

-continued

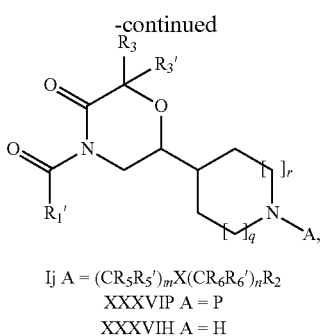

Ij A = (CR$_5$R$_5'$)$_m$X(CR$_6$R$_6'$)$_n$R$_2$
XXXVIP A = P
XXXVIIH A = H wherein R$_1'$, R$_2$, R$_3$, R$_3'$, R$_4$, R$_4'$, R$_5$, R$_5'$, R$_6$, R$_6'$, R$_7$, R$_8$, R$_9$, R$_{10}$, R$_x$, R$_{x'}$, X, Y, m, n, p, q and r have the meanings as defined in claim 1 for the compound of Formula (I), LG represents a leaving group, including halogen, mesylate, tosylate and triflate, with the proviso that when Y=CO, LG represents chloro or bromo, W represents an aldehyde or another leaving group, including halogen, mesylate, tosylate and triflate, P represents a suitable protecting group, including Boc, P' represents an orthogonal protecting group, including 4-methoxybenzyl and benzyl, Q represents methyl or benzyl, X' represents a leaving group, including halogen, mesylate, tosylate and triflate, and Z represents OH or halogen, including bromo and chloro.

18. A pharmaceutical composition which comprises the compound according to claim 1, or a pharmaceutically acceptable salt thereof, and a pharmaceutically acceptable carrier, adjuvant or vehicle.

19. A method of treating pain in a subject in need thereof, comprising administration of an effective amount of the compound according to claim 1.

20. The method according to claim 19, wherein the pain is selected from the group consisting of medium to severe pain, visceral pain, chronic pain, cancer pain, migraine, inflammatory pain, acute pain, neuropathic pain, allodynia and hyperalgesia.

* * * * *

UNITED STATES PATENT AND TRADEMARK OFFICE
CERTIFICATE OF CORRECTION

PATENT NO. : 10,421,750 B2  
APPLICATION NO. : 15/769520  
DATED : September 24, 2019  
INVENTOR(S) : Marina Virgili-Bernado and Carlos Alegret-Molina Page 1 of 1

It is certified that error appears in the above-identified patent and that said Letters Patent is hereby corrected as shown below:

On the Title Page

Column 1 under inventors: The city for the second inventor should read -- Barcelona --.

Column 2 under OTHER PUBLICATIONS: The last reference, Line 1 "frorn" should read -- from --.

In the Claims

Column 182, Line 63 Claim 17 in formula X: "m" should be -- m=1-4 --.

Column 183, Line 5 Claim 17 in formula XI: " $R_2{=}$ " should be -- $R_2{=}$ --.

Signed and Sealed this  
Nineteenth Day of November, 2019

Andrei Iancu  
*Director of the United States Patent and Trademark Office*